(12) United States Patent
Love et al.

(10) Patent No.: US 6,630,128 B1
(45) Date of Patent: Oct. 7, 2003

(54) PORPHYRIN DERIVATIVES THEIR USE IN PHOTODYNAMIC THERAPY AND MEDICAL DEVICES CONTAINING THEM

(75) Inventors: William Guy Love, West Sussex (GB); Michael John Cook, Norwich (GB); David Andrew Russell, Norfolk (GB)

(73) Assignees: Destiny Pharma Limited, Brighton (GB); University of East Anglia, Norwich (GB)

( * ) Notice: Subject to any disclaimer, the term of this patent is extended or adjusted under 35 U.S.C. 154(b) by 0 days.

(21) Appl. No.: 09/786,139

(22) PCT Filed: Aug. 31, 1999

(86) PCT No.: PCT/GB99/02864

§ 371 (c)(1),
(2), (4) Date: Apr. 30, 2001

(87) PCT Pub. No.: WO00/12512

PCT Pub. Date: Mar. 9, 2000

(30) Foreign Application Priority Data

Aug. 28, 1999 (GB) ............................................. 9818789
Jun. 4, 1999 (GB) ............................................. 9912971

(51) Int. Cl.[7] ..................... A61K 31/40; C07D 487/22; C07F 3/02; C07F 3/06
(52) U.S. Cl. ................... 424/9.362; 424/9.61; 514/185; 514/410; 540/145
(58) Field of Search ................ 540/145; 514/185, 514/410; 424/9.362, 9.61

(56) References Cited

U.S. PATENT DOCUMENTS 5,051,415 A     9/1991 Morgan ..................... 514/185

(List continued on next page.)

FOREIGN PATENT DOCUMENTS

EP     0 251 915     1/1988

(List continued on next page.)

OTHER PUBLICATIONS

Bonnett, "Photosensitizers of the Porphyrin and Phthalocyanine Series for Photodynamic Therapy," *Chem Soc Rev* 19–33 (1995).

(List continued on next page.)

*Primary Examiner*—Richard L. Raymond
(74) *Attorney, Agent, or Firm*—Holland & Knight LLP

(57) ABSTRACT

There is provided a compound of formula (I), wherein $R^1$, $R^2$, $R^3$, $R^4$, $R^5$, $R^6$, $R^7$, $R^8$, $R^9$, X, $Y^1$, $Y^2$, $Y^3$, Z, M, A–B and C–D have meanings given in the description, which are useful in the treatment of medical conditions for which a photodynamic compound is indicated. Compositions, apparatus and methods of treatment of a medical condition for which a photodynamic compound is indicated are also disclosed.

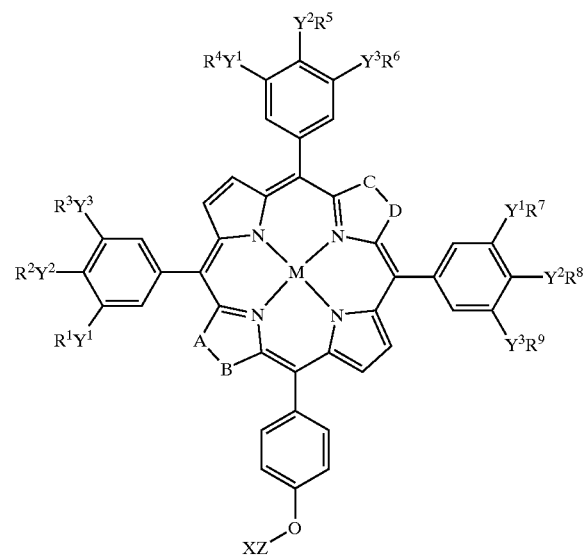

65 Claims, 3 Drawing Sheets

U.S. PATENT DOCUMENTS

| | | | | |
|---|---|---|---|---|
| 5,053,423 | A | 10/1991 | Liu | 514/410 |
| 5,159,065 | A | 10/1992 | Sessler et al. | 534/15 |
| 5,171,749 | A | 12/1992 | Levy et al. | 514/410 |
| 5,284,647 | A | 2/1994 | Niedballa et al. | 424/81 |
| 5,411,580 | A | 5/1995 | Tsuchida et al. | 96/5 |
| 5,543,514 | A | 8/1996 | Sessler et al. | 540/472 |
| 5,587,478 | A | 12/1996 | Sessler et al. | 540/474 |
| 5,594,136 | A | 1/1997 | Sessler et al. | 540/472 |
| 5,622,685 | A | 4/1997 | Sinn et al. | 424/1.65 |
| 5,672,490 | A | 9/1997 | Sessler et al. | 435/91.1 |
| 5,674,467 | A | 10/1997 | Maier et al. | 474/1.65 |
| 5,697,973 | A | 12/1997 | Peyman et al. | 623/6 |
| 5,707,986 | A | 1/1998 | Miller et al. | 514/185 |
| 5,716,364 | A | 2/1998 | Makker et al. | 600/107 |
| 5,776,138 | A | 7/1998 | Vidal et al. | 606/107 |
| 5,994,339 | A | 11/1999 | Crapo et al. | 514/185 |

FOREIGN PATENT DOCUMENTS

| | | |
|---|---|---|
| EP | 0 258 752 | 3/1988 |
| EP | 0 464 718 | 1/1992 |
| EP | 0 475 053 | 3/1992 |
| EP | 0 484 027 | 5/1992 |
| JP | 02142824 | 5/1990 |
| JP | 02173150 A | 7/1990 |
| JP | 2763612 B2 | 4/1991 |
| JP | 03095183 A | 4/1991 |
| JP | 05247081 A | 9/1993 |
| SU | 1 553 537 A1 | 3/1990 |
| SU | 1 684 289 A | 10/1991 |
| WO | WO 84/02069 | 6/1984 |
| WO | WO 88/06175 | 8/1988 |
| WO | WO 91/09861 | 7/1991 |
| WO | WO 91/14456 | 10/1991 |
| WO | WO 91/15243 | 10/1991 |
| WO | WO 91/18007 | 11/1991 |
| WO | WO 91/18630 | 12/1991 |
| WO | WO 94/04507 | 3/1994 |
| WO | WO 94/04614 | 3/1994 |
| WO | WO 94/09003 | 4/1994 |
| WO | WO 95/05818 | 3/1995 |
| WO | WO 95/29702 | 11/1995 |
| WO | WO 95/29915 | 11/1995 |
| WO | WO 95/29916 | 11/1995 |
| WO | WO 96/40223 | 12/1996 |
| WO | WO 97/15661 | 5/1997 |
| WO | WO 97/20846 | 5/1997 |
| WO | WO 97/27049 | 7/1997 |
| WO | WO 9729044 | 8/1997 |
| WO | WO 98/01156 | 1/1998 |
| WO | WO 98/25610 | 6/1998 |
| WO | WO 91/18006 | 11/1998 |

OTHER PUBLICATIONS

Bonnett, et al., "Hydroporphyrins of the meso–tetra(hydroxyphenyl)porphyrin series as tumour photosensitizers," *Biochem J* 261(1):277–80 (1989).

Brasklavksy, et al., "Photophysical properties of porphycene derivatives (18p porphyrinoids). J. Photochem. Photobiol. B: Biol. 40, 191–198," *J Photochem and Photobiol B: Biology* 40:191–198 (1997).

Buchler, et al., "Cerium(IV) sandwich complexes with porphyrin ligands linked by alipatic and quinone–containing bridges," *Chem. Berichte* 129(9):1073–1081 (1996).

Chambrier, et al., "Synthesis and Characterisation of Functionalised Phthalocyanine Compounds for Fabrication of Self–Assembled Monolayers," *Synthesis* 1283–1286 (1995).

Dietl, et al., "Synthesis and electrochemical investigations of molecular architectures involving C60 and tetraphenylporphyrin as building blocks," *J Chem Soc., Perkin Trans II* 1357–1364 (1998).

Garbo, "Purpurins and benzochlorins as sensitizers for photodynamic therapy," *J Photochem and Photobiol B: Biology* 34:109–116 (1996).

Godziela, et al., "Solution Characterization of Copper (II) and Silver (II) Porphyrins and the One–Electron Oxidation Products by Nuclear Magnetic Resonance Spectroscopy," *J Am Chem Soc* 108(9):2237–2243 (1986).

James, et al., "Potency and selective toxicity of tetra(hydroxyphenyl)– and tetrakis(dihydroxyphenyl)porphyrins in human melanoma cells, with and without exposure to red light," *Photochem Photobiol* 59(4):441–7 (1994).

Johnstone, et al., "Improved Syntheses of 5,10,15,20–Tetrakisaryl– and Tetrakisalkylporphyrins," *Heterocylces* 43(7):1423–1437 (1996).

Latouche, et al., "Synthesi of porphyrins with pendant arms; Participation of the ancillary ligands to the complexation process in proteic medium," *Tetrahedron Letters* 36(10):1665–1666 (1995).

Lin, "Photodynamic therapy of malignant tumors–recent developments," *Cancer Cells* 3(11):437–444 (1991).

Lindsey, et al., "Rothemund and Adler–Longo reactions revisited: Synthesis of tetraphenylporphyrins under equilibrium conditions," *J Org Chem* 52(5):827–836 (1987).

Little, "The Synthesis of covalently linked tetraarylporphyrin dimers," *J Heterocyclic Chem* 15(2):203–208 (1978).

Little, et al., "The Synthesis of Some Substituted Tetraarylporphyrins," *J Heterocyclic Chem.* 12: 343–349 (1975).

Manka, et al., "Template–driven self–assembly of a porphyrin–containing supramolecular complex," *J Am Chem Soc* 112(6):2440–2442 (1990).

Mehta, "Synthesis and nuclease activity of some 'porphyrin–acridone' hybrid molecules," *J Chem Soc, Perkin Trans I* 2667–2669 (1993).

Mehta, et al., "Porphyrin–anthraquinone hybrids: wavelength dependent DNA photonucleases," *Tetrahedron Letters* 38(40):7125–7128 (1997).

Mehta, et al., "Porphyrin–chlorambucil conjugates: Synthesis and light–induced nuclease activity," *Tetrahedron Letters* 35(24):4201–4204 (1994).

Milgrom, "Synthesis of some new tetra–arylporphyrins for studies in solar energy conversion," *J Chem Soc, Perkin Trans I* 2535–2539 (1983).

Rossbroich, et al., "Thermal–Lensing Measurements of Singlet Molecular Oxygen: Quantum Yields of Formation and Lifetimes," *Journal of Photochemistry* 31: 37–47 (1985).

Schneider, et al., "DNA Interactions with porphyrins bearing ammonium side chains," *J Org Chem* 59(24):7473–7478 (1994).

Shroyer, et al., "Steric Effects of Meta Substituents in Substituents Tetraphenylporphin Complexes of Ruthenium, Indium, Titanium, and Gallium," *J. Org. Chem.* 45(22):4296–4302 (1980).

Syrbu, et al., "Synthesis of tetraphenylporphines with active groups in the phenyl rings. 4_*functionally substituted monohydroxy derivatives of tetraphenylporphine," *Chemistry of Heterocyclic Compounds* (Engl. Transl.) 23:645–650 (1987).

Syrbu, et al., "Synthesis of tetraphenylporphines with active groups in the phenyl rings. 5.* Tetra(carboxymethylenoxyphenyl) porphines and their ethyl esters," *Chemistry of Heterocyclic Compounds* (Engl. Transl.) 25:1149–1153 (1989).

Zhamkochyan, et al., "Synthesis of new unsaturated mesotetraarylporphyrins," *Chemistry of Heterocyclic Compounds* (Engl. Transl.) 23:186–191 (1987).

PORPHYRIN DERIVATIVES THEIR USE IN PHOTODYNAMIC THERAPY AND MEDICAL DEVICES CONTAINING THEM

Priority is claimed under 35 U.S.C. §119 to PCT/GB99/02864, filed Aug. 31, 1999, which claims priority to application No. 9818789.1 filed in the United Kingdom on Aug. 28, 1998, and application No. 9912971.0 filed in the United Kingdom on Jun. 4, 1999.

FIELD OF THE INVENTION

The present invention relates to compounds, compositions, apparatus and methods for treating a medical condition for which a photodynamic compound is indicated, particularly in the curative or prophylactic treatment of medical conditions such as atherosclerosis, cataracts, restenosis, secondary cataracts, endometrial ablation, bladder cancer, other cancers and proliferative diseases, inflammation and infection.

Photodynamic therapy is a method of treating a diseased tissue of a patient. Typically, the surgical procedure involves administering a photodynamic agent to a patient, such as via an intravenous injection, and then irradiating the target diseased tissue with a separate light source. The photodynamic agent following irradiation with light emits reactive oxygen species, such as singlet oxygen, which disrupt the surrounding cellular tissue.

A problem with prior art methods is that many of the photodynamic agents are relatively insoluble in physiologically acceptable media and they also tend to form aggregates in solution. Such adverse physicochemical properties necessitate complex formulations in order to provide useful materials for medical use. Moreover, as the formulations are typically administered by intravenous injection it is difficult to target the diseased tissue specifically.

*Chemistry of Heterocyclic Compounds* 23, 186–191 (1987) (Zhamkochyan el al.) disclose s various 5,10,15,20-tetra(4'-vinyl and -allyl phenyl)porphyrin derivatives and their Cu(II), Ni(II), CO(II) and Fe(III)Cl complexes.

*Chemistry of Heterocyclic Compounds* 23, 645–50 (1987) (Syrbu et al.) discloses monohaloalkyloxyphenyl-triphenyl-porphyrins and dimeric porphyrins.

*Chemistry of Heterocyclic Compounds* 25, 1149–53 (1989) (Syrbu et al.) discloses tetra-(carboxymethylenoxy-phenyl)porphines and their ethyl esters.

*Chem. Ber.* 129(9), 1073–81 (1996) (Buchler et al.) discloses metalloporphyrin double deckers formed by reaction of 5-(4-hydroxyphenyl)-10,15,20-tris(4-methyl) phenylporphyrin with α,ωdibromoalkanes and 1,4-bis(3-bromopropyl)-2,5-dimethoxybenzene.

*J.A.C.S.* 112(6), 2440–2 (1990) (Manka et al.) discloses a tetraaminooxyphenylporphyrin derivative.

*J. Chem. Soc., Perkin Trans. I* no. 10, 2335–9 (1983) (Milgrom et al.) discloses 5,10,15,20-tetrakis(4-substituted phenoxy)porphyrin derivatives and their metal complexes for use as sensitisers for microheterogeneous water photo-oxidation.

*J. Org. Chem.* 59(24), 7473–8 (1994) (Schneider et al.) discloses 5,10,15,20-tetrakis(4-substituted phenoxy) porphyrin derivatives and their Cu and Zn complexes for potential use as antiviral/antitumour agents.

*J. Org. Chem.* 52(5), 827–36 (1987) (Lindsey et al) discloses the preparation of tetraphenylporphyrins.

*Tet. Letts.* 38(40), 7125 (1997) (Mehta et al.) discloses an anthraquinone porphyrin derivative for photodynamic therapy.

*Tet Letts.* 36(10), 1665–6 (1995) (Latouche et al.) discloses 5,10,15,20-tetrakis(4-(carboxymethylene)phenoxy) porphyrin derivatives and copper complexes in "proteic medium".

*J. Chem. Soc., Perkin Trans. I* no 22, 2667–9 (1993) (Mehta et al.) Discolors an acridone porphyrin derivative for photodynamic therapy.

*Tet. Letts.* 35(24), 4201–4 (1994) (Mehta et al.) discloses a porphyrin derivative linked to the anti-cancer drug chlorambucil for photodynamic therapy.

*J. Heterocyclic Chem.* 15(2), 203–8 (1978) (Little et al.) discloses covalently linked porphyrin dimers which may include a metal, such as V(IV) or Cu(II).

U.S. Pat. No. 5,594,136 relates to texaphyrins supported on a matrix. The matrix-supported texaphyrins may be used in the separation of neutral and anionic species, in applications concerning phosphate ester hydrolysis, magnetic resonance imaging and photodynamic therapy.

U.S. Pat. No. 5,284,647 relates to meso-tetraphenyl-porphyrin compounds which have a maximum of two substituents on the phenyl rings.

The present invention therefore seeks to provide improved compounds, compositions, apparatus and methods for treating a medical condition where photodynamic therapy is indicated and open the way for medical conditions which are not currently treated by photodynamic therapy.

DISCLOSURE OF THE INVENTION

According to a first aspect of the invention, there is provided a compound of formula I,

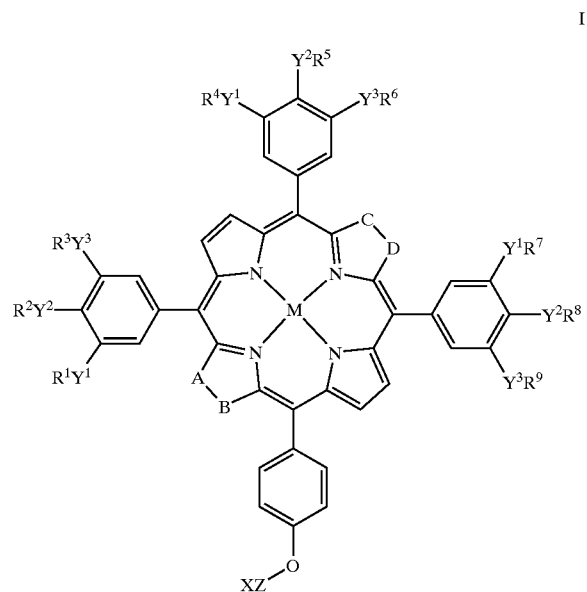

wherein $R^1$, $R^2$, $R^3$, $R^4$, $R^5$, $R^6$, $R^7$, $R^8$, and $R^9$ independently represent H, lower alkyl, lower alkenyl and lower alkynyl, the latter three of which are optionally substituted or terminated by one or more substituents selected from halo, cyano, nitro, lower alkyl, $OR^{10}$, $C(O)R^{11}$, $C(O)OR^{12}$, $C(O)NR^{13}R^{14}$ and $NR^{15}R^{16}$;

M represents a metallic element or a metalloid element;

X represents SH, S—]$_2$, OH, $NHR^{15}$, $CO_2H$, Cl, Br, I, NCO, NCS, CN, C≡CH, CH=CH$_2$, MgCl, ZnCl, Li, $Si(OR^{17})_3$, $SiR^{18}(OR^{17})_2$, $SiR^{18}R^{19}(OR^{17})$, Sihalo$_3$, Sihalo$_2$R$^{17}$, SihaloR$^{17}$R$^{18}$, silyl, NO$_2$, CHO C(O)]$_2$O, C(O)halo, C(O)OR$^{20}$, OC(O)halo, C(O)N$_3$, thiocyano, or halobenzyl;

Each Y$^1$, Y$^2$ and Y$^3$ is independently absent or represents O;

Z is absent or represents lower alkylene;

R$^{10}$, R$^{11}$, R$^{12}$, R$^{13}$, R$^{14}$, and R$^{16}$ independently represent H or lower alkyl;

R$^{15}$ represents H, lower alkyl, aryl or lower alkylaryl;

R$^{17}$, R$^{18}$ and R$^{19}$ independently represent H, lower alkyl, aryl or lower alkylaryl;

R$^{20}$ represents H, lower alkyl, lower alkenyl or C(O)R$^{21}$ where R$^{21}$ represents an activating group for reaction to form an amide bond such as N-hydroxysuccinimide, N-hydroxybenzotriazole, or pentafluorophenyl ester; and A–B and C–D independently represent CH=CH or C$_2$—CH$_2$;

which compounds or a pharmaceutically acceptable derivative thereof are referred to together hereinafter as "the compounds of the invention".

The term lower alkyl is intended to include linear or branched, cyclic or acyclic, C$_1$–C$_{20}$ alkyl which may be interrupted by oxygen (preferably no more than five oxygen atoms are present in each alkyl chain). Lower alkyl groups which R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{22}$ and R$^{23}$ may represent include C$_1$–C$_{18}$ alkyl, C$_1$–C$_{17}$ alkyl, C$_1$–C$_{16}$ alkyl, C$_1$–C$_{15}$ alkyl, C$_2$–C$_{15}$ alkyl, C$_3$–C$_{15}$ alkyl, C$_4$–C$_{15}$ alkyl, C$_5$–C$_{15}$ alkyl, C$_6$–C$_{15}$ alkyl, C$_7$–C$_{15}$ alkyl, C$_8$–C$_{15}$ alkyl, C$_8$–C$_{14}$ alkyl, C$_8$–C$_{12}$ alkyl and C$_8$–C$_{10}$ alkyl. Preferred lower alkyl groups which R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{20}$ and R$^{23}$ may represent include C$_6$, C$_7$, C$_8$, C$_9$, C$_{10}$, C$_{11}$, C$_{12}$, C$_{13}$, C$_{14}$, C$_{15}$ and C$_{16}$ alkyl. Preferred lower alkyl groups which, R$^{17}$, R$^{18}$ and R$^{19}$ may represent include C$_1$–C$_3$ alkyl, especially methyl or ethyl.

The terms lower alkenyl and lower alkynyl are intended to include linear or branched, cyclic or acyclic, C$_2$–C$_{20}$ alkenyl and C$_2$–C$_{20}$ alkynyl, respectively, each of which may be interrupted by oxygen (preferably no more than five oxygen atoms are present in each alkenyl or alkynyl chain). The term lower alkenyl also includes both the cis and trans geometric isomers. Lower alkenyl groups which R$^1$, R$^2$, R$^3$, R$^4$, R$^5$, R$^6$, R$^7$, R$^8$, R$^9$, R$^{20}$ and R$^{23}$ may represent include C$_2$–C$_{18}$ alkenyl, C$_2$–C$_{17}$ alkenyl, C$_2$–C$^{16}$ alkenyl, C$_2$–C$_{15}$ alkenyl, C$_3$–C$_{15}$ alkenyl, C$_4$–C$_{15}$ alkenyl, C$_5$–C$_{15}$ alkenyl, C$_6$–C$_{15}$ alkenyl, C$_7$–C$_{15}$ alkenyl, C$_8$–C$_{15}$ alkenyl, C$_8$–C$_{13}$ alkenyl and C$_8$–C$_{12}$ alkenyl, C$_8$–C$_{10}$ alkenyl. Preferred lower alkenyl groups which R$^1$, R$^2$, R$^3$, R$^4$, R$^5$, R$^6$, R$^7$, R$^8$, R$^9$, R$^{20}$, and R$^{23}$ may represent include C$_6$, C$_7$, C$_8$, C$_9$, C$_{10}$, C$_{11}$, C$_{12}$, C$_{13}$ and C$_{14}$ alkenyl, especially C$_{10}$ alkenyl.

Lower alkynyl groups which R$^1$, R$^2$, R$^3$, R$^4$, R$^5$, R$^6$, R$^7$, R$^8$, R$^9$, R$^{20}$ and R$^{23}$ may represent include C$_2$–C$_{18}$ alkynyl, C$_2$–C$_{17}$ alkynyl, C$_2$–C$_{16}$ alkynyl, C$_2$–C$_{15}$ alkynyl, C$_2$–C$_{14}$ alkynyl, C$_3$–C$_{15}$ alkynyl, C$_4$–C$_{15}$ alkynyl, C$_5$–C$_{15}$ alkynyl, C$_6$–C$_{15}$ alkynyl, C$_7$–C$_{15}$ alkynyl, C$_8$–C$_{15}$ alkynyl, C$_8$–C$_{14}$ alkynyl, C$_8$–C$_{13}$ alkynyl, C$_8$–C$_{12}$ alkynyl and C$_8$–C$_{10}$ alkynyl. Preferred lower alkynyl groups which R$^1$, R$^2$, R$^3$, R$^4$, R$^5$, R$^6$, R$^7$, R$^8$, R$^9$, R$^{20}$ and R$^{23}$ may represent include C$_6$, C$_7$, C$_8$, C$_9$, C$_{10}$, C$_{11}$, C$_{12}$, C$_{13}$ and C$_{14}$ alkynyl, especially C$_{10}$ alkynyl.

The term lower alkylene also includes linear or branched C$_1$ to C$_{20}$ alkylene which may be interrupted by oxygen (preferably no more than five oxygen atoms are present in each alkenyl chain). Preferred lower alkylene groups which Z, V and S may represent include C$_2$–C$_{20}$ alkylene, C$_4$–C$_{20}$ alkylene, C$_4$–C$_{18}$ alkylene, C$_4$–C$_{16}$ alkylene, C$_5$–C$_{16}$ alkylene, C$_6$–C$_{16}$ alkylene, C$_7$–C$_{16}$ alkylene, C$_8$–C$_{16}$ alkylene, C$_9$–C$_{16}$ alklylene, C$_{10}$–C$_{16}$ alkylene, C$_{12}$–C$_{16}$ alkylene and C$_{14}$–C$_{16}$ alkylene. Preferably, lower alkylene represents an alkylene having an even number of carbon atoms, for example C$_2$, C$_4$, C$_6$, C$_8$, C$_{10}$, C$_{12}$, C$_{14}$, C$_{16}$, C$_{18}$ and C$_{20}$ alkylene, especially C$_6$, C$_{10}$, C$_{12}$, C$_{14}$, C$_{16}$ and C$_{20}$ alkylene.

The term "aryl" includes six to ten-membered carbocyclic aromatic groups, such as phenyl and naphthyl, which groups are optionally substituted by one or more substituents selected from halo, cyano, nitro, lower alkyl, OR$^{10}$, C(O)R$^{11}$, C(O)OR$^{12}$, C(O)NR$^{13}$R$^{14}$ and NR$^{15}$R$^{16}$.

Halo groups which U and X may represent or include and with which R$^1$, R$^2$, R$^3$, R$^4$, R$^5$, R$^6$, R$^7$, R$^8$, R$^9$ and M may optionally be substituted or terminated, include fluoro, chloro, bromo and iodo.

The term "metallic element" is intended to include a divalent or trivalent metallic element. Preferably, the metallic element is diamagnetic. More preferably, the metallic element is selected from Zn (II), Cu (II), La (III), Lu (III), Y (III), In (III) Cd (II), Mg (II), Al(III) and Ru. Most preferably, the metallic element is Zn (II) or Mg (II).

The term "metalloid" is intended to include an element having physical and chemical properties, such as the ability to conduct electricity, that are intermediate to those of both metals and non-metals. The term metalloid element includes silicon (Si) and germanium (Ge) atoms which are optionally substituted with one or more ligands.

It will be appreciated that the terms metallic element and metalloid element include a metal element or a metalloid element having a positive oxidation state, all of which may be substituted by one or more ligands selected from halo, OH, OR$^{23}$ wherein R$^{23}$ is lower alkyl, lower alkenyl, lower alkynyl, aryl or alkylaryl as defined above.

For the avoidance of doubt, the term when X represents "S—]$_2$" means the disulphide dimer, for example the disulphide dimer of the compound of formula I or the disulphide dimer of a photosensitizable compound as defined hereinafter. The compound of formula I or the photosensitizable compound is then bonded through the sulphur atom to an insoluble support thus forming a thio ether or a disulphide linkage.

The term when X represents "C(O)]$_2$O" means the anhydride, for example the anhydride of the compound of formula I, the anhydride of an insoluble support or an anhydride of a photosensitizable compound as defined hereinafter.

Preferred compounds of the invention include those in which each Y$^1$, Y$^2$ and Y$^3$ represents oxygen, or each Y$^1$, and Y$^3$ represents oxygen and each Y$^2$ is absent.

Further preferred compounds of the invention include those in which one or more of R$^1$, R$^2$, R$^3$, R$^4$, R$^5$, R$^6$, R$^7$, R$^8$ and R$^9$ (preferably all) represent lower alkyl and each Y$^1$, Y$^2$ and Y$^3$ represents oxygen, or each Y$^1$ and Y$^3$ represents oxygen and each Y$^2$ is absent and one or more of R$^1$, R$^3$, R$^4$, R$^6$, R$^7$ and R$^9$ (preferably all) represent lower alkyl and R$^2$, R$^5$ and R$^8$ (preferably all) represent H.

Further preferred compounds of the invention include those wherein X represents SH, S—]$_2$, OH, CH=CH$_2$, C≡CH, CO$_2$H, NHR$^{15}$, halo, C(O)halo, C(O)OR$^{20}$, silyl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, wherein R$^{17}$ is lower alkyl, preferably methyl or ethyl.

Preferred compounds of the invention include those wherein:

R$^1$, R$^2$, R$^3$, R$^4$, R$^5$, R$^6$, R$^7$, R$^8$ and R$^9$ independently represent H or lower alkyl;

M represents a metallic element, a silicon atom, or a germanium atom;

Each $Y^1$, $Y^2$ and $Y^3$ represents oxygen, or each $Y^1$ and $Y^3$ represents oxygen and each $Y^2$ is absent; and Z is absent or represents lower alkylene.

More preferred compounds of the invention include those wherein:

$R^1$, $R^2$, $R^3$, $R^4$, $R^5$, $R^6$, $R^7$, $R^8$ and $R^9$ independently represent linear or branched, cyclic or acyclic, $C_6$–$C_{16}$ alkyl and each $Y^1$, $Y^2$ and $Y^3$ represents oxygen; or $R^1$, $R^3$, $R^4$, $R^6$, $R^7$ and $R^9$ independently represent linear or branched, cyclic or acyclic, $C_6$–$C_{16}$ alkyl, $R^2$, $R^5$ and $R^8$ represent H, each $Y^1$ and $Y^3$ represents oxygen and each $Y^2$ is absent;

M represents Zn (II), La (III), Lu (III), Y (III), In (III), Cd (II), Mg (II), Al (III), Ru, a silicon atom or a germanium atom;

X represents SH, S—]$_2$, CH=CH$_2$, C≡CH, OH, CO$_2$H, NHR$^{15}$, halo, Si(OR$^{17}$)$_3$, SiR$^{18}$(OR$^{17}$)$_2$, SiR$^{18}$R$^{19}$ (OR$^{17}$), Sihalo$_3$, Sihalo$_2$R$^{17}$, SihaloR$^{17}$R$^{18}$, wherein R$^{17}$ represents methyl or ethyl; and Z represents lower alkylene having an even number of carbon atoms.

Particularly preferred compounds of the invention include those wherein $R^1$, $R^2$, $R^3$, $R^4$, $R^5$, $R^6$, $R^7$, $R^8$ and $R^9$ independently represent, n-$C_6H_{13}$, n-$C_8H_{17}$, n-$C_{10}H_{21}$, n-$C_{12}H_{25}$, n-$C_{14}H_{29}$, or n-$C_{16}H_{33}$ and each $Y^1$, $Y^2$ and $Y^3$ represents oxygen; or $R^1$, $R^3$, $R^4$, $R^6$, $R^7$ and $R^9$ independently represent n-$C_6H_{13}$, n-$C_8H_{17}$, n-$C_{10}OH_{21}$, n-$C_{12}H_{25}$, n-$C_{14}H_{29}$, or n-$C_{16}H_{33}$, $R^2$, $R^5$ and $R^8$ represent H, each $Y^1$ and $Y^3$ represents oxygen and each $Y^2$ is absent;

M represents Zn (II) or Mg (II);

X represents SH, S—]$_2$, CH=CH$_2$, C≡CH, OH, CO$_2$H, NHR$^{15}$, halo, Si(OR$^{17}$)$_3$, SiR$^{18}$(OR$^{17}$)$_2$, SiR$^{18}$R$^{19}$ (OR$^{17}$), Sihalo$_3$, Sihalo$_2$R$^{17}$, SihaloR$^{17}$R$^{18}$, wherein R$^{17}$ represents methyl or ethyl; and Z represents n-$C_6H_{12}$, n-$C_8H_{16}$, n-$C_{10}H_{20}$, n-$C_{12}H_{24}$, n-$C_{14}H_{28}$, n-$C_{16}H_{32}$, n-$C_{18}H_{36}$, or n-$C_{20}H_{40}$, each of which groups are optionally interrupted by oxygen.

Most preferred compounds of the invention include those wherein:

$R^1$, $R^2$, $R^1$, $R^4$, $R^5$, $R^6$, $R^7$, $R^8$ and $R^9$ represent n-$C_6H_{13}$, n-$CH_{10}H_{21}$ or n-$C_{16}H_{33}$ and each $Y^1$, $Y^2$ and $Y^3$ represents oxygen; or $R^1$, $R^3$, $R^4$, $R^6$, $R^7$ and $R^9$ independently represent n-$C_6H_{13}$, n-$C_{10}H_{21}$ or n-$C_{16}H_{33}$, $R^2$, $R^5$ and $R^8$ represent H, each $Y^1$ and $Y^3$ represents oxygen and each $Y^2$ is absent;

M represents Zn (II) or Mg (II);

X represents SH, S—]$_2$, CH=CH$_2$ or Si (halo)$_3$; and

Z represents n-$C_6H_{12}$, n-$C_{10}H_{20}$, n-$C_{12}H_{24}$, n-$C_{16}H_{32}$, (CH$_2$)$_{12}$—(CH$_2$)$_2$ (CH$_2$)$_6$—O—(CH$_2$)$_2$ or (CH$_2$)$_{16}$—O—(CH$_2$)$_2$.

Most preferred compounds of the invention include the compounds of Examples 67 to 81 described hereinafter.

According to the invention there is also provided a process for the preparation of the compound of formula I, when A–B represents CH$_2$—CH$_2$ and C–D represents CH=CH or A–B represents CH=CH and C–D represents CH$_2$—CH$_2$, which comprises the reduction of a compound of formula I wherein $R^1$, $R^2$, $R^3$, $R^4$, $R^5$, $R^6$, $R^7$, $R^8$, $R^9$, M, X, $Y^1$, $Y^2$, $Y^3$ and Z are as defined in formula I and A–B and C–D represent CH=CH.

The reduction may be accomplished using methods which are well known to those skilled in the art. For example, the reduction may be accomplished with a mixture of potassium hydroxide, an aryl sulphonylhydrazide, such as p-toluenesulphonylhydrazide, and pyridine at a temperature of between 80° C. to 110° C., preferably a temperature of 100° C. to 105° C. (R Bonnett et al., *Biochem J*. (1989) 261, p277–280).

An alternative synthetic route to the compounds of formula I, when A–B and C–D represent CH=CH, comprises the reaction of a compound of formula II:

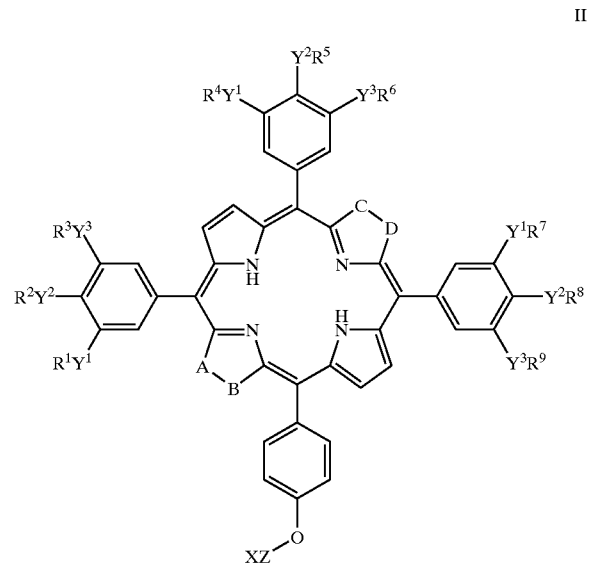

II wherein $R^1$, $R^2$, $R^3$, $R^4$, $R^5$, $R^6$, $R^7$, $R^8$, $R^9$, X, $Y^1$, $Y^2$, $Y^3$ and Z are as previously defined for formula I, A–B and C–D represent CH=CH, with a metallic element M or a metalloid element M as previously defined for a compound of formula I.

Typically, the reaction is performed using an appropriate metal salt, such as magnesium perchlorate or zinc acetate, in a suitable solvent (E Dietel et al, *Journal of the Chemical Society, Perkin Transactions. II*, 1998, p 1357 to 1364. For example, when the metallic element is Zn the reaction may be performed using an anhydrous zinc salt such as Zn(OAc)$_2$ or ZnCl$_2$ in anhydrous tetrahydrofuran at reflux temperature of the reaction.

A further alternative synthetic route to the compounds of formula I, when A–B and C–D both represent CH$_2$—CH$_2$, involves reducing a compound of formula II wherein $R^1$, $R^2$, $R^3$, $R^4$, $R^1$, $R^6$, $R^7$, $R^8$, $R^9$, X, $Y^1$, $Y^2$, $Y^3$ and Z are as defined above, A–B and C–D represent CH=CH, and reacting the resultant reduced form of compound II with a metallic element M or a metalloid element M as previously defined.

A still yet further alternative synthetic route to the compounds of formula I, when A–B represents CH$_2$—CH$_2$ and C–D represents CH=CH, or A–B represents CH=CH and C–D represents CH$_2$—CH$_2$, involves reducing a compound of formula II wherein $R^1$, $R^2$, $R^3$, $R^4$, $R^5$, $R^6$, $R^7$, $R^8$, $R^9$, X, $Y^1$, $Y^2$, $Y^3$ and Z are as defined above, A–B and C–D represent CH=CH, and reacting the resultant reduced form of compound II with a metallic element M or a metalloid element M as previously defined.

A compound of formula II may be prepared by conversion of the Z—F functional group of a compound of formula III:

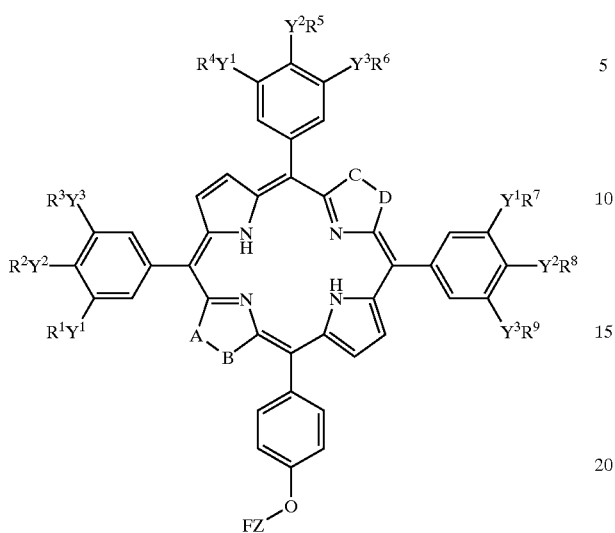

III wherein $R^1$, $R^2$, $R^3$, $R^4$, $R^5$, $R^6$, $R^7$, $R^8$, $R^9$, $Y^1$, $Y^2$, $Y^3$, Z, A–B and C–D are as previously defined for formula II, and F represents OH or a lower alkylene-CH=CH$_2$ group, into the desired ZX functional group, wherein X is as previously defined for formula II.

For example, when X is SH or S—]$_2$ in formula II, the reaction may be accomplished via formation of an isothiuronium salt, from a compound of formula III when F represents OH, using reagents and conditions which are well known to those skilled in the art (see I Chambrier et al., *Synthesis*, 1995, p1283 to 1286).

Typically, lie Z—OH alcohol functionality group of a compound of formula III is first derivatised into a Z-OSO$_2$R$^{22}$ group, wherein R$^{22}$ is lower alkyl or phenyl, both of which may be optionally substituted by one or more substituents selected from halo, cyano, nitro, lower alkyl, OR$^{10}$, C(O)R$^{11}$, C(O)OR$^{12}$, C(O)NR$^{13}$R$^{14}$ and NR$^{15}$R$^{16}$, using methods which are well known to those skilled in the art. For example, the Z—OH alcohol functionality compound of formula III may be mesylated by reaction with MeSO$_2$Cl in an appropriate solvent, such as dichloromethane, at a temperature of 10° C. to 30° C. The resultant mesylate group may then be displaced by reaction with thiourea to form an isothiouronium salt. Typically, the reaction is performed in THF/ethanol solvent mixture which has optionally been deoxygenated, under reflux in the dark, preferably under an inert atmosphere of nitrogen.

A compound of formula II when X represents SH may be prepared by the basic hydrolysis of the thiouronium salt in a THF/ethanol solvent mixture, for example using aqueous sodium hydroxide, under reflux and under an inert atmosphere, such as a nitrogen atmosphere.

A compound of formula II when X represents S—]$_2$ may be prepared by the basic hydrolysis of the thiouronium salt in a THF/ethanol solvent mixture, for example using aqueous sodium hydroxide, at reflux temperature of the reaction mixture under an oxygen atmosphere.

When X is CH=CH$_2$ in formula II and Z represents lower alkylene that is interrupted by oxygen, the reaction may be accomplished via conversion of the Z—OH alcohol functionality group of a compound of formula III into a Z—OSO$_2$R$^{22}$ group, wherein R$^{22}$ is as previously defined. For example, the Z—OH alcohol functionality of the compound of formula III may be mesylated by reaction with MeSO$_2$Cl. The resultant mesylate group may then be displaced by reaction with the appropriate alkenoate, for example sodium butenoate, in an appropriate organic solvent such as THF under reflux.

A compound of formula III may be prepared by reaction of four molar equivalents of pyrrole with one molar equivalent of a compound of formula V:

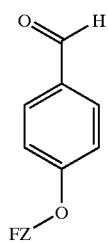

V wherein Z and F are as previously defined for a compound for formula III, and when F represents OH the alcohol functionality is optionally protected with a suitable protecting group, for example an acetyl group, using methods which are well known to those skilled in the art, and with one molar equivalent of each compounds of formulae VI, VII and VIII:

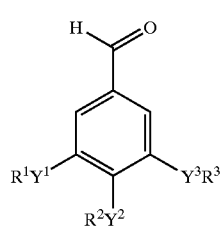

VI

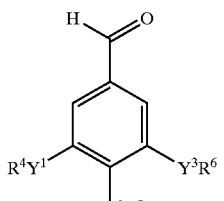

VII

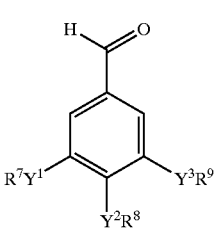

VIII wherein $R^1$, $R^2$, $R^3$, $R^4$, $R^5$, $R^6$, $R^7$, $R^8$, $R^9$, $Y^1$, $Y^2$, $Y^3$ are as previously defined for a compound of formula III.

It will be appreciated that when compounds of formula VI, VII and VIII are identical, the reaction is conducted with 3 molar equivalents of one of the compounds of formula VI, VII or VIII.

Preferably, the reaction is carried out under acidic conditions by methods known to those skilled in the art (R G Little et al, *Journal of Heterocyclic Chemistry*, 1975, Vol 12, p343). Typically, a mixture of one molar equivalent of a compound of formula V, VI, VII and VIII and four molar equivalents of pyrrole in an appropriate solvent, such as an organic acid for example propionic acid, optionally with the addition of a mineral acid such as hydrochloric, hydrobromic, hydroiodic, or sulphuric acid, optionally with the addition of a Lewis acid such as zinc chloride or aluminium trichloride, heated under reflux for 1 to 4 hours, preferably four hours.

The compounds of formula V, VI, VII and VIII and derivatives thereof, when neither commercially available nor subsequently described, may be obtained using conventional synthetic procedures in accordance with standard text books on organic chemistry or literature precedent, from readily accessible starting materials using appropriate reagents and reaction conditions.

For example, the compounds of formula V may be prepared from reaction of a compound of formula IX:

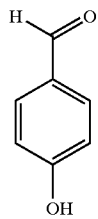

IX with a compound of formula F—Z—W, wherein Z and F are as previously defined for a compound of formula V, and W represents a leaving group, such as halo or W represents OH.

Typically, when W represents a leaving group such as halo the reaction is performed in a suitable organic solvent, such as methyl ethyl ketone or dichloromethane, under basic conditions, for example by using $K_2CO_3$, $Na_2CO_3$, pyridine or triethylamine, optionally at reflux temperature of the reaction mixture.

Typically, when W represents OH the reaction is performed in a suitable organic solvent such as dry tetrahydrofuran (THF) in the presence of triphenylphosphine and an azodicarboxylate, for example diisopropyl-azo dicarboxylate).

The compounds of formula VI, VII, and VIII may be prepared from reaction of a compound of formula X:

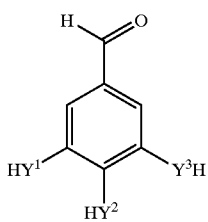

X wherein $Y^1$, $Y^2$ and $Y^3$ are as previously defined before for a compound of formula III, or a suitably mono- or di-protected phenol derivative thereof, with a compound of formula $R^1W$, $R^2W$, $R^3W$, $R^4W$, $R^5W$, $R^6W$, $R^7W$, $R^8W$ or $R^9W$ wherein $R^1$, $R^2$, $R^3$, $R^4$, $R^5$, $R^6$, $R^7$, $R^8$ and $R^9$ are as previously defined for a compound of formulae VI, VII and VIII, respectively, and W is a leaving group, such as halo.

Typically, the reaction is performed in a suitable organic solvent, such as methyl ethyl ketone or dichloromethane, under basic conditions, for example by using $K_2CO_3$, $Na_2CO_3$, pyridine or triethylamine, optionally at reflux temperature of the reaction mixture.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

It will also be appreciated that various standard substituent or functional group interconversions and transformations within certain compounds of formula I will provide other compounds of formula I.

In a further aspect, the present invention provides a composition comprising an insoluble support and a compound of the invention of formula I. Preferably, the insoluble support is also biocompatible.

By the term "insoluble" we mean that the support does not dissolve or decompose in aqueous solution under normal physiological conditions over the intended timescale for photodynamic ability (ie reactive oxygen species production) of the photosensitizable compound. The timescale would be relatively short for an insertable/removable medical device for example 1 to 180 minutes, or many years for semi-permanent or permanent implanted medical devices. In other words, we mean that the support does not dissolve or decompose when implanted in or administered to a human or animal, during the desired period of treatment. By the term "biocompatible" we mean that the support is in a form that does not produce an adverse, allergic or other untoward reaction when administered to a human or animal in accordance with the invention.

The insoluble support enables the composition of the invention to be administered to a patient directly to the disease site without the need for administration by injection. This avoids the necessity for the photosensitizable compound to reach and accumulate at the target site, as is necessary with conventional photodynamic therapy, because the device is applied directly to the target site. Furthermore, the insoluble support eliminates or substantially reduces the dispersal and accumulation of the photosensitizable, compound in non-target tissues, thereby minimising chemical toxicity and damage to healthy non-target tissue following irradiation with light of the appropriate wavelength or indeed from activation by sunlight and other environmental light sources. Moreover, unless deliberately left in the body, when the support is subsequently withdrawn, no compound of the invention is left in the body.

Preferably, the solid support comprises polyethylene; polypropylene; polystyrene; polyacrylamide; polyamide; a resin for solid phase oligopeptide and/or oligonucleotide synthesis, such as a Merrifield resin; a natural or synthetic polysaccharide; a silicon derivative such as a functionalised silica, a glass, a silicone or a silicone rubber; an alumina; a noble metal, preferably a gold film optionally mounted on a glass surface; or a porous solid such as a controlled pore glass, a gel permeation material or a zeolite.

The insoluble support may be flexible, such as a flexible membrane, or a rigid support. Preferably, the insoluble support is coated and/or impregnated with the photosensitizable compound. More preferably, the photosensitizable compound is fixed to the surface of the insoluble support, optionally via a covalent bond, and optionally includes a bifunctional spacer molecule to space the compound from die insoluble support.

A compound fixed to the surface of the insoluble support may be represented by formula XI:

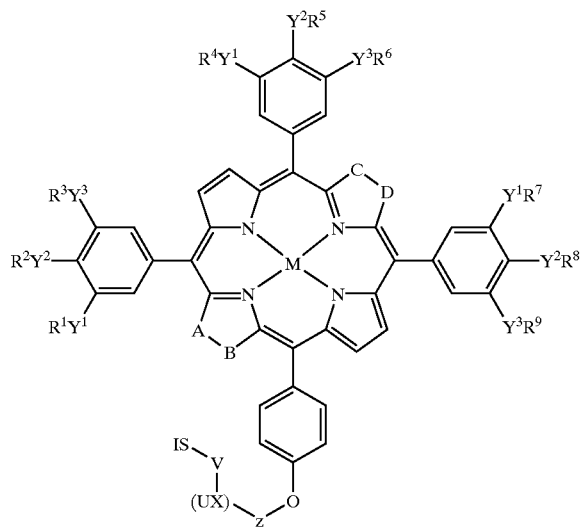

XI

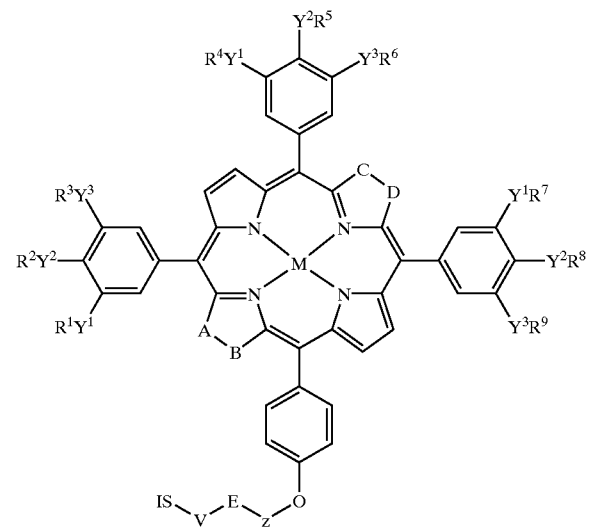

XII wherein $R^1$, $R^2$, $R^3$, $R^4$, $R^5$, $R^6$, $R^7$; $R^8$ and $R^9$, A–B, C–D, M, Z, $Y^1$, $Y^2$ and $Y^3$ are as previously defined for a compound of formula I; V is absent or represents lower alkylene or an alkylaryl group; IS represents the insoluble support; (UX) represents a linkage derived from reaction between a group X of a compound of the invention of formula I and a group U of the insoluble support, wherein X is as defined for a compound of formula I, and U represents the group on the insoluble support for bonding with X, namely U represents OH, $NHR^{15}$, SH, $CO_2H$, Cl, Br, I, NCO, NCS, CN, C≡CH, CH=$CH_2$, MgCl, ZnCl, Li, $Si(OR^{17})_3$, $SIR^{18}(OR^{17})_2$, $SiR^{18}R^{19}(OR^{17})$, $Sihalo_3$, $Sihalo_2R^{17}$, $SihaloR^{17}R^{18}$, silyl, $NO_2$, CHO, $C(O)]_2O$, C(O)halo, $C(O)OR^{20}$, OC(O)halo, $C(O)N_3$, thiocyano or halobenzyl.

Preferably, the group X of the compound of the invention of formula I represents SH, S—$]_2$, CH=$CH_2$, halo, $C(O)]_2$ O, $C(O)OR^{20}$, C≡CH, $NHR^{15}$, Si $(halo)_3$ or OH.

Preferably, when the group X of the compound of formula I represents $CO_2R^{20}$ then the group U of the insoluble support represents $NHR^{15}$. Preferably, when the group X of the compound of formula I represents $NHR^{15}$ then the group U of the insoluble support represents $CO_2R^{20}$. Preferably, when the group X of the compound of formula I represents CH=$CH_2$ then the group U of the insoluble support represents CH=$CH_2$ or C≡CH, or alternatively the group U is absent and the photosensitizable compound is linked to the insoluble support by using a dopant such as acrylic acid. Preferably, when the group X of the compound of formula I represents OH then the group U of the insoluble support represents $Si(OR^{17})_3$, $SIR^{18}(OR^{17})_2$, $SiR^{18}R^{19}(OR^{17})$, $Sihalo_3$, $Sihalo_2R^{17}$, or $SihaloR^{17}R^{18}$. Preferably, when the group X of the compound of formula I represents SH or S—$]_2$ then the insoluble support includes a noble metal. Preferably, when the group X of the compound of formula I represents C≡CH then the group U of the insoluble support represents Cl, Br, I, C≡CH, CH=$CH_2$, MgCl or ZnCl, or the group U is absent and the compound of formula I is linked to the insoluble support by using a dopant such as acrylic acid.

It will be appreciated that a composition of formula XI may also be represented by a compound of formula XII.

wherein $R^1$, $R^2$, $R^3$, $R^4$, $R^5$, $R^6$, $R^7$, $R^8$, $R^9$, $Y^1$, $Y^2$, $Y^3$, Z, A–B, C–D and M are as previously defined for a compound of formula I, IS represents the insoluble support, V is absent or represents lower alkylene or an alkylaryl group; and E represents a linkage selected from an ether, thioether, ester, keto, poly(alkyloxy), amide, amine, carbamate, urea, —CH=CH—, —C≡C—, —$Si(OR^{17})_2$—, —$SiR^{18}R^{19}$—, —$SiR^{17}R^{18}$—, amino alcohol, amino acyl, alkylene, lower alkenyl, aryl or lower alkylaryl wherein $R^{17}$, $R^{18}$ and $R^{19}$ are as defined hereinbefore.

Preferably, E represents alkylene, ether, amide, silyloxy, alkynyl, alkenyl, thioether, $NR^{15}$, $(CH_2CH_2O)_m$, keto, ester, or phenyl wherein m represents 1 to 10 and $R^{15}$ is as previously defined hereinbefore.

According to a further aspect of the invention there is provided a process for the preparation of a composition of formula XII which comprises reacting a compound of the invention of formula I as previously defined with a compound of formula XIII:

XIII wherein IS, V and U are as defined above.

It will be appreciated that the X groups present on a compound of the invention react with available groups, termed U, present on or previously inserted into, the insoluble support. The combination of reactive groups U and X gives rise to the composition of the invention wherein the compound of the invention and the insoluble support are linked via a linkage such as ether, ester, amide, amine, carbamate, urea, —CH=CH—, keto, poly(alkyloxy), —C≡C—, —$Si(OR^{17})_2$—, $SiR^{18}R^{19}$—, —$SiR^{17}R^{18}$—, amino alcohol, aminoacyl, alkylene, lower alkenyl, aryl or lower alkylaryl.

It will be appreciated that the reactive U group of the insoluble support may be either initially present or introduced by semi-synthesis (for example from materials derived from natural sources) or by ab initio chemical synthesis.

The choice of reaction conditions to link a compound of formula XII with a compound of formula XIII will depend on the nature of the X and U groups. Such conditions are well known to those skilled in the art. For example, if both U and X independently represent CH=CH$_2$ or C≡CH then the composition may be formed using for example, free radical-induced polymerisation, by halogenating U and/or X, and using metal-mediated cross coupling or standard alkyne coupling chemistry (*Advanced Organic Chemistry*, J March, Wiley Interscience, 4$^{th}$ Edition, p449–463; p714–715; p194; and p744). Alternatively, or additionally, if X represents CH=CH$_2$ or C≡CH and the insoluble support is a polymeric compound having no complementary U groups, then the photosensitizable compound may be linked to the polymeric support by using a dopant, such as an acrylic acid. The dopant may be incorporated into the polymeric support to provide a binding site for the photosensitizable compound or the dopant may be bonded to the photosensitizable compound and the resultant compound copolymerized with the polymeric support.

Reagents such as carbodiimides, 1,1'-carbonyldiiaidazole, cyanuric chloride, chlorotriazine, cyanogen bromide and glutaraldehyde, and processes such as use of mixed anhydrides, reductive amination and metal-assisted cross-couplings of halogenated compounds with organometallic compounds may also be used to couple the photosensitizable compound to the insoluble support.

According to a further aspect of the invention, there is provided a composition for the in vivo delivery of a photosensitizable compound to a target tissue comprising a photosensitizable compound and a biocompatible insoluble support, wherein the photosensitizable compound comprises a macrocycle having at least four unsaturated five-membered nitrogen containing rings.

The term "unsaturated five-membered nitrogen containing ring" includes pyrrole, dihydropyrrole, pyrroline and isomers thereof.

Preferably, the photosensitizable compound comprises a benzoporphyrin, a porphycene, a purpurin, an etiopurpurin, a chlorophyll, an haematoporphyrin, a phorbine, a chlorphyrin, a verdin, a bacteriochlorin, a porphyrinogen, a phthalocyanine, or a mixture of any two or more of these, or a pharmaceutically acceptable derivative thereof.

Preferably, the photosensitizable compound is a porphycene, a purpurin, a chlorophyll, a phthalocyanine, or a benzoporphyrin or a derivative of any of these compounds. For example, each of the four unsaturated five-membered nitrogen containing rings of the purpurin may be independently substituted with a lower alkyl, preferably an ethyl group. Each of the phenyl rings of the phthalocyanine may independently include a sulphate, amino, nitro, hydroxy, or carboxyl group.

The composition of the present invention comprising a photosensitizable compound and the insoluble support is preferably a compound of formula XIV:

$$\text{IS---(UX)---PC} \qquad \text{XIV}$$

wherein PC represents a photosensitizable compound comprising a benzoporphyrin, a porphycene, a purpurin, an etiopurpurin, a chlorophyll, an haematoporphyrin, a phorbine, a chlorphyrin, a verdin, a bacteriochlorin, a porphyrinogen, a phthalocyanine, or a mixture thereof, IS represents the biocompatible insoluble support, (UX) represents a linkage derived from reaction between a group X of the photosensitizable compound and a group U of the insoluble support, wherein X represents NHR$^{15}$, OH, SH, S—]$_2$, CO$_2$H, Cl, Br, I, NCO, NCS, CN, C≡CH, CH=CH$_2$, MgCl, ZnCl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO, C(O)halo, C(O)OR$^{20}$, C(O)]$_2$O, OC(O)halo, C(O)N$_3$, thiocyano, or halobenzyl, and U represents NHR$_{15}$, OH, SH, CO$_2$H, Cl, Br, I, NCO, NCS, CN, C≡CH, CH=CH$_2$, MgCl, ZnCl, Si(OR$^{17}$)$_3$, SiR$_{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO, C(O)halo, C(O)OR$^{20}$, C(O)]$_2$O, OC(O)halo, C(O)N$_3$, thiocyano, or halobenzyl, wherein R$^{15}$, R$^{17}$, R$^{18}$ and R$^{19}$ are as previously defined for a compound of formula I, and R$^{20}$ represents H, lower alkyl, lower alkenyl or C(O)R$^{21}$ where R$^{21}$ represents an activating group for reaction to form an amide bond such as N-hydroxysuccinimide, N-hydroxybenzotriazole, or pentafluorophenyl ester.

It will be appreciated that the group X may be present in the photosensitizable compound per se, for example, a chlorophyll includes a group X representing CH=CH$_2$ and CO$_2$R$^{20}$ where R$^{20}$ represents lower alkenyl, or the group X may be introduced into the photosensitizable compound by ab initio chemical synthesis.

Preferably, the photosensitizable compound is a benzoporphyrin and the group X represents CO$_2$R$^{20}$ or CH=CH$_2$, a porphycene and the group X represents NHR$^{15}$ or CO$_2$R$^{20}$, a purpurin and the group X represents CO$_2$R$^{20}$ or CH=CH$_2$, a chlorophyll and the group X represents CO$_2$R$^{20}$ or CH=CH$_2$, an haematoporphyrin and the group X represents CO$_2$R$^{20}$, CH=CH$_2$ or OH, an etiopurpurin and the group X represents CO$_2$R$^{20}$, a phorbine and the group X represents CO$_2$R$^{20}$, CH=CH$_2$, OH or SH, a verdin and the group X represents CO$_2$R$^{20}$, a chlorphyrin and the group X represents C≡CH, a bacteriochlorin and the group X represents CO$_2$R$^{20}$, CH=CH$_2$ or SH, or a porphyrinogen and the group X represents CO$_2$R$^{20}$ CH=CH$_2$ or OH.

Preferably, when the group X of the photosensitizable compound represents CO$_2$R$^{20}$ then the group U of the insoluble support represents NHR$^{15}$. Preferably, when the group X of the photosensitizable compound represents NHR$^{15}$ then the group U of the insoluble support represents CO$_2$R$^{20}$. Preferably, when the group X of the photosensitizable compound represents CH=CH$_2$ then the group U of the insoluble support represents CH=CH$_2$ or C≡CH, or alternatively the group U is absent and the photosensitizable compound is linked to the insoluble support by using a dopant such as acrylic acid. Preferably, when the group X of the photosensitizable compound represents OH then the group U of the insoluble support represents Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, or SihaloR$^{17}$R$^{18}$. Preferably, when the group X of the photosensitizable compound represents SH or S—]$_2$ then the insoluble support includes a noble metal. Preferably when the group X of the photosensitizable compound represents C≡CH then the group U of the insoluble support represents Cl, Br, I, C≡CH, CH=CH$_2$, MgCl or ZnCl, or the group U is absent and the photosensitizable compound is linked to the insoluble support by using a dopant such as acrylic acid.

Preferably, the photosensitizable compound includes a spacer group S to which the X group is attached, wherein S represents lower alkylene or an alkylaryl group.

Preferably, the insoluble support includes a spacer group V to which the U group is attached, wherein V represents lower alkylene or an alkylaryl group.

Preferably the photosensitizable compound includes a metallic or a metalloid element bonded to a nitrogen atom, preferably to a pyrrole nitrogen atom, of the photosensitizable compound.

It will be appreciated that a composition of the present invention comprising a photosentizable compound and the insoluble support may also be represented by a compound of formula XV.

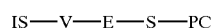

XV wherein IS and PC are as previously defined for a compound of formula XIV, V and S are both absent or independently represent lower alkylene or an alkylaryl group, and E represents a linkage selected from an ether, thioether, ester, keto, poly(alkyloxy), amide, amine, carbamate, urea, —CH═CH—, —C≡C—, —Si(OR$^{17}$)$_2$—, —SiR$^{18}$R$^{19}$—, —SiR$^{17}$R$^{18}$—, amino alcohol, amino acyl, alkylene, lower alkenyl, aryl or lower alkylaryl wherein R$^{17}$, R$^{18}$ and R$^{19}$ are as defined hereinbefore.

Preferably, E represents alkylene, ether, amide, silyloxy, alkynyl, alkenyl, thioether, NR$^{15}$, (CH$_2$CH$_2$O)$_m$, keto, ester, or phenyl, wherein m represents 1 to 10 and R$^{15}$ is as previously defined hereinbefore.

In yet a further aspect, the present invention provides a process for the preparation of the composition of the invention comprising a photosensitizable compound and the insoluble support, which is preferably a compound of formula XIV or XV, as defined hereinbefore.

Preferably, the insoluble support is coated and/or impregnated with the photosensitizable compound. More preferably, the photosensitizable compound is fixed to the surface of the insoluble support, optionally via a covalent bond and optionally includes a bifunctional spacer molecule to space the photosensitizable compound from the insoluble support.

Preferably, the process for the preparation of a composition of the present invention comprises reacting a compound of formula XVI:

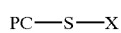

XVI wherein PC-S-X together represents the photosensitizable compound, X is as previously defined for a compound of formula XIV, PC represents a benzoporphyrin, a porphycene, a purpurin, an etiopurpurin, a chlorophyll, an haematoporphyrin, a phorbine, a chlorphyrin, a verdin, a bacteriochlorin, a porphyrinogen, a phthalocyanine, or a mixture of any two or more of these, and S is absent or represents lower alkylene or an alkylaryl group, with a compound of formula XVII:

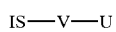

XVII wherein IS-V-U together represents the insoluble support, U is as previously defined for a compound of formula XIV and V is absent or represents lower alkylene or an alkylaryl group.

It will be appreciated that the X groups of the photosensitizable compound react with available groups, termed U, present on or previously inserted into, the insoluble support. The combination of reactive groups U and X gives rise to the composition of the invention wherein the photosensitizable compound and the insoluble support are linked via a linkage such as ether, ester, amide, amine, carbamate, urea, —CH═CH—, —C≡C—, keto, poly(alkyloxy), —Si (OR$^{17}$)$_2$—, SiR$^{18}$R$^{19}$—, —SiR$^{17}$R$^{18}$—, amino alcohol, amino acyl, alkylene, lower alkenyl, aryl or lower alkylaryl.

It will be appreciated that the reactive X group of the photosensitizable compound and the reactive U group of the insoluble support may be either initially present or introduced by semi-synthesis (for example from materials derived from natural sources) or by ab initio chemical synthesis.

The choice of reaction conditions to link a compound of formula XVI with a compound of formula XVII will depend on the nature of the X and U groups. Such conditions are well known to those skilled in the art. For example, if both U and X independently represent CH═CH$_2$ or C≡CH then the composition may be formed using for example, free radical-induced polymerisation, by halogenating U and/or X, and using metal-mediated cross coupling or standard alkyne coupling chemistry (Advanced Organic Chemistry, J March, Wiley Interscience, 4$^{th}$ Edition, p449–463; p714–715; p194; and p744). Alternatively, or additionally, if X represents CH═CH$_2$ or C≡CH and the insoluble support is a polymeric compound having no complementary U groups, then the photosensitizable compound may be linked to the polymeric support by using a dopant, such as an acrylic acid. The dopant may be incorporated into the polymeric support to provide a binding site for the photosensitizable compound or the dopant may be bonded to the photosensitizable compound and the resultant compound copolymerized with the polymeric support.

Reagents such as carbodiimides, 1,1'-carbonyldiimidazole, cyanuric chloride, chlorotriazine, cyanogen bromide and glutaraldehyde, and processes such as use of mixed anhydrides, reductive amination and metal-assisted cross-couplings of halogenated compounds with organometallic compounds may also be used to couple the photosensitizable compound to the insoluble support.

In one particular embodiment, when the photosensitizable compound represents a benzoporphyrin, a purpurin, a chlorophyll, an haematoporphyrin, a phorbine, a bacteriochlorin or a porphyrinogen having a group X representing CH═CH$_2$, the photosensitizable compound may be co-polymerised with monomers, such as plastics made from unsaturated monomers (ie polyethylene, polypropylene, polyacrylates, polystyrene, polyamide) by processes such as free radical induced polymerisation to give either rigid or flexible insoluble polymeric matrices incorporating the desired photosensitizable compound.

In a further embodiment, when the photosensitizable compound represents a benzoporphyrin, a porphycene, a purpurin, a chlorophyll, an haematoporphyrin, an etiopurpurin, a phorbine, a verdin, a bacteriochlorin or a porphyrinogen having a group X representing CO$_2$R$^{20}$, the photosensitizable compound may be incorporated into a polymer having a NHR$^{15}$ group via amide bond formation by techniques which are well-known to those skilled in the art. Alternatively, the photosensitizable compound may be incorporated into a polymer having a carboxyl group by formation of a diamide type linkage using a bis-amino spacer.

In a further embodiment, when the photosensitizable compound represents a porphycene having a group X representing NHR$^{15}$, then the photosensitizable compound may be incorporated into a polymer having a CO$_2$R$^{20}$ group via amide bond formation by techniques which are well-known to those skilled in the art. Alternatively, the photosensitizable compound may be incorporated into a polymer having an amino group by formation of a urea type linkage.

In yet a further embodiment, when the photosensitizable compound is an haematoporphyrin, a phorbine or a porphyrinogen having a group X representing OH, then the photosensitizable compound may be incorporated into a functionalised silica group, such as a glass, by formation of a silyloxy linkage by methods well known to those skilled in the art.

In a further embodiment, when the photosensitizable compound is a phorbine or a bacteriochlorin having a group X representing SH, then the photosensitizable compound may be bonded through the sulphur atom to the surface of a noble metal, such as metallic gold, thus forming a thio ether or disulfide linkage by methods well known to those skilled in the art.

In a further embodiment, when the photosensitizable compound is a chlorphyrin having a group X representing C≡CH, then the photosensitizable compound may be copolymerised with monomers, such as plastics made from unsaturated monomers (ie polyethylene, polypropylene, polyacrylates, polystyrene, polyamide) or the photosensitizable compound may be incorporated into a polymer having a halo, C≡CH, CH=CH$_2$, MgCl or ZnCl group by processes such as free radical-induced polymerisation or metal mediated cross-coupling to form either rigid or flexible insoluble polymeric matrices incorporating the photosensitizable compound.

Where the photosensitizable compound is derived from natural sources, advantage may be taken, for instance, of vinyl or carboxyl groups that are present in the native compound. The isolation and/or synthesis of such photosensitizable compounds as previously defined for a compound of formula I are described for example in Bonnett R. 'Photosensitizers of the Porphyrin and Phthalocyanine Series for Photodynamic Therapy', *Chemical Society Reviews* (1995), 19–34; Dougherty T J 'Is PDT a Useful Cancer Treatment?', *International Photodynamics* (1995) 1(2), 2–3; Lin C-W 'Photodynamic Therapy of Malignant Tumors—Recent Developments', *Cancer Cells* (1991) 3(11), 437–444; Garbo G M 'Purpurins and benzochlorins as sensitizers for photodynamic therapy', *Journal of Photochemistry and Photobiology B: Biology* (1996) 34, 109–116; Braslavsky S E et al. 'Photophysical Properties of Porphycene derivatives (18 π porphyrinoids)', Journal of Photochemistry and Photobiology B: Biology (1997) 40, 191–198.

Alternatively, these and other functionalities may also be introduced into the photosensitizable compound using the appropriate chemistry on suitably protected precursor molecules. For example, carboxyl groups may be activated by conversion to the corresponding acid chloride, azide or activated ester and then incorporated into a construct by treatment with a polymeric matrix bearing nucleophilic substituents.

The following reaction scheme is one example of a route to the compositions of the present invention comprising a photosensitizable compound and the insoluble support, which is preferably a compound of formula XIV or XV, where the photosensitizable compounds are synthesised for incorporation into the insoluble support to form a construct:

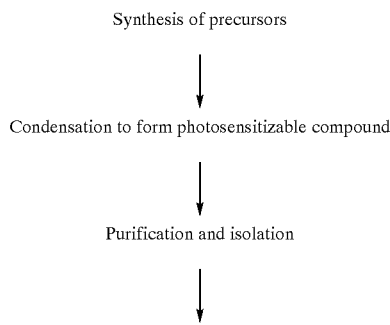

Synthesis of precursors
↓
Condensation to form photosensitizable compound
↓
Purification and isolation
↓
-continued
Insertion of metal atom
↓
Functionalisation of the side-chain or of the macrocyclic core
↓
Addition to, or incorporation into, the insoluble support to give construct By appropriate protection strategies, linkage of the photosensitizable compound to support matrices can be made through specific functional groups in multi-functional molecules.

It is evident to those skilled in the art that the synthetic steps need not always be carried out in the specific order given above but that flexibility exists in the routes especially in the order of performing the steps of protection and deprotection, or whether protection is used at all, the metal insertion reaction, the purification steps, any reduction operations, and the functionalisation and attachment or incorporation steps.

The precursors may be synthesised using methods such as standard peptide chemistry described in the literature, for example in Houben Weyl, *Methoden der Organischen Chemie*, Parts 1 and 2, Vol 15. If necessary the carboxyl, amino, hydroxyl or thio functionalities of the precursor molecules may be protected using suitable reversible protecting groups. The use of protecting groups is fully described in "*Protective Groups in Organic Chemistry*", edited by J W F McOmie, Plenum Press (1973), and "*Protective Groups in Organic Synthesis*", $2^{nd}$ edition, T W Greene & P G M Wutz, Wiley-Interscience (1991).

The protected precursor molecules may be condensed with spacer molecules such as natural amino acids or other linkers by methods well known to those skilled in the art to give mixtures of derivatised protected photosensitizable compounds (for subsequent covalent linkage to preformed polymeric supports) which are enriched in the desired photosensitizable compound by appropriate choice of the relative amounts of the precursors and the conditions of the condensation reaction.

The desired photosensitizable compound may be isolated by chromatographic separation or crystallisation. These procedures can be optimised by judicious choice of the groups R combined with reversible optional protection of the function in the side-chain, if appropriate. At this point it can be advantageous to insert the metal atom into the macrocycle. The functional group, where appropriate, is activated or derivatised, and the macrocycle can be attached to a surface or copolymerised with a suitable comonomer. At various points in the sequence of reactions, it is possible to manipulate the photosensitizable compound structure when separation of any isomers is desired.

The compositions of the invention are photodynamic as they emit reactive oxygen species, such as singlet oxygen or oxygen free radicals, following irradiation with light of the appropriate wavelength in the presence of oxygen. Consequently, the compositions of the invention are suitable for use in the curative and/or prophylactic treatment of a medical condition for which a photodynamic agent is indicated. Preferably, the compositions of the invention arc suitable for use in the curative and/or prophylactic treatment of atherosclerosis; cataracts; restenosis; secondary cataracts;

endometrial ablation; cancers such as bladder cancer; other proliferative diseases; bacterial infections such as Gram-positive cocci (eg Streptococcus), Gram-negative cocci (eg Neisseria), Gram-positive bacilli (eg Corynebacterium species) Gram-negative bacilli (eg *Escherichia coli*) acid-fast bacilli (eg a typical Mycobacterium) and including infections causing abscesses, cysts, arthritis, urinary tract infections, pancreatitis, pelvic inflammatory disease, peritonitis, prostatitis, vaginal infections, ulcers and other localised infections; actinomyces infections; fungal. infections such as *Candida albicans*, Aspergillus and Blastomyces; viral infections such as HIV, encephalitis, gastroenteritis, haemorrhagic fever, hantavirus, viral hepatitis, herpesvirus (eg cytomegalovirus, Epstein-Barr, herpesvirus simiae, herpes simplex and varicella-zoster); protozoal infections such as amoebiasis, babesiosis, coccidiosis, cryptosporidiosis, giardiasis, Leishmaniasis, Trichomoriasis, toxoplasmosis and malaria; helminthic infections such as caused by nematodes, cestodes and trematodes, eg ascariasis, hookworm, lymphatic filariasis, onchocerciasis, schistosomiasis and toxocariasis; and inflammatory diseases such as soft-tissue rheumatism, osteoarthlritis, rheumatoid arthritis and spondyloarthropathies. The cytotoxicity of the photodynamic therapy may kill the infecting cells (in the case of bacteria or fungi) or the affected host cells (in the case of viral infections and inflammatory disease).

In a particular preferred composition the insoluble support is a noble metal film, preferably the noble metal is gold and the thickness of the film is 10 to 1000 nm. When the support is gold, X in a compound of the invention of formula I or a photosensitizable compound of formula XVI may represent SH or S—]$_2$. The compound of formula I or the photosensitizable compound is bonded through the sulphur atom to the surface of the metallic gold thus forming a thio ether or disulphide linkage.

A noble metal film coated with a compound of the invention or a photosensitizable compound may be prepared by immersing the film in a solution of a compound of formula I, wherein X represents SH or S—]$_2$, in a suitable solvent, such as hexane, chloroform or dichloromethane, at room temperature for up to 24 hours, optionally with stirring.

In a further preferred composition the insoluble support includes a glass surface and X in the compound of formula I or X in the photosensitizable compound of formula XVI may represent Si(halo)$_3$, particularly Si(Cl)$_3$. The photosensitizable compound is then bonded through the silicon atom to the glass surface The compositions of the invention may be fabricated into or coated on various medical devices and surgical implants, such as balloon catheters, vascular stents, intraocular lenses, orthopacdic implants, other artificial surgical implants, interfaces, artificial joints, surgical screws and pins. Each of the medical devices may also optionally include an integrated light delivery system.

A vascular stent is a permanent implant comprising a mesh-like tube which is used to maintain an open lumen within the blood vessels. Typically, a vascular stent is made from metal, stainless steel, nickel, platinum, all of which are optionally coated with a polymer to increase biocompatability. Alternatively, the stent may be made completely from polymers or plastics.

In a typical surgical procedure, the stent is delivered to the target site in a blood vessel with a guide catheter, usually after a patient has been administered a bolus of heparin. Preferably, the guide catheter has a retractable sheath which shields the stent until it is at the target site. After the catheter has been directed to the target site. After the catheter has been directed to the target site possibly with the aid of a contrast medium, the sheath is retracted to expose the stent. The stent either self expands or it is expanded with an inflatable balloon of a balloon catheter. The stent delivery system, balloon and catheter are removed leaving the stent within the blood vessel.

An intraocular lens is a lens that is adapted to be fixed to the periphery of the iris or an opening in the capsular bag of the eye. Typically, the lens is made from an acrylic polymer, such as polymethyl methacrylate or hydroxyethyl methacrylate, optionally coated with a biocompatible polymer such as phosphorylcholine. A suitable intraocular lens (IOL) is described in U.S. Pat. No. 5,716,364, which is incorporated herein by reference. The IOL is made of a polymeric material such as a polyolefin, for example polypropylene.

Preferably, the coating is a molecular monolayer that partially or totally coats the surface of the medical device.

The coating may be fixed to the medical device by forming a bond between the —ZX functional group of the compound of the invention of formula I or a photosensitizable compound of formula XVI and the reactive U functional groups of the insoluble support as previously defined. For example, the coating may be fixed to a balloon catheter with covalent bonds, such as ether, ester, ainide, amine, carbamate, urea, keto, poly(alkyloxy), —CH=CH—, —C≡C—, —Si(OR$^{17}$)$_2$—, —SiR$^{18}$R$^{19}$—, —SiR$^{17}$R$^{18}$—, amino alcohol, amino acyl, lower alkenyl, aryl or lower alkylaryl linkages, using methods which are well known to those skilled in the art.

Alternatively, the coating may be formed by reacting the compounds or compositions of the invention with the polymeric precursors of a medical device prior to formation of the medical device.

It will be appreciated that when the medical device comprises a silica based polymer optionally having reactive or functionalised silica groups, such as a silicone polymer, the medical device also acts as the insoluble support and it may be coated and/or impregnated by direct reaction with a compound of the invention of formula I or a photosensitizable compound of formula XVI. The compound of the invention or the photosensitizable compound is bonded to the silicone polymer with one of the linkages as previously disclosed herein.

The medical devices enable the compounds of the invention and the photosensitizable compounds to be delivered to a particular target tissue. For example, in the treatment of atherosclerosis/restenosis the target cells arc the smooth muscle cells on the blood vessel lumen surface, and inflammatory cells such as macrophages, whereas in the treatment of cataracts the target cells are the lens epithelial cells on the inner surface of the capsular bag which are typically aggregated around the periphery of the capsular bag. This site specific delivery reduces or substantially eliminates undesirable side-effects associated with photodynamic agents residing in and accumulating in non-target tissues. This increases patient compliance as a patient who has been treated with a medical device of the present invention only needs to shield the treated tissue from exposure to light, rather than other parts of the body which may be necessary with photodynamic agents having no site specific delivery system.

Typically, following absorption of light of the approximate wavelength, preferably 500 to 800 nm, the coating of the medical device emits reactive oxygen species, such as singlet oxygen, which travel a distance of between 50 nm and 5 nm (micrometers) from the device depending on the composition of the medium surrounding the device. For example, if the medium is a biological tissue then the reactive oxygen species travel between 10 and 50 nm from the device, whereas the reactive oxygen species travel approximately 1 to 5 μm from the device when the medium is a saline solution, even greater distances 10 to 100 μm can be achieved in other liquids, alcohols, acetone and aqueous mixtures thereof.

Each of the medical devices may also include a fluid delivery system for delivering desired medium to the coating of the device. Hence, and in contrast to the small limited distances (eg 10–50 nm) of emission of reactive oxygen species from photodynamic sensitisers administered directly into cells, the distance the reactive oxygen species emitted from the devices of the present invention may be controlled accurately. This further reduces the undesirable side-effects associated with reactive oxygen species interacting with non-target tissue and thereby further increases patient compliance.

It will be appreciated that the material introduced into the body will be sterile and may also be non-pyrogenic. Sterility is typically achieved by conventional temperature, pressure, radiation or chemical sterilisation treatment techniques, preferably during the manufacture of the devices.

In a further aspect, the present invention provides methods for treating or preventing cataracts, secondary cataracts, bladder cancers, restenosis, atherosclerosis, endometrial ablation, other cancers and proliferative diseases, inflammation and infection using the medical devices of the invention.

In yet a further aspect, the present invention provides a method of producing light-induced singlet oxygen which comprises irradiating a compound or composition of the invention with light of the appropriate wavelength preferably 500 to 800 nm, in the presence of oxygen.

DESCRIPTION OF THE DRAWINGS

A preferred embodiment of the invention will now be described by way of example, with reference to the accompanying drawings in which.

DESCRIPTION OF PREFERRED EMBODIMENT

1. Inflatable Balloon and Delivery Catheter

Figure 1:
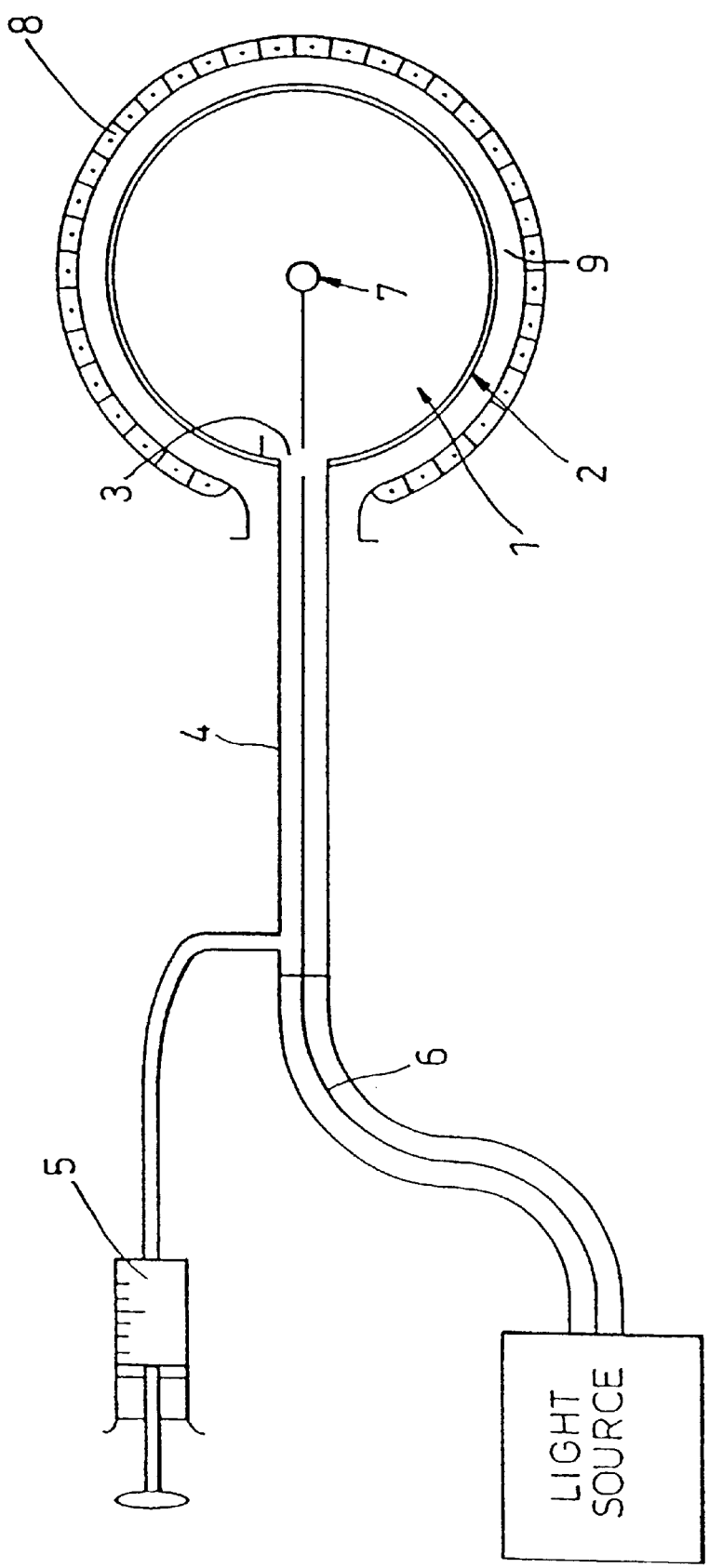
FIG. 1 is a longitudinal cross-section of a preferred balloon attached to a catheter.

FIG. 1 shows a preferred embodiment of the invention comprising a balloon 1 having a surface coating 2 of a photodynamic compound or composition, an inflation port 3 and a two-way valve (not shown) to enable the balloon to be selectively inflated and deflated. The balloon is preferably made from an elastomeric material, such as a flexible silicone polymer, and the coating is fixed to the balloon with linkage as described herein before.

The balloon is attached to a first end of a catheter 4. A second end of the catheter includes means for receiving a pressure controlled inflation device 5, such as a standard Luer pressure tight connector having a stopcock.

The pressure controlled inflation device 5 is a normal syringe used in standard angioplastic and intraocular procedures with balloon catheters. The syringe has an accurate graduation for measuring the volume of fluid injected into the balloon. It may also be optionally fitted with a pressure gauge. In use, pressure and volume measurements enable the balloon to be fully inflated at the target site whilst reducing the risk of damaging the surrounding non-target healthy tissue.

The first end of the catheter terminates in an injection means for filling the balloon with a filler material which is preferably a biocompatible fluid, such as sterile water. Preferably the catheter includes a fluid delivery system (not shown) for delivering a desired medium to the coating 2.

A light source, preferably a fibre optic cable 6, extends throughout the length of the catheter and into the interior of the balloon 1 terminating with means for distributing light 7 in the balloon.

In use, the complete surgical procedure is carried out endoscopically.

Procedure for the Treatment of Atherosclerosis, Restenosis, Bladder Cancers or Endomnetrial Ablation i. Pre-Surgical Preparation Air is removed from the apparatus before commencing the surgical operation by connecting tie syringe, typically a 30 ml syringe, to the Luer pressure tight connector, opening the stopcock and withdrawing the syringe piston. The stopcock is closed and the syringe removed. The apparatus is now ready for use.

ii. Surgical Procedure

After the balloon has been presented to the target tissue 8, a pressure controlled inflation device, preferably a30 ml syringe containing sterile water with no air bubbles and fitted with a pressure gauge, is attached to the luer fitting, the stopcock is opened and the balloon 1 inflated to a specific volume and/or pressure with the sterile water. The required volume/pressure for inflation of the balloon can be determined by routine trial and error testing by a skilled person.

A light source is operated so that light of the appropriate wavelength, typically 500 to 800 nm, passes through the fibre optic cable into the interior of the balloon. The coating 2 absorbs the light and emits singlet oxygen radicals in the vicinity of the balloon, typically within a radius of between 50 nm and 5 μm from the balloon. The fluid delivery system may be used to deliver a desired fluid into the space 9 between the coating 2 and the target tissue 8, thereby enabling the user to vary and control the distance the singlet oxygen species are emitted from the balloon 1. The singlet oxygen radicals induce molecular and cellular destruction of the target tissue.

The invention is further illustrated by way of the following examples.

General Experimental Procedures

Mass spectra were recorded on a Finnigan MAT TSQ 700 triple quadrupole mass spectrometer equipped with an electrospray interface (FAB-MS). The matrix-assisted laser desorption/ionization mass spectra of the porphyrins were obtained using a dithranol matrix. FAB-MS spectra were obtained using a 3-nitrobenzyl alcohol (NOBA) matrix. $^1$H-NMR spectra were measured at 60 MHz on a Jeol JNM-PMX60 spectrometer, at 270 MHz on a Jeol EX 270 spectrometer and at 300 MHx on a Varian Gemini-300 spectrometer in CDCl$_3$ using TMS as an internal reference.

Ultraviolet/visible spectra of solutions of compounds in tetrahydrofuran (THF) or toluene were measured using a Hitachi U-3000 spectrophotometer or a ATI-Unicam UV-2 spectrophotometer. Reflectance-absorbance infra red (RAIR) spectra were recorded on a BIO-RAD FTS 165 spectrophotometer. Fluorescence emission spectra were recorded using a Spex Fluorolog 3 spectrophotometer at an excitation wavelength of 355 nm, emission at 550 to 800 nm, with a bandpass of 2 nm.

Column chromatography was carried out using silica gel 60, 0.035–0.070 mm (220–440 mesh) or silica gel 60, 0.060–0.2mm (70–230 mesh), both of which are available from BDH, Poole, Dorset, UK.

The singlet oxygen quantum yields were determined by the direct measurement of singlet oxygen phosphorescence at 1270 nm. Samples were excited using the third harmonic of a Q-switched Nd:YAG (neodymium: yttrium-aluminium-garnet) Spectra Physics GCR-150-10 laser, operating at an excitation wavelength of 355 nm. A small fraction of the laser output was passed through a solution state filter containing aqueous cobalt (II) sulphate ($CoSO_4$) to remove residual 532 and 1064 nm radiation and then down a 8 mm diameter liquid light guide (Oriel). For the measurements the end of the light guide was held against a 1 cm×1 cm fluorescence cuvette (Hellma) holding the sample. During the course of the experiments the incident laser energy for each measurement was determined using a pyroelectric detector held behind the sample. This detector was calibrated at the start of the experiment using a second calibrated energy meter (Gentec ED100). The laser energy was adjusted by placing cells containing aqueous sodium nitrite between the $CoSO_4$ filter and the light guide. Typical pulse energies used were in the range of 25–500 $\mu J$ per pulse. Shot to shot noise was estimated to be <10% and sets of 20 shots gave an average value within <3%.

Phosphorescence from the sample was collected and passed through an interference filter centred at 1270 nm available from (Infra Red Engineering Ltd) and then focused onto the active area of a liquid nitrogen cooled germanium photodiode (North Coast EO-817P). The output from this device was AC coupled to a digital oscilloscope (Tektronix TDS-320) which digitised and averaged the transients. Typically 20 laser shots were used for each sample. The averaged data was transferred to a PC where it was stored and analysed.

In the following examples, the title compounds of Examples 2 to 8 represent compounds of formula V, the title compounds of Examples 9 to 14 represent compounds of formula VI, VII and VIII, the title compounds of Examples 28 to 40 represent compounds of the formula III, the title compounds of Examples 54 to 66 represent compounds of formula II and the title compounds of Examples 67 to 81 represent compounds of formula I.

EXAMPLE 1

12-Bromododecan-1-ol 1,12-Dodecanediol (50 g, 0.25 mol) in hydrogen bromide 48% (220 ml) was continuously extracted with petroleum ether (b.p. 80–100° C.) (300 ml) for 18 hours. The solvent was evaporated under reduced pressure and the crude oil obtained was filtered through a pad of silica gel. Elution with petroleum ether (b.p. 40–60° C.) gave a colourless fraction containing 1,12-dibromododecane. The silica gel was then eluted with acetone to give the title compound as a pale yellow oil after evaporation of the solvent. The title compound crystallised upon cooling and was recrystallised from petroleum ether (b.p. 40–60° C.).

$^1H$ NMR (60 MHz; $CDCl_3$): 3.62 (t, 2H), 3.42 (t, 2H), 1.4 (brs, 21H).

EXAMPLE 2

4-(12-Hydroxy-dodecyloxy)-benzaldehyde

A mixture of 12-bromododecan-1-ol (15 g, 57 mmol, see Example 1 above), 4-hydroxy-benzaldehyde (6.9 g, 57 mmol), potassium carbonate (excess), potassium iodide (trace) and tetra-n-butylammonium iodide (trace) was heated at reflux in methyl ethyl ketone (50 ml) for 16 hours. After cooling, the solids were filtered off and washed with acetone. The combined organic fractions were evaporated to dryness. Diethyl ether was added to the resultant oil and the solution was stored at 4° C. The title compound precipitated and was collected by filtration.

$^1H$ NMR (60 MHz; $CDCl_3$): 9.9 (s, 1H), 7.9 (d, 2H), 7.0 (d, 2H), 4.1 (t, 2H), 3.62 (t, 2H), 1.3 (brs, 21H).

EXAMPLE 3

4-(6-Hydroxy-hexyloxy)-benzaldehyde

The title compound was prepared according to the method described in Example 2 above from 6-bromohexan-1-ol. The title compound was obtained as an oil.

$^1H$ NMR (60 MHz; $CDCl_3$): 9.8 (s, 1H), 7.82 (d, 2H), 7.0 (d, 2H), 4.08 (t, 2H), 3.82 (s, 1H), 3.7 (t, 2H), 1.2–2.1 (m, 8H).

EXAMPLE 4

4-(16-Hydroxy-hexadecyloxy)-benzaldehyde

To a stirred solution of 4-hydroxy-benzaldehyde (0.24 g, 2mmol) and 1,16-dihydroxyhexadecane (0.51 g, 2 mmol), triphenylphosphine (0.53 g, 2 mmol) in dry THF (20 ml) at −15° C. under an argon atmosphere was added a solution of diisopropylazodicarboxylate (0.4 g, 2 mmol) in dry THF (7.5 ml) over a period of 40 minutes. The mixture was allowed to warm to room temperature overnight. The solvent was removed under reduced pressure, diethyl ether was added and the white solid formed was removed by filtration. The filtrate was evaporated to dryness and the residue purified by chromatography on a column of silica gel which was, eluted with petroleum ether (b.p. 40–60° C.):tetrahydrofuran (THF) (10:1 by volume) to yield the title compound which was used directly without further purification.

$^1H$ NMR (300 MHz; $CDCl_3$): 9.83 (s, 1H), 7.85 (d, 2H), 6.95 (d, 2H), 4.05 (t, 2H), 3.6 (t, 2H), 1.2–1.9 (m, 28H).

EXAMPLE 5

4-[10-Undecenyloxy]-benzaldehyde

A mixture of 11-bromoundec-1-ene (2.02 g), 4-hydroxy-benzaldehyde (1.06 g, 8.6 mmol), potassium carbonate, potassium iodide and tetra-n-butylamomnium iodide was heated at reflux in methyl ethyl ketone (10 ml) for 16 hours. After cooling, the solids were filtered off and washed with acetone. The combined organic fractions were evaporated to dryness. The crude product obtained was filtered through a pad of silica gel which was eluted with petroleum ether (b.p. 40–60° C.) to remove the excess of bromoundecene. The silica gel was then eluted with acetone and the acetone fractions evaporated under reduced pressure to yield the title compound.

¹H NMR (60 MHz; CDCl₃): 9.9 (s, 1H), 7.8 (d, 2H), 7.0 (d, 2H), 5.5–6.1 (m, 1H), 4.8–5.2 (m, 2H), 4.1 (t, 2H), 1.2–2.2 (m, 16H).

EXAMPLE 6

Acetic Acid 12-(4-Formyl-phenoxy)-dodecyl Ester 4-(12-Hydroxyl-dodecyloxy)-benzaldehyde (1.1 g, 3.6 mmol, see Example 2 above) was heated at reflux in acetic anhydride (15 ml) for 90 minutes. After cooling, the solution was poured into water with stirring. The title compound formed as a precipitate which was collected by filtration, washed with water and dried.

¹H NMR (60 MHz; CDCl₃): 9.82 (s, 1H), 7.8 (d, 2H), 7.0 (d, 2H), 4.0 (t, 4H), 2.02 (s, 3H), 1.3 (brs, 20H).

EXAMPLE 7

Acetic Acid 6-(4-Formyl-phenoxy)-hexyl Ester

The title compound was prepared according to the method described in Example 6 from 4-(6-hydroxy-hexyloxy)-benzaldehyde (see Example 3 above). After addition of the reaction mixture to water, the title compound was obtained as a yellow oil. The oil was extracted with diethyl ether, the etheral extract was washed with aqueous K₂CO₃, brine, and dried over MgSO₄, filtered and the solvent removed under reduced pressure.

¹H NMR (60 MHz; CDCl₃): 9.9 (s, 1H), 7.82 (d, 2H), 7.0 (d, 2H), 4.1 (t, 4H), 2.02 (s, 3H), 1.2–2.1 (m, 8H).

EXAMPLE 8

Acetic Acid 16-(4-Formyl-phenoxy)-hexadecyl Ester

The title compound was prepared as described in Example 6 from 4-(16-hydroxy-hexadecyloxy)-benzaldehyde (see Example 4 above). The title compound was obtained as an oil.

¹H NMR (270 MHz; CDCl₃): 9.88 (s, 1H), 7.83 (d, 2H, J=8.6 Hz), 7.0 (d, 2H, J=8.6 Hz), 4.0–4.1 (m, 4H), 2.04 (s, 3H), 1.2–1.9 (m, 38H).

EXAMPLE 9

3,4,5-Tridecyloxy-benzaldehyde

A mixture of 3,4,5-trihydroxy-benzaldehyde (3 g, 20 mmol), 1-bromodecane (20 ml, excess), potassium carbonate (excess), potassium iodide (trace) and tetra-n-butylammonium iodide (trace) was heated at reflux in methyl ethyl ketone (60 ml) for 16 hours. After cooling, the solid was collected by filtration and washed with acetone. The combined organic fractions were evaporated to yield an oil. The oil was filtered through a pad of silica gel. Elution with petroleum ether (b.p. 40–60° C.) gave bromodecane on evaporation of the solvent. The silica gel was then eluted with acetone to give the title compound, after evaporation of the solvent, as a pale yellow oil which was used without further purification.

¹H NMR (60 MHz; CDCl₃): 9.8 (s, 1H), 7.1 (s, 2H), 4.1 (brt, 6H), 1.3 (brs, 48H), 0.9 (t, 9H).

EXAMPLE 10

3,4,5-Trihexyloxy-benzaldehyde

The title compound was prepared according to the method described in Example 9 above from 1-bromohexan and 3,4,5-trihydroxy-benzaldehyde.

¹H NMR (60 MHz; CDCl₃): 9.8 (s, 1H), 7.1 (s, 2H), 4.1 (brt, 6H), 1.3 (brs, 24H), 0.9 (t, 9H).

EXAMPLE 11

3,4,5-Trihexadecyloxy-benzaldehyde

The title compound was prepared according to the method as described in Example 9 above from 1-bromohexadecane and 3,4,5-trihydroxy-benzaldehyde, except the reaction mixture was heated at reflux for 4 days. After cooling, the solid material was removed by filtration and the solid washed with dichloromethane. The combined organic extracts were evaporated under reduced pressure to yield the title compound which was recrystallised from dichloromethane-ethanol.

¹H NMR (300 MHz; CDCl₃): 9.84 (s, 1H), 7.08 (s, 2H), 3.9–4.1 (m, 6H), 1.0–1.9 (m, 42H), 0.88 (t, 9H).

EXAMPLE 12

3,5-Dihexyloxy-benzaldehyde

The title compound was prepared according to the method described in Example 9 above from 3,5-dihydroxy-benzaldehyde and 1-bromohexane.

¹H NMR (60 MHz; CDCl₃): 9.9 (s, 1H), 7.0 (m, 2H), 6.7 (m, 1H), 4.0 (t, 4H), 1.1–2.0 (m, 16H), 0.9 (t, 6H).

EXAMPLE 13

3,5-Didecyloxy-benzaldehyde

The title compound was prepared according to the method described in Example 9 above from 1-bromodecane and 3,5-dihydroxy-benzaldehyde.

¹H NMR (60 MHz; CDCl₃): 9.8 (s, 1H), 7.0 (m, 2H), 6.7 (m, 1H), 4.0 (t, 4H), 1.1–2.1 (m, 32H), 0.9 (t, 6H).

EXAMPLE 14

3,5-Dihexadecyloxy-benzaldehyde

The title compound was prepared according to the method described in Example 9 above from 1-bromohexadecane and 3,5-dihydroxy-benzaldehyde. The solid reaction product was collected by filtration and washed with methyl ethyl ketone (Soxhlet). The filtrate was evaporated under reduced pressure to give the title compound as a red oil which was crystallised from acetone.

¹H NMR (60 MHz; CDCl₃): 9.9 (s, 1H), 7.0 (m, 2H), 6.7 (m, 1H), 4.0 (t, 4H), 1.0–2.0 (m, 56H), 0.9 (t, 6H).

EXAMPLE 15

5-[4-(12-Acetyloxy-dodecyloxy)-phenyl]-10,15,20-tris-(3,4,5-tridecyloxy-phenyl)-porphyrin 3,4,5-Tridecyloxy-benzaldehyde (3.51 g, 6 mmol, see Example 9) and acetic acid 12-(4-formyl-phenoxy)-dodecyl ester (0.71 g, 2 mmol, see Example 6) were heated in propionic acid (40 ml) containing nitrobenzene (10 ml) to 130° C. Pyrrole (0.55 g, 8 mmol) was added and the temperature was maintained at 130° C. for 3 hours. The solution was cooled and an excess of methanol was added. The resultant solution was kept at 4° C. overnight. A heavy dark oil which collected was separated by decantation of the supernatant. The oil was washed with methanol and purified by column chromatography on silica gel eluted with petroleum ether (b.p. 40–60° C.):THF (10:1 by volume) to yield the title compound which was used without further purification.

$^1$H NMR (270 MHz; CDCl$_3$): 8.86–8.94 (m, 8H), 8.1 (d, J=8 Hz, 2H), 7.42 (s, 6H), 7.27 (d, J=8 Hz, 2H), 4.29 (brt, 8H), 4.08 (t, 14H), 2.26 (s, 3H), 1.2–2.0 (m, 164H), 0.91 (t, 9H), 0.83 (t, 18H), −2.79 (s, 2H).

EXAMPLE 16

5-[4-(12-Acetyloxy-dodecyloxy)-phenyl]-10,15,20-tris-(3,4,5-trihexyloxy-phenyl)-porphyrin The title compound was prepared according to the method described in Example 15 above from 3,4,5-trihexyloxy-benzaldehyde (see Example 10), acetic acid 12-(4-formyl-phenoxy)-dodecyl ester and pyrrole.

$^1$H NMR (270 MHz; CDCl$_3$): 8.85–9.0 (m, 8H), 8.1 (d, J=8 Hz, 2H), 7.42 (m, 6H), 7.27 (d, J=8 Hz, 2H), 4.29 (brt, 8H), 4.08 (t, 14H), 2.05 (s, 3H), 1.2–2.0 (m, 92H), 0.98 (t, 9H), 0.85 (t, 18H), −2.79 (s, 2H).

EXAMPLE 17

5-[4-(6-Acetyloxy-hexyloxy)-phenyl]-10,15,20-tris-(3,4,5-trihexyloxy-phenyl)-porphyrin The title compound was prepared according to the method described in Example 15 above from 3,4,5-trihexyloxy-benzaldehyde (see Example 10), acetic acid 6-(4-formyl-phenoxy)-hexyl ester (see Example 7) and pyrrole.

EXAMPLE 18

5-[4-(6-Acetyloxy-hexyloxy)-phenyl]-10,15,20-tris-(3,4,5-tridecyloxy-phenyl)-porphyrin The title compound was prepared according to the method described in Example 15 above from 3,4,5-tridecyloxy-benzaldehyde (see Example 9) and acetic acid 6-(4-formyl-phenoxy)-hexyl ester (see Example 7) and pyrrole.

EXAMPLE 19

5-[4-(6-Acetyloxy-hexyloxy)-phenyl]-10,15,20-tris-(3,4,5-trihexadecyloxy-phenyl)-porphyrin The title compound was prepared according to the method described in Example 15 above from 3,4,5-trihexadecyloxy-benzaldehyde (see Example 11), acetic acid 6-(4-formyl-phenoxy)-hexyl ester (see Example 7) and pyrrole.

EXAMPLE 20

5-[4-(12-Acetyloxy-dodecyloxy)-phenyl]-10,15,20-tris-(3,4,5-trihexyloxy-phenyl)-porphyrin The title compound was prepared according to the method described in Example 15 above from 3,4,5-trihexyloxy-benzaldehyde (see Example 10) acetic acid 12-(4-formyl-phenoxy)-dodecyl ester (see Example 6) and pyrrole.

EXAMPLE 21

5-[4-(12-Acetyloxy-dodecyloxy)-phenyl]-10,15,20-tris-(3,4,5-trihexadecyloxy-phenyl)-porphyrin The title compound was prepared according to the method described in Example 15 above from 3,4,5-trihexadecyloxy-benzaldehyde (see Example 11), acetic acid 12-(4-formyl-phenoxy)-dodecyl ester (see Example 6) and pyrrole.

EXAMPLE 22

5-[4-(16-Acetyloxy-hexadecyloxy)-phenyl]-10,15,20-tris-(3,4,5-tridecyloxy-phenyl)-porphyrin The title compound was prepared according to the method described in Example 15 above from 3,4,5-tridecyloxy-benzaldehyde (see Example 9), acetic acid 16-(4-formyl-phenoxy)-hexadecyl ester (see Example 8) and pyrrole.

EXAMPLE 23

5-[4-(16-Acetyloxy-hexadecyloxy)-phenyl]-10,15,20-tris-(3,4,5-trihexadecyloxy-phenyl)-porphyrin The title compound was prepared according to the method described in Example 15 above from 3,4,5-trihexadecyloxy-benzaldehyde (see Example 11), acetic acid 16-(4-formyl-phenoxy)-hexadecyl ester (see Example 8) and pyrrole.

EXAMPLE 24

5-[4-(12-Acetyloxy-dodecyloxy)-phenyl]-10,15,20-tris-(3,5-dihexyloxy-phenyl)-porphyrin The title compound was prepared according to the method described in Example 15 above from 3,5-dihexyloxy-benzaldehyde (see Example 12), acetic acid 12-(4-formyl-phenoxy)-dodecyl ester (see Example 6) and pyrrole.

EXAMPLE 25

5-[4-(6Acetyloxy-hexyloxy)-phenyl]-10,15,20-tris(3,5-didecyloxy-phenyl)-porphyrin The title compound was prepared according to the method described in Example 15 above from 3,5-didecyloxy-benzaldehyde (see Example 13), acetic acid 6-(4-formyl-phenoxy)-hexyl ester (see Example 7) and pyrrole.

EXAMPLE 26

5-[4-(12-Acetyloxy-dodecyloxy)-phenyl]-10,15,20-tris-(3,5-didecyloxy-phenyl)-porphyrin The title compound was prepared according to the method described in Example 24 above from 3,5-didecyloxy-benzaldehyde (see Example 13), acetic acid 12-(4-formyl-phenoxy)-dodecyl ester (see Example 6) and pyrrole.

EXAMPLE 27

5-[4-(12-Acetyloxy-dodecyloxy)-phenyl]-10,15,20-tris-(3,5-dihexadecyloxy-phenyl)-porphyrin The title compound was prepared according to the method described in Example 15 above from 3,5-dihexadecyloxy-benzaldehyde (see Example 14), acetic acid 12-(4-formyl-phenoxy)-dodecyl ester (see Example 6) and pyrrole.

EXAMPLE 28

5-[4-(12-Hydroxy-dodecyloxy)-phenyl]-10,15,20-tris-(3,4,5-tridecyloxy-phenyl)-porphyrin 5-[4-(12-Acetyloxy-dodecyloxy)-phenyl]-10,15,20-tris-(3,4,5-tridecyloxy-phenyl)-porphyrin (see Example 15) was heated to reflux in THF (10 ml) and ethanolic NaOH (excess) was added. When the reaction was complete as judged by thin layer chromatography, the solvent was evaporated under reduced pressure and the title compound was obtained by purification of the resultant residue by chromatography using a column of silica gel which was eluted with petroleum ether (b.p. 40–60° C.):THF (4:1 by volume).

$^1$H NMR (270 MHz; CDCl$_3$): 8.85–9.0 (m, 8H), 8.1 (d, J=8 Hz, 2H), 7.43 (s, 6H), 7.3 (d, J=8 Hz, 2H), 4.3 (t, 8H), 4.09 (t, 12H), 3.65 (brt, 2H), 1.2–2.05 (m, 164H), 0.91 (t, 9H), 0.84 (t, 18H), −2.77 (s, 2H).

EXAMPLE 29

5-[4-(12-Hydroxy-dodecyloxy)-phenyl]-10,15,20-tris-(3,4,5-trihexyloxy-phenyl)-porphyrin The title compound was prepared according to the method described in Example 28 above from 5-[4-(12-acetyloxy-dodecyloxy)-phenyl]-10,15,20-tris-(3,4,5-trihexyloxy-phenyl)-porphyrin (see Example 16).

$^1$H NMR (270 MHz; CDCl$_3$): 8.87–9.0 (m, 8H), 8.1 (d, J=8 Hz, 2H), 7.44 (s, 6H), 7.29 (d, J=8 Hz, 2H), 4.32 (t, 6H), 4.26 (t, 2H), 4.1 (t, 12H), 3.64 (brt, 2H), 1.2–2.1 (m, 92H), 1.0 (t, 9H), 0.88 (t, 18H), −2.76 (s, 2H).

EXAMPLE 30

5-[4-(6-Hydroxy-hexyloxy)-phenyl]-10,15,20-tris-(3,4,5-trihexyloxy-phenyl)-porphyrin The title compound was prepared according to the method described in Example 28 above from 5-[4-(6-acetyloxy-hexyloxy)-phenyl]-10,15,20-tris-(3,4,5-trihexyloxy-phenyl)-porphyrin (see Example 17).

EXAMPLE 31

5-[4-(6-Hydroxy-hexyloxy)-phenyl]-10,15,20-tris-(3,4,5-tridecyloxy-phenyl)-porphyrin The title compound was prepared according to the method described in Example 28 above from 5-[4-(6-acetyloxy-hexyloxy)-phenyl]-10,15,20-tris-(3,4,5-tridecyloxy-phenyl)-porphyrin (see Example 18).

$^1$H NMR (270 MHz; CDCl$_3$): 8.8–8.9 (m, 8H), 8.9 (d, 2H, J=8.25 Hz), 7.25–7.5 (m, 8H), 4.07–4.29 (m, 20H), 3.75 (t, 2H), 1.25–2.1 (m, 152H), 0.91 (t, 9H), 0.83 (t, 18H), −2.75 (s, 2H).

EXAMPLE 32

5-[4-(6-Hydroxy-hexyloxy)-phenyl]-10,15,20-tris-(3,4,5-trihexadecyloxy-phenyl)-porphyrin The title compound was prepared according to the method described in Example 28 above from 5-[4-(6-acetyloxy-hexyloxy)-phenyl)-10,15,20-tris-(3,4,5-trihexadecyloxy-phenyl)-porphyrin (see Example 19).

$^1$H NMR (270 MHz; CDCl$_3$): 8.86–8.94 (m, 8H), 8.1 (d, 2H, J=8.25 Hz), 7.43 (s, 6H), 7.27 (d, 2H, J=8.25 Hz), 4.29 (m, 8H), 4.08 (t, 12H), 3.74 (t, 2H), 1.0–2.0 (m, 260H) 0.9 (t, 9H), 0.88 (t, 18H), −2.75 (s, 2H).

EXAMPLE 33

5-[4-(12-Hydroxy-dodecyloxy)-phenyl]-10,15,20-tris-(3,4,5-trihexyloxy-phenyl)-porphyrin The title compound was prepared according to the method described in Example 28 above from 5-[4-(12-acetyloxy-dodecyloxy)-phenyl]-10,15,20-tris-(3,4,5-trihexyloxy-phenyl)-porphyrin (see Example 20).

$^1$H NMR (270 MHz; CDCl$_3$): 8.88–8.96 (m, 8H), 8.11 (d, 2H, J=8.6 Hz), 7.44 (s, 6H), 7.28 (d, 2H, J=8.6 Hz), 4.31 (t, 6H), 4.29 (t, 2H), 4.11 (t, 12H), 3.64 (t, 2H), 1.2–2.1 (m, 92H), 1.0 (t, 9H), 0.88 (t, 18H), −2.76 (s, 2H).

EXAMPLE 34

5-[4-(12-Hydroxy-dodecyloxy)-phenyl]-10,15,20-tris-(3,4,5-trihexadecyloxy-phenyl)-porphyrin The title compound was prepared according to the method described in Example 28 above from 5-[4-(12-acetyloxy-dodecyloxy)-phenyl]-10,15,20-tris-(3,4,5-trihexadecyloxy-phenyl)-porphyrin (see Example 21).

$^1$H NMR (270 MHz; CDCl$_3$): 8.83–8.91 (m, 8H), 8.07 (d, 2H, J=8.6 Hz), 7.39 (s, 6H), 7.25 (d, 2H, J=8.6 Hz), 4.2–4.3 (m, 8H), 4.06 (t, 12H), 3.63 (t, 2H), 1.0–2.0 (m, 272H), 0.8–0.97 (m, 27H), −2.81 (s, 2H).

EXAMPLE 35

5-[4-(16-Hydroxy-hexadecyloxy)-phenyl]-10,15,20-tris-(3,4,5-tridecyloxy-phenyl)-porphyrin The title compound was prepared according to the method described in Example 28 above from 5-[4-(16-acetyloxy-hexadecyloxy)-phenyl]-10,15,20-tris-(3,4,5-tridecyloxy-phenyl)-porphyrin (see Example 22).

$^1$H NMR (300 MHz; CDCl$_3$): 8.86–9.0 (m, 8H), 8.1 (d, 2H), 7.42 (s, 6H), 7.28 (d, 2H), 4.3 (t, 6H), 4.26 (t, 2H), 4.08 (t, 12H), 3.61 (t, 2H), 1.2–2.1 (m, 172H), 0.8–1.0 (m, 27H), −2.75 (s, 2H).

EXAMPLE 36

5-[4-(16-Hydroxy-hexadecyloxy)-phenyl]-10,15,20-tris-(3,4,5-trihexadecyloxy-phenyl)-porphyrin The title compound was prepared according to the method described in Example 28 above from 5-(4(16-acetyloxy-hexadecyloxy)-phenyl]-10,15,20-tris-(3,4,5-trihexadecyloxy-phenyl)-porphyrin (see Example 23).

$^1$H NMR (300 MHz; CDCl3): 8.85–9.0 (m, 8H), 8.1 (d, 21H), 7.42 (s, 6H), 7.28 (d, 2H), 4.3 (t, 6H), 4.26 (t, 2H), 4.08 (t, 12H), 3.6 (t, 2H), 1.2–2.1 (m, 280H), 0.8–0.9 (m, 27H), −2.8 (s, 2H).

EXAMPLE 37

5-[4-(12-Hydroxy-dodecyloxy)-phenyl]-10,15,20-tris-(3,5-dihexyloxy-phenyl)-porphyrin The title compound was prepared according to the method described in Example 28 above from 5-[4-(12-acetyloxy-dodecyloxy)-phenyl]-10,15,20-tris(3,5-dihexyloxy-phenyl)-porphyrin (see Example 24).

$^1$H NMR (270 MHz; CDCl$_3$): 8.77–8.88 (m, 8H), 8.01 (d, 2H, J=8.6 Hz), 7.3 (m, 6H), 7.16 (d, 2H, J=8.6 Hz), 6.8 (m, 3H), 4.12 (t, 2H), 4.03 (t, 12H), 3.5 (t, 2H), 1.1–1.9 (m, 68H), 0.81 (t, 18H), −2.88 (s, 2H).

EXAMPLE 38

5-[4-(6-Hydroxy-hexyloxy)-phenyl]-10,15,20-tris-(3,5-didecyloxy-phenyl)-porphyrin The title compound was prepared according to the method described in Example 28 above from 5-[4-(6-acetyloxy-hexyloxy)-phenyl]-10,15,20-tris(3,5-didecyloxy-phenyl)-porphyrin (see Example 25).

$^1$H NMR(270 MHz; CDCl$_3$): 8.82–8.93 (m, 8H), 8.07 (d, 2H, J=8.25 Hz), 7.34 (m, 6H), 7.3 (d, 2H, J=8.25 Hz), 6.86 (m, 3H), 4.24 (t, 2H), 4.09 (t, 12H), 3.73 (m, 2H), 1.1–2.1 (m, 104H), 0.82 (m, 18H), −2.84 (s, 2H).

EXAMPLE 39

5-[4-(12-Hydroxy-dodecyloxy)-phenyl]-10,15,20-tris-(3,5-didecyloxy-phenyl)-porphyrin The title compound was prepared according to the method described in Example 28 above from 5-[4-(12-acetyloxydodecyloxy)-phenyl]-10,15,20-tris-(3,5-didecyloxy-phenyl)-porphyrin (see Example 26).

$^1$H NMR (270 MHz; CDCl$_3$): 8.76–8.86 (m, 8H), 8.01 (d, 2H, J=8.6 Hz), 7.28 (m, 6H), 7.16 (d, 2H, J=8.6 Hz), 6.79 (m, 3H), 4.13 (t, 2H), 4.02 (t, 12H), 3.5 (t, 2H), 1.1–1.9 (m, 116H), 0.75 (t, 18H), −2.88 (s, 2H).

EXAMPLE 40

5-[4-(12-Hydroxy-dodecyloxy)-phenyl]-10,15,20-tris-(3,5dihexadecyloxy-phenyl)-porphyrin The title compound was prepared according to the method described in Example 28 above from 5-[4-(12-acetyloxy-dodecyloxy)-phenyl]-10,15,20-tris-(3,5-dihexadecyloxy-phenyl)-porphyrin (see Example 27).

$^1$H NMR (270 MHz; CDCl$_3$): 8.88–8.97 (m, 8H), 8.12 (d, 2H, J=8.6 Hz), 7.4 (s, 6H), 7.3 (d, 2H, J=8.6 Hz), 6.91 (m, 3H), 4.27 (t, 2H), 4.14 (t, 12H), 3.66 (t, 2H), 1.0–2.1 (m, 188H), 0.88 (t, 18H), −2.78 (s, 2H).

EXAMPLE 41

5-[4-(12-Methanesulfonyloxy-dodecyloxy)-phenyl]-10,15,20-tris-(3,4,5-tridecyloxy-phenyl)-porphyrin 5-[4-(12-Hydroxy-dodecyloxy)-phenyl]-10,15,20-tris-(3,4,5-tridecyloxy-phenyl)-porphyrin (0.193 g, 86 mmol, see Example 28) was dissolved in dichloromethane (8 ml) and the solution was maintained at ambient temperature using a water bath. Triethylamine (1 ml) was added, followed by methanesulphonylchloride (20 drops). The reaction mixture was stirred for 1 hour at ambient temperature. The solution was washed with dilute aqueous hydrochloric acid and brine, the organic extract dried over (MgSO$_4$), filtered and the solvent removed by evaporation at reduced pressure. Column chromatography on silica gel eluted with petroleum ether (b.p. 40–60° C.):THF (4:1 by volume) yielded the title compound.

$^1$H NMR (270 MHz; CDCl$_3$): 8.85–9.0 (m, 8H), 8.1 (d, J=8 Hz, 2H), 7.43 (s, 6H), 7.28 (d, J=8 Hz, 2H), 4.2–4.35 (m, 10H), 4.09 (t, 12H), 2.97 (s, 3H), 1.1–2.0 (m, 192H), 0.91 (t, 9H), 0.84 (t, 18H), −2.77 (s, 2H).

EXAMPLE 42

5-[42-(12-Methanesulfonyloxy-dodecyloxy)-phenyl]-10,15,20-tris3,4,5-trihexyloxy-phenyl)-porphyrin The title compound was prepared according to the method described in Example 41 above from 5-[4-(12-hydroxy-dodecyloxy)-phenyl]-10,15,20-tris-(3,4,5-trihexyloxy-phenyl)-porphyrin (see Example 29).

$^1$H NMR (270 MHz; CDCl$_3$): 8.87–9.0 (m, 8H), 8.11 (d, J=8 Hz, 2H), 7.44 (s, 6H), 7.3 (d, J=8 Hz, 2H), 4.2–4.35 (m, 10H), 4.1 (t, 12H), 2.98 (s, 3H), 1.3–2.1 (m, 92H), 1.0 (t, 9H), 0.87 (t, 18H), −2.76 (s, 2H).

EXAMPLE 43

5-[4-(6-Methanesulfonyloxy-hexyloxy)-phenyl]-10,15,20-tris-(3,4,5-trihexyloxy-phenyl)-porphyrin The title compound was prepared according to the method described in Example 41 above from 5-[4-(6-hydroxy-hexyloxy)-phenyl]-10,15,20-tris-(3,4,5-trihexyloxy-phenyl)-porphyrin (see Example 30).

$^1$H NMR (270 MHz; CDCl$_3$): 8.85–8.93 (m, 8H), 8.09 (d, 2H, J=8.25 Hz), 7.41 (s, 6H), 7.26 (d, 2H, J=8.25 Hz), 4.14.2 (m, 10H), 4.08 (t, 12H), 3.05 (s, 3H), 1.2–2.0 (m, 78H), 0.98 (t, 9H), 0.85 (t, 18H), −2.79 (s, 2H).

EXAMPLE 44

5-[4-(6-Methanesulfonyloxy-hexyloxy)-phenyl]-10,15,20-tris-(3,4,5-tridecyloxy-phenyl)-porphyrin The title compound was prepared according to the method described in Example 41 above from 5-[4-(6-hydroxy-hexyloxy)-phenyl]-10,15,20-tris-(3,4,5-tridecyloxy-phenyl)-porphyrin (see Example 31).

EXAMPLE 45

5-[4-(6-Methanesulfonyloxy-hexyloxy)-phenyl]-10,15,20-tris-(3,4,5-trihexadecyloxy-phenyl)-porohyrin The title compound was prepared according to the method described in Example 41 above from 5-[4-(6-hydroxy-hexyloxy)-phenyl]-10,15,20-tris-(3,4,5-trihexadecyloxy-phenyl)-porphyrin (see Example 32).

$^1$H NMR (270 MHz; CDCl$_3$): 8.8–8.93 (m, 8H), 8.1 (d, 2H), 7.42 (m, 6H), 7.25 (d, 2H), 4.3 (m, 10H), 4.08 (t, 12H), 3.05 (s, 3H), 1:0–2.0 (m, 260H), 0.8–0.9 (m, 27H), −2.8 (s, 2H).

EXAMPLE 46

5-[4-(12-Methanesulfonyloxy-dodecyloxy)-phenyl]-10,15,20-tris-(3,4,5-trihexyloxy-phenyl)-porphyrin The title compound was prepared according to the method described in Example 41 above from 5-[4-(12-hydroxy-dodecyloxy)-phenyl]-10,15,20-tris-(3,4,5-trihexyloxy-phenyl)-porphyrin (see Example 33).

$^1$H NMR (270 MHz; CDCl$_3$): 8.87–8.96 (m, 8H), 8.11 (d, 2H, J=8.6 Hz), 7.44 (s, 6H), 7.28 (d, 2H, J=8.6 Hz), 4.31 (t, 6H), 4.18–4.28 (m, 4H), 4.1 (t, 12H), 2.96 (s, 3H), 1.2–2.05 (m, 92H), 0.99 (t, 9H), 0.87 (t, 18H), −2.77 (s, 2H).

EXAMPLE 47

5-[4-(12-Methanesulfonyloxy-dodecyloxy)-phenyl]-10,15,20-tris-(3,4,5-trihexadecyloxy-phenyl)-porphyrin The title compound was prepared according to the method described in Example 41 above from 5-[4-(12-hydroxy-dodecyloxy)-phenyl]-10,15,20-tris-(3,4,5-trihexadecyloxy-phenyl)-porphyrin (see Example 34).

$^1$H NMR (270 MHz; CDCl$_3$): 8.85–8.93 (m, 8H), 8.09 (d, 2H, J=8.25 Hz), 7.42 (s, 6H), 7.27 (d, 2H, J=8.25 Hz), 4.2–4.3 (m, 10H), 4.08 (t, 12H), 2.99 (s, 3H), 1.2–2.0 (m, 272H), 0.83–0.9 (m, 27H), −2.79 (s, 2H).

EXAMPLE 48

5-[4-(16-Methanesulfonyloxy-hexadecyloxy)-phenyl]-10,15,20-tris-(3,4,5-tridecyloxy-phenyl)-porphyrin The title compound was prepared according to the method described in Example 41 above from 5-[4-(16-hydroxy-hexadecyloxy)-phenyl]-10,15,20-tris-(3,4,5-tridecyloxy-phenyl)-porphyrin (see Example 35).

$^1$H NMR (270 MHz; CDCl$_3$): 8.86–8.94 (m, 8H), 8.09 (d, 2H), 7.42 (m, 6H), 7.38 (d, 2H), 4.18–4.32 (m, 10H), 4.08 (t, 12H), 2.98 (s, 3H), 1.0–2.1 (m, 172H), 0.81–0.97 (m, 27H), −2.8 (s, 2H).

EXAMPLE 49

5-[4-(16-Methanesulfonyloxy-hexadecyloxy)-phenyl]-10,15,20-tris-(3,4,5-trihexadecyloxy-phenyl)-porphyrin The title compound was prepared according to the method described in Example 41 above from 5-[4-(16-hydroxy-hexadecyloxy)-phenyl]-10,15,20-tris-(3,4,5-trihexadecyloxy-phenyl)-porphyrin (see Example 36).

$^1$H NMR (270 MHz; CDCl$_3$): 8.85–8.95 (m, 8H), 8.1 (d, 2H), 7.4 (s, 6H), 7.3 (d, 2H), 4.18–4.32 (m, 10H), 4.08 (t, 12H), 3.0 (s, 3H), 1.0–2.1 (m, 280H), 0.8–0.9 (m, 27H), −2.8 (s, 2H).

EXAMPLE 50

5-[4-(12-Methanesulfonyloxy-dodecyloxy)-phenyl]-10,15,20-tris-(3,5-dihexyloxy-phenyl)-porphyrin The title compound was prepared according to the method described in Example 41 above from 5-[4-(12-hydroxy-dodecyloxy)-phenyl]-10,15,20-tris-(3,5-dihexyloxy-phenyl)-porphyrin (see Example 37).

$^1$H NMR (270 MHz; CDCl$_3$): 8.87–8.98 (m, 8H), 8.11 (d, 2H, J=8.25 Hz), 7.39 (m, 6H), 7.27 (d, 2H, J=8.25 Hz), 6.9 (m, 3H), 4.23 (t, 2H), 4.19 (t, 2H), 4.13 (t, 12H), 2.94 (s, 3H), 1.2–2.0 (m, 68H), 0.89 (t, 18H), −2.78 (s, 2H).

EXAMPLE 51

5-[4-(6-Methanesulfonyloxy-hexyloxy)-phenyl]-10,15,20-tris-(3,5-didecyloxy-phenyl)-porphyrin The title compound was prepared according to the method described in Example 41 above from 5-[4-(6-hydroxy-hexyloxy)-phenyl]-10,15,20-tris-(3,5-didecyloxy-phenyl)-porphyrin (see Example 38).

$^1$H NMR (270 MHz; CDCl$_3$): 8.93–9.05 (m, 8H), 8.19 (d, 2H, J=8.25 Hz), 7.46 (m, 6H), 7.32 (d, 2H, J=8.25 Hz), 6.96 (m, 3H), 4.32 (m, 4H), 4.19 (m, 12H), 3.06 (s, 3H), 1.2–2.1 (m, 104H), 0.91 (m, 18H), −2.71 (s, 2H).

EXAMPLE 52

5-[4-(12-Methanesulfonyloxy-dodecyloxy)-phenyl]-10,15,20-tris-(3,5-didecyloxy-phenyl)-porphyrin The title compound was prepared according to the method described in Example 41 above from 5-[4-(12-hydroxy-dodecyloxy)-phenyl]-10,15,20-tris-(3,5-didecyloxy-phenyl)-porphyrin (see Example 39).

$^1$H NMR (270 MHz; CDCl$_3$): 8.86–8.97 (m, 8H), 8.1 (d, 2H, J=8.6 Hz), 7.39 (m, 6H), 7.26 (d, 2H, J=8.6 Hz), 6.89 (m, 3H), 4.24 (t, 2H), 4.19 (t, 2H), 4.12 (t, 12H), 2.95 (s, 3H), 1.0–2.0 (m, 116H), 0.85 (t, 18H), −2.79 (s, 2H).

EXAMPLE 53

5-[4-(12-Methanesulfonyloxy-dodecyloxy)-phenyl]-10,15,20-tris-(3,5-dihexadecyloxy-phenyl)-porphyrin The title compound was prepared according to the method described in Example 41 above from 5-[4-(12-hydroxy-dodecyloxy)-phenyl]-10,15,20-tris-(3,5-dihexadecyloxy-phenyl)-porphyrin (see Example 40).

$^1$H NMR (270 MHz; CDCl$_3$): 8.89–8.99 (m, 8H), 8.13 (d, 2H, J=8.25 Hz), 7.42 (m, 6H), 7.29 (d, 2H, J=8.25 Hz), 6.92 (m, 3H), 4.21–4.26 (m, 4H), 4.15 (m, 12H), 2.97 (s, 3H), 1.1–2.0 (m, 188H), 0.89 (m, 18H), −2.75 (s, 2H).

EXAMPLE 54

5-[4-(6-but-3-Enyloxy-hexyloxy)-phenyl]-10,15,20-tris-(3,4,5-trihexyloxy-phenyl)-porphyrin 5-[4-(6-Methanesulfonyloxy-hexyloxy)-phenyl]-10,15,20-tris3,4,5-trihexyloxy-phenyl)-porphyrin (573mg, 0.33mmol, see Example 43) was heated to reflux in dry THF (20 ml). A solution of sodium butenoate (NaH (excess) in 3-buten-1-ol (1 equiv.)) was added causing the reaction mixture to turn deep green. The reaction was heated at reflux until the reaction was complete (ca. 3–5 hours). The mixture was cooled, water was added and the solution was extracted with diethyl ether. The organic phase was washed with brine, dried over MgSO$_4$, filtered and the filtrate evaporated under reduced pressure. Column chromatography on silica gel with petroleum ether (b.p. 40–60° C.):THF (10:1 by volume) yielded the title compound.

EXAMPLE 55

5-[4-(6-but-3-Enyloxy-hexyloxy)-phenyl]-10,15,20-tris-(3,4,5-tridecyloxy-phenyl)-porphyrin The title compound was prepared according to the method described in Example 54 above from 5-[4-(6-methanesulfonyloxy-hexyloxy)-phenyl]-10,15,20-tris-(3,4,5-tridecyloxy-phenyl)-porphyrin (see Example 44).

$^1$H NMR (270 MHz; CDCl$_3$): 8.85–8.94 (m, 8H), 8.09 (d, 2H, J=8.6 Hz), 7.49 (m, 6H), 7.27 (d, 2H, J=8.6 Hz), 5.9 (m, 1H), 5.04–5.16 (m, 2H), 4.29 (m, 8H), 4.08 (t, 12H), 3.53 (t, 4H), 2.38 (m, 2H), 1.2–2.1 (m, 152H), 0.91 (t, 9H), 0.83 (t, 18H), −2.79 (s, 2H).

EXAMPLE 56

5-[4-(6-but-3-Enyloxy-hexyloxy)-phenyl]-10,15,20-tris-(3,4,5-trihexadecyloxy-phenyl)-porphyrin The title compound was prepared according to the method described in Example 54 above from 5-[4-(6-methanesulfonyloxy-hexyloxy)-phenyl]-10,15,20-tris-(3,4,5-trihexadecyloxy-phenyl)-porphyrin (see Example 45).

$^1$H NMR (270 MHz; CDCl$_3$): 8.87–8.95 (m, 8H), 8.1 (d, 2H, J=7.92 Hz), 7.43 (s, 6H), 7.24 (d, 2H, J=7.92 Hz), 5.9 (m, 1H), 5.09–5.12 (m, 2H), 4.3 (m, 8H), 4.09 (t, 12H), 3.53 (t, 4H), 2.4 (m, 2H), 1.0–2.1 (m, 260H), 0.84–0.88 (m, 27H), −2.77 (s, 2H).

EXAMPLE 57

5-[4-(12-but-3-Enyloxy-dodecyloxy)-phenyl]-10,15,20-tris-(3,4,5-trihexyloxy-phenyl)-porphyrin The title compound was prepared according to the method described in Example 54 above from 5-[4-(12-methanesulfonyloxy-dodecyloxy)-phenyl]-10,15,20-tris-(3,4,5-trihexyloxy-phenyl)-porphyrin (see Example 46).

$^1$H NMR (270 MHz; CDCl$_3$): 8.86–8.94 (m, 8H), 8.1 (d, 2H, J=7.92 Hz), 7.42 (s, 6H), 7.3 (d, 2H, J=7.92 Hz), 5.83 (m, 1H), 5.01–5.12 (m, 2H), 4.3 (t, 6H), 4.28 (t, 2H), 4.09 (t, 12H), 3.46 (t, 2H), 3.43 (t, 2H), 2.33 (m, 2H), 1.1–2.0 (m, 92H), 0.99 (t, 9H), 0.86 (t, 18H), −2.78 (s, 2H).

EXAMPLE 58

5-[4-(12-but-3-Enyloxy-dodecyloxy)-phenyl]-10,15,20-tris-(3,4,5-tridecyloxy-phenyl)-porphyrin The title compound was prepared according to the method described in Example 54 above from 5-[4-(12- methanesulfonyloxy-dodecyloxy)-phenyl]-10,15,20-tris-(3, 4,5-tridecyloxy-phenyl)-porphyrin (see Example 41).

¹H NMR (270 MHz; CDCl₃): 8.87–8.95 (m, 8H), 8.11 (d, 2H, J=7.92 Hz), 7.43 (s, 6H), 7.27 (d, 2H, J=7.92 Hz), 5.8 (m, 1H), 5.01–5.11 (m, 2H), 4.31 (t, 6H), 4.25 (t, 2H), 4.09 (t, 12H), 3.45 (t, 2H), 3.42 (t, 2H), 2.33 (m, 2H), 1.0–2.0 (m, 164H), 0.91 (t, 9H), 0.84 (t, 18H), −2.77 (s, 2H).

EXAMPLE 59

5-[4-(12-but-3-Enyloxy-dodecyloxy)-phenyl]-10,15, 20-tris-(3,4,5-trihexadecyloxy-phenyl)-porphyrin The title compound was prepared according to the method described in Example 54 above from 5-[4-(12-methanesulfonyloxy-dodecyloxy)-phenyl]-10,15,20-tris-(3, 4,5-trihexadecyloxy-phenyl)-porphyrin (see Example 47).

¹H NMR (270 MHz; CDCl₃): 8.87–8.93 (m, 8H), 8.09 (d, 2H, J=7.92 Hz), 7.42 (s, 6H), 7.27 (d, 2H, J=7.92 Hz), 5.9 (m, 1H), 5.01–5.12 (m, 2H), 4.29 (m, 8H), 4.08 (t, 12H), 3.47 (t, 2H), 3.43 (t, 2H), 2.37 (m, 2H), 1.0–2.0 (m, 272H), 0.83–0.87 (m, 27H), −2.79 (s, 2H).

EXAMPLE 60

5-[4-(16-but-3-Enyloxy-hexadecyloxy)-phenyl]-10, 15,20-tris-(3,4,5-tridecyloxy-phenyl)-porphyrin The title compound was prepared according to the method described in Example 54 above from 5-[4-(16-methanesulfonyloxy-hexadecyloxy)-phenyl]-10,15,20-tris-(3,4,5-tridecyloxy-phenyl)-porphyrin (see Example 48).

EXAMPLE 61

5-[4-(16-but-3-Enyloxy-hexadecyloxy)-phenyl]-10, 15,20-tris-(3,4,5-trihexadecyloxy-phenyl)-porphyrin The title compound was prepared according to the method described in Example 54 above from 5-[4-(16-methanesulfonyloxy-hexadecyloxy)-phenyl]-10,15,20-tris-(3,4,5-trihexadecyloxy-phenyl)-porphyrin (see Example 49).

EXAMPLE 62

5-[4-(12-but-3-Enyloxy-dodecyloxy)-phenyl]-10,15, 20-tris-(3,5-dihexyloxy-phenyl)-porphyrin The title compound was prepared according to the method described in Example 54 above from 5-[4-(12-methanesulfonyloxy-dodecyloxy)-phenyl]-10,15,20-tris-(3, 5-dihexyloxy-phenyl)-porphyrin (see Example 50).

¹H NMR (270 MHz; CDCl₃): 8.85–8.96 (m, 8H), 8.09 (d, 2H, J8.25 Hz), 7.38 (m, 6H), 7.25 (d, 2H, J=8.25 Hz), 6.88 (m, 3H), 5.81 (m, 1H), 5.0–5.11 (m, 2H), 4.22 (t, 2H), 4.11 (t, 12H), 3.44 (t, 2H), 3.40 (t, 2H), 2.32 (m, 2H), 1.1–2.0 (m, 68H), 0.87 (m, 18H), −2.8 (s, 2H).

EXAMPLE 63

5-[4-(6-but-3-Enyloxy-hexyloxy)-phenyl]-10,15,20-tris-(3,5-didecyloxy-phenyl)-porphyrin The title compound was prepared according to the method described in Example 54 above from 5-[4-(6-methanesulfonyloxy-hexyloxy)-phenyl]-10,15,20-tris-(3,5-didecyloxy-phenyl)-porphyrin (see Example 51).

¹H NMR (270 MHz; CDCl₃): 8.86–8.95 (m, 8H), 8.1 (m, 2H), 7.37 (m, 6H), 7.25 (m, 2H), 6.88 (m, 3H), 5.85 (m, 1H), 5.0–5.2 (m, 2H), 4.23 (m, 2H), 4.11 (m, 12H), 3.5 (m, 4H), 2.4 (m, 2H), 1.0–2.0 (m, 104H), 0.84 (m, 18H), −2.8 (s, 2H).

EXAMPLE 64

5-[4-(12-but-3-Enyloxy-dodecyloxy)-phenyl]-10,15, 20-tris-(3,5-didecyloxy-phenyl)-porphyrin The title compound was prepared according to the method described in Example 54 above from 5-[4-(12-methanesulfonyloxy-dodecyloxy)-phenyl]-10,15,20-tris-(3, 5-didecyloxy-phenyl)-porphyrin (see Example 52).

¹H NMR (270 MHz; CDCl₃): 8.86–8.97 (m, 8H), 8.1 (d, 2H, J=8.6 Hz), 7.38 (m, 6H), 7.26 (d, 2H, J=8.6 Hz), 6.89 (m, 3H), 5.8 (m, 1H), 4.98–5.12 (m, 2H), 4.23 (t, 2H), 4.11 (t, 12H), 3.45 (t, 2H), 3.41 (t, 2H), 2.3 (m, 2H), 1.0–2.0 (m, 116H), 0.84 (m, 18H), −2.79 (s, 2H).

EXAMPLE 65

5-[4-(12-but-3-Enyloxy-dodecyloxy)-phenyl]-10,15, 20-tris-(3,5-dihexadecyloxy-phenyl)-porphyrin The title compound was prepared according to the method described in Example 54 above from 5-[4-(12-methanesulfonyloxy-dodecyloxy)-phenyl]-10,15,20-tris-(3, 5-dihexadecyloxy-phenyl)-porphyrin (see Example 53).

¹H NMR (270 MHz; CDCl₃): 8.86–8.95 (m, 8H), 8.1 (d, 2H, J=7.92 Hz), 7.38 (m, 6H), 7.26 (d, 2H, J=7.92 Hz), 6.88 (m, 3H), 5.8 (m, 1H), 4.98–5.12 (m, 2H), 4.23 (t, 2H), 4.11 (t, 12H), 3.45 (t, 2H), 3.41 (t, 2H), 2.33 (m, 2H), 1.0–2.0 (m, 188H), 0.85 (m, 18H), −2.79 (s, 2H).

EXAMPLE 66

5,5'-{4,4'-[12,12'-Dithiobis-(dodecyloxy)-phenyl]}-10,10',15,15',20,20'-hexakis-(3,4,5-tridecyloxy-phenyl)-diporphyrin 5-[4-(12-Methanesulfonyloxy-dodecyloxy)-phenyl]-10, 15,20-tris-(3,4,5-tridecyloxy-phenyl)-porphyrin (159 mg, 0.07 mmol, see Example 41) and an excess of thiourea were heated at reflux in 1-pentanol (5 ml) until no starting material remained (approx. 1 hour). Ethanol (2 ml) was added followed by aqueous NaOH (10% w/v, 2 ml) and heating at reflux was continued for a further 5 minutes. The solution was allowed to cool and then added to dilute aqueous HCl (10% v/v). The reaction mixture was extracted with dichloromethane, the organic extracts washed with brine, dried over MgSO₄, filtered and evaporated under reduced pressure. Column chromatography on silica gel with petroleum ether (b.p. 40–60° C.):THF (4:1 by volume) yielded the title compound.

¹H NMR (270 MHz; CDCl₃): 8.87–9.0 (m, 8H), 8.11 (d, J=8 Hz, 2H), 7.44 (s, 6H), 7.3 (d, J=8 Hz, 2H), 4.31 (t, 8H), 4.27 (t, 2H), 4.1 (t, 12H), 2.71 (t, 2H), 1.2–2.05 (m, 164H), 0.92 (t, 9H), 0.85 (t, 18H), −2.76 (s, 2H). $\lambda_{max}$ (nm, THF). 650.5, 592.5, 552.5, 516.0, 423.0.

EXAMPLE 67

5,5'-{4,4'-[12,12'-Dithiobis-(dodecyloxy)-phenyl]}-10,10',15,15',20,20'-hexakis-(3,4,5-tridecyloxy-phenyl)-diporphyrinato Zinc 5,5'-{4,4'-[12,12'-Dithiobis-(dodecyloxy)-phenyl]}-10, 10',15,15',20,20'-hexakis-(3,4,5-tridecyloxy-phenyl)-diporphyrin (114 mg, 25 μmol, see Example 66) was heated to reflux in THF (5 ml). An excess of zinc acetate dihydrate was added and heating at reflux was continued for 30 mins. The solvent was evaporated under reduced pressure and the residue obtained was purified by chromatography using a short column of silica gel which was eluted with petroleum ether (b.p. 40–60° C.):THF (4:1 by volume) to yield the title compound.

$^1$H NMR (270 MHz; CDCl$_3$): 8.9–9.1 (m, 8H), 8.1 (d, J=8 Hz, 2H), 7.42 (s, 6H), 7.27 (d, J=8 Hz, 2H), 4.29 (t, 8H), 4.24 (t, 2H), 4.09 (t, 12H), 2.67 (t, 2H), 1.2–2.05 (m, 164H), 0.91 (t, 9H), 0.83 (t, 18H). $\lambda_{max}$ ($\epsilon \times 10^5$): 598.0 (0.12), 557.0 (0.38), 427.5 (12.6), 406.5 (0.86) (nm, THF). MALDI-MS: 4601 [M$^+$], 2300 [M$^{2+}$, 100%]. Found: C, 76.39%; H, 10.39%; N, 2.12%; C$_{292}$H$_{462}$N$_8$O$_{20}$S$_2$Zn$_2$ requires: C, 76.25%; H, 10.12%; N, 2.44%.

EXAMPLE 68

5,5'-{4,4'-[12,12'-Dithiobis-(dodecyloxy)-phenyl]}-10,10',15,15',20,20'-hexakis-(3,4,5-tridecyloxy-phenyl)-diporphyrinato Magnesium 5,5'-{4,4'-[12,12'-Dithiobis-(dodecyloxy)-phenyl]}-10,10',15,15',20,20'-hexakis-(3,4,5-tridecyloxy-phenyl) diporphyrin (100 mg, 22 μmol, see Example 66) was heated for 4 hours at reflux in dry pyridine (10 ml) under an atmosphere of dry nitrogen in the presence of an excess of magnesium perchlorate. The mixture was cooled and fractionated between water and diethyl ether. The organic phase was washed with dilute aqueous HCl and brine, dried over MgSO$_4$, and evaporated under reduced pressure.

Column chromatography using a short column of silica gel which was eluted with petroleum ether (b.p. 40–60° C.):THF (10:1 by volume) yielded the title compound.

$^1$H NMR (270 MHz; CDCl$_3$): 8.8–9.1 (m, 8M), 7.25–7.5 (m, 8H), 3.9–4.4 (m, 22H), 2.7 (t, 2H), 1.1–2.1 (m, 164H), 0.8–1.0 (m, 27H). $\lambda_{max}$ ($\epsilon \times 10^5$) 615.0 (0.23), 569.0 (0.26), 432.0 (10.77) (nm, THF). MALDI-MS: 4518 [M$^+$, 100%], 2260 [M$^{2+}$]. Found: C, 77.39%; H, 10.28%; N, 2.42%; C$_{292}$H$_{462}$N$_8$O$_{20}$S$_2$Mg$_2$ requires: C, 77.63%; H, 10.31%; N, 2.48%.

EXAMPLE 69

5-[4-(6-but-3-Enyloxy-hexyloxy)-phenyl]-10,15,20-tris-(3,4,5-trihexyloxy-phenyl)-porphyrinato Zinc The title compound was prepared according to the method described in Example 67 above from 5-[4-(6-but-3-enyloxy-hexyloxy)-phenyl]-10,15,20-tris-(3,4,5-trihexyloxy-phenyl)-porphyrin (see Example 54).

$^1$H NMR (270 MHz; CDCl$_3$): 8.97–9.05 (m, 8H), 8.1 (d, 2H, J=8.25 Hz), 7.43 (s, 6H), 7.27 (d, 2H, J=8.25 Hz), 5.85 (m, 1H), 5.05–5.17 (m, 2H), 4.3 (t, 6H), 4.27 (t, 2H), 4.08 (t, 12H), 3.53 (m, 4H), 2.39 (m, 2H), 1.2–2.0 (m, 78H), 0.99 (t, 9H), 0.86 (t, 18H). $\lambda_{max}$ ($\epsilon \times 10^5$): 406.0 (0.51), 427.0 (6.6), 557.0 (0.26), 597.0 (0.12) (nm, THF). FAB-MS: 1749 [M$^+$]. Found: C, 74.22%; H, 8.83%; N, 3.07%; C$_{108}$H$_{154}$N$_4$O$_{11}$Zn requires: C, 74.13%; H, 8.87%; N, 3.2%.

EXAMPLE 70

5-[4-(6-but-3-Enyloxy-hexyloxy)-phenyl]-10,15,20-tris-(3,4,5-tridecyloxy-phenyl)-porphyrinato Zinc The title compound was prepared according to the method described in Example 67 above from 5-[4-(6-but-3-enyloxy-hexyloxy)-phenyl]-10,15,20-tris-(3,4,5-tridecyloxy-phenyl)-porphyrin (see Example 55).

$^1$H NMR (270 MHz; CDCl$_3$): 8.94–9.02 (m, 8H), 8.07 (d, 21H, J=8.6 Hz), 7.4 (s, 6H), 7.25 (d, 2H, J=8.6 Hz), 5.86 (m, 1H), 5.07–5.14 (m, 2H), 4.27 (m, 8H), 4.05 (t, 12H), 3.5 (m, 4H), 2.37 (m, 2H), 1.2–2.1 (m, 152H), 0.89 (t, 9H), 0.81 (t, 18H). $\lambda_{max}$ ($\epsilon \times 10^5$): 406.0 (0.59), 427.0 (6.8), 557.0, (0.31), 597.0 (0.17) (nm, THF). FAB-MS: 2253.5 [M$^+$]. Found: C, 76.86%; H, 10.24%; N, 2.31%; C$_{144}$H$_{226}$N$_4$O$_{11}$, Zn requires: C, 76.71%; H, 10.10%; N, 2.48%.

EXAMPLE 71

5-[4-(6-but-3-Enyloxy-hexyloxy)-phenyl]-10,15,20-tris-(3,4,5-trihexadecyloxy-phenyl)-porphyrinato Zinc The title compound was prepared according to the method described in Example 67 above from 5-[4-(6-but-3-enyloxy-hexyloxy)-phenyl]-10,15,20-tris-(3,4,5-trihexadecyloxy-phenyl)-porphyrin (see Example 56).

$^1$H NMR (270 MHz; CDCl$_3$): 8.91–9.0 (m, 8H), 8.09 (d, 2H, J=7.92 Hz), 7.42 (s, 6H), 7.25 (d, 2H, J=7.92 Hz), 5.88 (m, 1H), 5.02–5.18 (m, 2H), 4.3 (m, 8H), 4.09 (t, 12H), 3.5 (m, 4H), 2.38 (m, 2H), 1.0–2.0 (m, 260H), 0.82–0.89 (m, 27H). $\lambda_{max}$ ($\epsilon \times 10^5$): 406.0 (0.5), 428.0 (6.86), 557.0 (0.23), 597.0 (0.09) (nm, THF). MALDI-MS: 3011 [M$^+$]. Mpt: 48° C. Found: C, 78.59%; H, 11.08%; N, 1.82%; C$_{198}$H$_{334}$N$_4$O$_{11}$Zn requires: C, 78.95%; H, 11.18%; N, 1.86%.

EXAMPLE 72

5-[4-(12-but-3-Enyloxy-dodecyloxy)-phenyl]-10,15,20-tris-(3,4,5-trihexyloxy-phenyl)-porphyrinato Zinc The title compound was prepared according to the method described in Example 67 above from 5-[4-(12-but-3-enyloxy-dodecyloxy)-phenyl]-10,15,20-tris-(3,4,5-trihexyloxy-phenyl)-porphyrin (see Example 57).

$^1$H NMR (270 MHz; CDCl$_3$): 9.01–9.09 (m, 8H), 8.13 (d, 2H, J=8.6 Hz), 7.47 (s, 6H), 7.3 (d, 2H, J=8.6 Hz), 5.81 (m, 1H), 5.03–5.12 (m, 2H), 4.33 (t, 6H), 4.28 (t, 2H), 4.11 (t, 12H), 3.37 (t, 2H), 3.33 (t, 2H), (m, 2H), 1.2–2.1 (m, 92H), 1.03 (t, 9H), 0.9 (t, 18H). $\lambda_{max}$ ($\epsilon \times 10^5$): 406.0 (0.48), 428.0 (6.52), 557.0 (0.23), 597.0 (0.09) (nm, THF). FAB-MS: 1835.5 [M$^+$]. Found: C, 74.99%; H, 8.85%; N, 2.97%; C$_{114}$H$_{166}$N$_4$O$_{11}$Zn requires: C, 74.66%; H, 9.12%; N, 3.05%.

EXAMPLE 73

5-[4-(12-but-3-Enyloxy-dodecyloxy)-phenyl]-10,15,20-tris-(3,4,5-tridecyloxy-phenyl)-porphyrinato Zinc The title compound was prepared according to the method described in Example 67 above from 5-[4-(12-but-3-enyloxy-dodecyloxy)-phenyl]-10,15,20-tris-(3,4,5-tridecyloxy-phenyl)-porphyrin (see Example 58).

$^1$H NMR (270 MHz; CDCl$_3$): 8.96–9.04 (m, 8H), 8.09 (d, 2H, J=8.6 Hz), 7.43 (s, 6H), 7.26 (d, 2H, J=8.6 Hz), 5.79 (m, 1H), 5.63–5.1 (m, 2H), 4.3 (t, 6H), 4.27 (t, 2H), 4.08 (t, 12H), 3.39 (t, 2H), 3.35 (t, 2H), 2.27 (m, 2H), 1.2–2.0 (m, 164H), 0.91 (t, 9H), 0.83 (t, 18H). $\lambda_{max}$ ($\epsilon \times 10^5$): 406.0 (0.51), 428.0 (7.14), 557.0 (0.24), 597.0 (0.10) (nm, THF). FAB-MS: 2338.5 [M$^+$]. Found: C, 77.47%; H, 10.35%; N, 2.20%; C150H$_{238}$N$_4$O$_{11}$Zn requires: C, 77.03%; H, 10.26%; N, 2.39%.

EXAMPLE 74

5-[4-(12-but-3-Enyloxy-dodecyloxy)-phenyl]-10,15,20-tris-(3,4,5-trihexadecyloxy-phenyl)-porphyrinato Zinc The title compound was prepared according to the method described in Example 67 above from 5-[4-(12-but-3- enyloxy-dodecyloxy)-phenyl]-10,15,20-tris-(3,4,5-trihexadecyloxy-phenyl)-porphyrin (see Example 59).

$^1$H NMR (270 MHz; CDCl$_3$): 8.96–9.04 (m, 8H), 8.09 (d, 2H, J=8.25 Hz), 7.42 (s, 6H), 7.27 (d, 2H, J=8.25 Hz), 5.8 (m, 1H), 5.0–5.1 (m, 2H), 4.29 (m, 8H), 4.07 (t, 12H), 3.43 (t, 2H), 3.39 (t, 2H), 2.3 (m, 2H), 1.0–2.05 (m, 272H), 0.85–0.87 (m, 27H). $\lambda_{max}$ ($\epsilon \times 10^5$): 406.0 (0.54), 427.0 (6.6), 557.0 (0.28), 597.0 (0.14) (nm, THF). MALDI-MS: 3096 [M$^+$]. Found: C, 78.96%; H, 11.25%; N, 1.75%; C$_{204}$H$_{346}$N$_4$O$_{11}$Zn requires: C, 79.13%; H, 11.26%; N, 1.81%.

EXAMPLE 75

5-[4-(16-but-3-Enyloxy-hexadecyloxy)-phenyl]-10, 15,20-tris-(3,4,5-tridecyloxy-phenyl)-porphyrinato Zinc The title compound was prepared according to the method described in Example 67 above from 5-[4-(16-but-3-enyloxy-hexadecyloxy)-phenyl]-10,15,20-tris-(3,4,5-tridecyloxy-phenyl)-porphyrin (see Example 60).

$^1$H NMR (270 MHz; CDCl$_3$): 9.0–9.09 (m, 8H), 8.12 (d, 2H, J=8.25 Hz), 7.46 (s, 6H), 7.29 (d, 2H, J=8.25 Hz), 5.9 (m, 1H), 5.0–5.2 (m, 2H), 4.33 (m, 8H), 4.1 (t, 12H), 3.29 (t, 2H), 3.25 (t, 2H), 2.1 (m, 2H), 1.0–2.0 (m, 172H), 0.87–0.95 (m, 27H). $\lambda_{max}$ ($\epsilon \times 10^5$): 406.0 (0.47), 427.0 (6.71), 557.0 (0.25), 598.0 (0.12) (nm, THF). FAB-MS: 2393 [M$^+$, weak]. Found: C, 77.27%; H, 10.29%; N, 2.04%; C$_{154}$H$_{246}$N$_4$O$_{11}$Zn requires: C, 77.23%; H, 10.35%; N, 2.34%.

EXAMPLE 76

5-[4-(16-but-3-Enyloxy-hexadecyloxy)-phenyl]-10, 15,20-tris-(3,4,5-trihexadecyloxy-phenyl)-porphyrinato Zinc The title compound was prepared according to the method described in Example 67 above from 5-[4-(16-but-3-enyloxy-hexadecyloxy)-phenyl]-10,15,20-tris-(3,4,5-trihexadecyloxy-phenyl)-porphyrin (see Example 61).

$^1$H NMR (270 MHz; CDCl$_3$): 8.89–8.97 (m, 8H), 8.02 (d, 2H), 7.35 (s, 6H), 7.3 (d, 2H), 5.8 (m, 1H), 4.8–5.0 (m, 2H), 4.22 (m, 8H), 3.99 (t, 12H), 3.28 (t, 2H), 3.23 (t, 2H), 1.0–2.2 (m, 282H), 0.78 (m, 27H). $\lambda_{max}$ ($\epsilon \times 10^5$): 406.0 (0.56), 427.0 (7.28), 557.0 (0.26), 598.0 (0.11) (nm, THF). MALDI-MS: 3152 [M$^+$].

EXAMPLE 77

5-[4-(6-but-3-Enyloxy-hexyloxy)-phenyl]-10,15,20-tris-(3,4,5-tridecyloxy-phenyl)-porphyrinato Magnesium The title compound was prepared according to the method described in Example 68 above from 5-[4-(6-but-3-enyloxy-hexyloxy)-phenyl]-10,15,20-tris-(3,4,5-tridecyloxy-phenyl)-porphyrin (see Example 55).

$^1$H NMR (270 MHz; CDCl$_3$): 8.87–8.96 (m, 8H), 8.09 (d, 2H, J=8.6 Hz), 7.41 (s, 6H), 7.1 (d, 2H, J=8.6 Hz), 5.71 (m, 1H), 4.97–5.05 (m, 2H), 4.26 (t, 6H), 4.22 (t, 2H), 4.04 (t, 12H), 3.25 (t, 4H), 2.14 (m, 2H), 1.2–2.0 (m, 152H), 0.88 (t, 4H), 0.81 (t, 18H). $\lambda_{max}$ ($\epsilon \times 10^5$): 432.0 (6.1), 571.0 (0.22), 614.0 (0.18) (nm, THF). FAB-MS: 2213.5 [M$^+$]. Found: C, 77.77%; H, 10.25%; N, 2.34%; C$_{144}$H$_{226}$N$_4$O$_{11}$Mg requires: C, 78.13%; H, 10.29%; N, 2.53%.

EXAMPLE 78

5-[4-(12-but-3-Enyloxy-dodecyloxy)-phenyl]-10,15, 20-tris-(3,5-dihexyloxy-phenyl)-porphyrinato Zinc The title compound was prepared according to the method described in Example 67 above from 5-[4-(12-but-3-enyloxy-dodecyloxy)-phenyl]-10,15,20-tris-(3,5-dihexyloxy-phenyl)-porphyrin (see Example 62).

$^1$H NMR (270 MHz; CDCl$_3$): 8.97–9.07 (m, 8H), 8.1 (d, 2H, J=8.25 Hz), 7.37 (m, 6H), 7.24 (d, 2H, J=8.25 Hz), 6.83 (m, 3H), 5.74 (m, 1H), 4.98–5.07 (m, 2H), 4.21 (t, 2H), 4.07 (t,12H), 3.26 (t, 2H), 3.22 (t, 2H), 2.19 (m, 2H), 1.1–2.0 (m, 68H), 0.89 (t, 18H). $\lambda_{max}$ ($\epsilon \times 10^5$): 405.0 (0.63), 425.0 (9.45), 556.0 (0.29), 595.0 (0.08) (nm, THF). FAB-MS: 1533 [M$^+$]. Found: C, 75.47%; H, 8.61%; N, 3.38%; C$_{96}$H$_{130}$N$_4$O$_8$Zn requires: C, 75.19%; H, 8.54%; N, 3.65%.

EXAMPLE 79

5-[4-(6-but-3-Enyloxy-hexyloxy)-phenyl]-10,15,20-tris-(3,5-didecyloxy-phenyl)-porphyrinato Zinc The title compound was prepared according to the method described in Example 67 above from 5-[4-(6-but-3-enyloxy-hexyloxy)-phenyl]-10,15,20-tris-(3,5-didecyloxy-phenyl)-porphyrin (see Example 63).

$^1$H NMR (270 MHz; CDCl$_3$): 8.96–9.06 (m, 8H), 8.09 (d, 2H, J=8.25 Hz), 7.35 (m, 6H), 7.21 (d, 2H, J=8.25 Hz), 6.81 (m, 3H), 5.76 (m, 1H), 5.0–5.09 (m, 2H), 4.18 (t, 2H), 4.06 (t, 12H), 3.29 (m, 4H), 2.2 (m, 2H), 1.1–2.0 (m, 104H), 0.84 (t, 18H). $\lambda_{max}$ ($\epsilon \times 10^5$): 404.0 (0.57), 425.0 (8.86), 556.0 (0.28), 595.0 (0.08) (nm, THF). FAB-MS: 1786.3 [M$^+$]. Found: C, 76.54%; H, 9.37%; N, 2.98%; C$_{114}$H$_{166}$N$_4$O$_8$Zn requires: C, 76.67%; H, 9.37%; N, 3.14%.

EXAMPLE 80

5-[4-(12-but-3-Enyloxy-dodecyloxy)-phenyl]-10,15, 20-tris-(3,5-didecyloxy-phenyl)-porphyrinato Zinc The title compound was prepared according to the method described in Example 67 above from 5-[4-(12-but-3-enyloxy-dodecyloxy)-phenyl]-10,15,20-tris-(3,5-didecyloxy-phenyl)-porphyrin (see Example 64).

$^1$H NMR (270 MHz; CDCl$_3$): 8.95–9.05 (m, 8H), 8.09 (d, 2H, J=8.6 Hz), 7.36 (m, 6H), 7.24 (d, 2H, J=8.6 Hz), 6.84 (m, 3H), 5.8 (m, 1H), 5.02–5.12 (m, 2H), 4.22 (t, 2H), 4.08 (t, 12H), 3.26–3.35 (m, 4H), 2.26 (m, 2H), 1.1–2.1 (m, 116H), 0.84 (t, 18H). $\lambda_{max}$ ($\epsilon \times 10^5$): 404.0 (0.54), 425.0 (7.59), 556.0 (0.25), 595.0 (0.07) (nm, THF). FAB-MS: 1871.5 [M$^+$]. Found: C, 77.18%; H, 9.71%; N, 2.85%; C$_{120}$H$_{178}$N$_4$O$_8$Zn requires: C, 77.07%; H, 9.59%; N, 2.99%.

EXAMPLE 81

5-[4-(12-but-3-Enyloxy-dodecyloxy)-phenyl]-10,15, 20-tris-(3,5-dihexadecyloxy-phenyl)-porphyrinato Zinc The title compound was prepared according to the method described in Example 67 above from 5-[4-(12-but-3-enyloxy-dodecyloxy)-phenyl]-10,15,20-tris-(3,5-dihexadecyloxy-phenyl)-porphyrin (see Example 65).

$^1$H NMR (270 MHz; CDCl$_3$): 8.92–9.02 (m, 8H), 8.07 (d, 2H, J=8.25 Hz), 7.35 (m, 6H), 7.21 (d, 2H, J=8.25 Hz), 6.83 (m, 3H), 5.74 (m, 1H), 4.96–5.06 (m, 2H), 4.2 (t, 2H), 4.07 (t, 12H), 3.3 (t, 2H), 3.26 (t, 2H), 2.21 (m, 2H), 1.1–2.1 (m, 188H), 0.83 (t, 18H). $\lambda_{max}$ ($\epsilon \times 10^5$): 404.0 (0.53), 425.0 (7.07), 556.0 (0.24), 595.0 (0.08) (nm, THF). FAB-MS: 2374.5 [M$^+$]. Found: C, 78.62%; H, 10.51%; N, 2.12%; C$_{156}$H$_{250}$N$_4$O$_8$Zn requires: C, 78.89%; H, 10.61%; N, 2.36%.

EXAMPLE 82

Preparation of a Self-assembled Monolayer on a Gold Surface a) Preparation of the Base Solution for Cleaning the Glass Slides Analytical grade potassium hydroxide (100 g) was dissolved in Millipore® water (100 ml) and the solution was made up to 250 ml with Distol grade methanol.

b) Preparation of the Glass Slides

1. The slides were wiped with a Kimwipe® tissue paper and rinsed with Distol grade methanol.
2. The slides were immersed in the base solution prepared as described above for a minimum of 12 hours.
3. The slides were washed with Millipore® water and dried in a stream of propan-2-ol at reflux.

c) Gold Deposition

A layer of gold (ca. 45 nm) was deposited on the slides using an Edwards 306 vacuum evaporator. A thin layer of chromium (ca. 1 nm) was initially deposited on the slides prior to the deposition of the gold to improve the adhesion of the gold to the slide.

d) Assembly of the Monolayer

A solution of 5,5'-{4,4'-[12,12'-dithiobis-(dodecyloxy)-phenyl]}-10,10',15,15',20,20'-hexakis-(3,4,5-tridecyloxy-phenyl)-diporphyrinato zinc (24.99 mg, see Example 67) in spectroscopic grade cyclohexane (100 ml) was prepared. A gold coated slide prepared according to the method of Example 82 (c) above and it was immersed in the diporphyrinato zinc cyclohexane solution for 24 hours. The slide was then rinsed with cyclohexane until the washings were colourless.

RAIR spectra of the slides were obtained using a blank gold coated slide to record the background.

EXAMPLE 83

Preparation of Porphyrin-doped Silicone Rubber Films

A solution of 1.0–3.0 mg of each of the title compounds of Examples 69 to 81 above in 1 ml xylene was prepared.

Procedure 1: Components for MED-6640 film preparation were obtained from Nusil Technology—Europe. Solution A (1.05 ml) and solution B (1 ml) were mixed with stirring. The solution of the respective porphyrin of Examples 69 to 81 (see above) in xylene (50 μl) was added. Portions of the mixture were deposited onto microscope cover slips (13 mm diameter) which were placed in an oven and heated to 40° C. for 2 hrs. The temperature was gradually raised to 150° C. and the slides were kept at this temperature for 15 mins and then allowed to cool.

Procedure 2: The procedure 1 was repeated using solution A (1.025 ml), solution B (1ml) and the solution of the respective porphyrin in xylene (25 μl).

EXAMPLE 84

Fluorescence Quantum Yields

The emission spectra were recorded using a Spex Fluorolog 3, excitation wavelength=355 nm, emission 550–800 nm, with a bandpass of 2 nm. A spectrum was recorded for each of the title compounds of Examples 67 to 81. Spectra were also recorded for meso-tetraphenylporphyrin (TPP), zinc tetraphenylporphyrin (Zn TPP), and magnesium tetraphenylporphyrin (Mg TPP) and were found to be within 5% error of reference values.

The fluorescence quantum yield for each of the title compounds of Examples 67 to 81 was determined by measuring the integral of the corrected emission spectra for each compound and calculated relative to TPP=0.11 (*Handbook of Photochemistry* Ed 2, Murov, Carmichael and Hug, Dekker 1993). The fluorescence quantum yield for each of the title compounds of Examples 67 to 81 are listed in Table 1; values for Zn TPP and Mg TPP are included in Table 1 for reference but they were not measured in this work.

TABLE 1

Fluorescence Quantum Yields

| Compound/Example | Quantum yield of fluorescence, relative to TPP = 0.11 |
| --- | --- |
| TPP* | 0.11 |
| Zn TPP* | 0.04 |
| Mg TPP* | 0.15 |
| 67 | 0.04 |
| 68 | 0.10 |
| 69 | 0.04 |
| 70 | 0.04 |
| 71 | 0.04 |
| 72 | 0.04 |
| 73 | 0.04 |
| 74 | 0.04 |
| 75 | 0.04 |
| 76 | 0.03 |
| 77 | 0.14 |
| 78 | 0.04 |
| 79 | 0.04 |
| 80 | 0.04 |
| 81 | 0.04 |

*From Handbook of Photochemistry Ed 2, Murov, Carmichael and Hug, Dekker (1993).

EXAMPLE 85

Singlet Oxygen Quantum Yields

A stock solution of each of the title compounds of Examples 67 to 81 was prepared by dissolving a small sample of the respective title compound in approximately 5 ml of toluene (Fisher Scientific, Analytical grade). The exact concentrations of the stock solution was not determined.

A working solution of each of the title compounds of Examples 67 to 81 was prepared by diluting the respective stock solution with toluene to give an absorbance of 0.100±0.005 at 355 nm when placed in a ultraviolet/visible spectrometer (ATI-Unicam UV-2) compared to a reference cell containing the pure toluene solvent. The ultraviolet/visible spectrum of each sample was also recorded over the range 300–700 nm. The final concentration of each of the respective working solutions was estimated by reference to the determined UV extinction coefficient; each working solution had a concentration in the range 5–10 μmol dm$^{-3}$.

Figure 2:
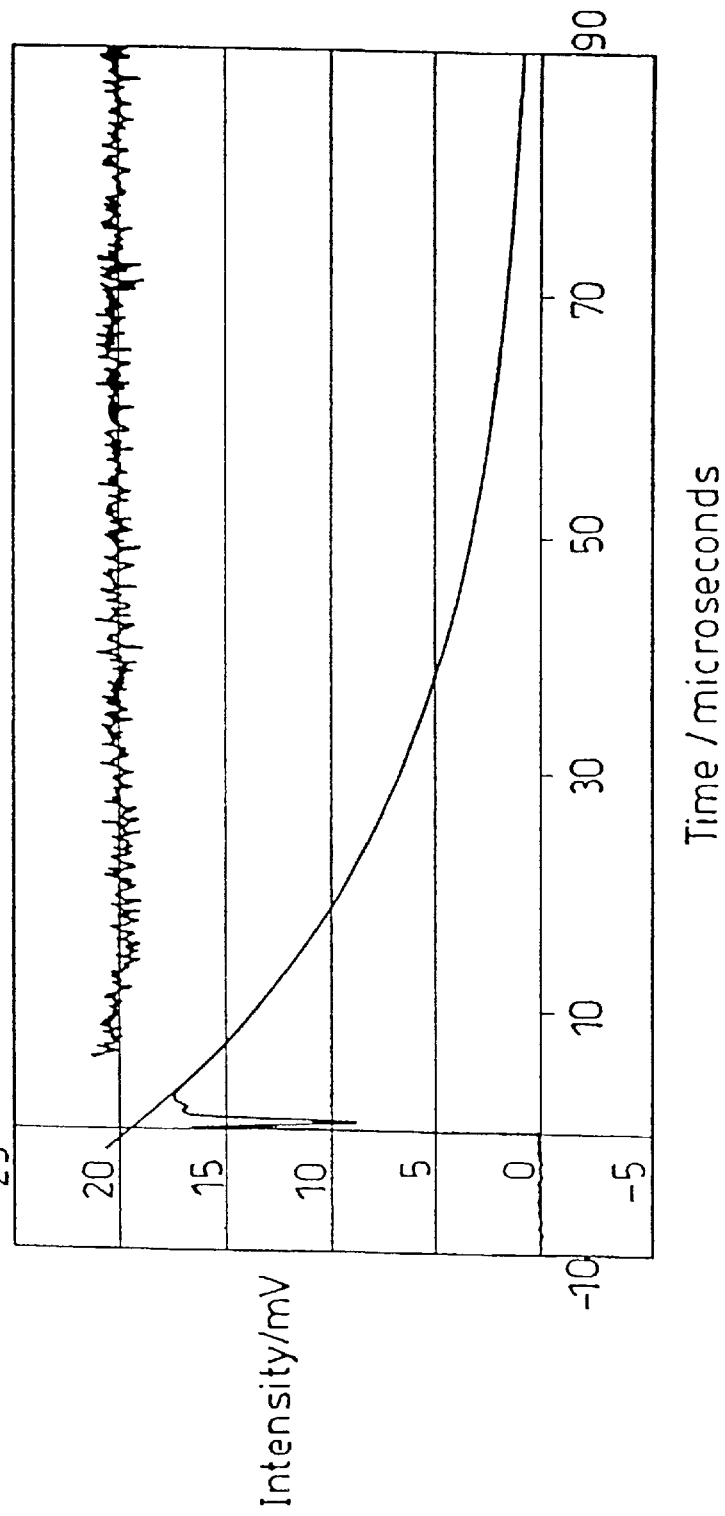
FIG. 2 is a typical decay and fitted curve for the title compound of Example 78 in toluene excited at 355 nm using a pulse energy of 365 μJ.

All of the data were recorded at ambient temperature, 20–23° C., and the solutions were aerated. The singlet oxygen emission decay was recorded for each sample using 5 laser energies and the data for each measurement were fitted to an exponential decay of the form I(t)=A.exp(-t/τ), where I(t) is the measured intensity of singlet oxygen phosphorescence at time t, A is the intensity extrapolated back to t=0 (ie when the laser fires), and τ is the lifetime of singlet oxygen. A typical decay for the title compound of Example 78 in toluene excited at 355 nm using a pulse energy of 365 μJ, where A=19.6 and τ=27.8 μs, is shown in FIG. 2.

Figure 3:
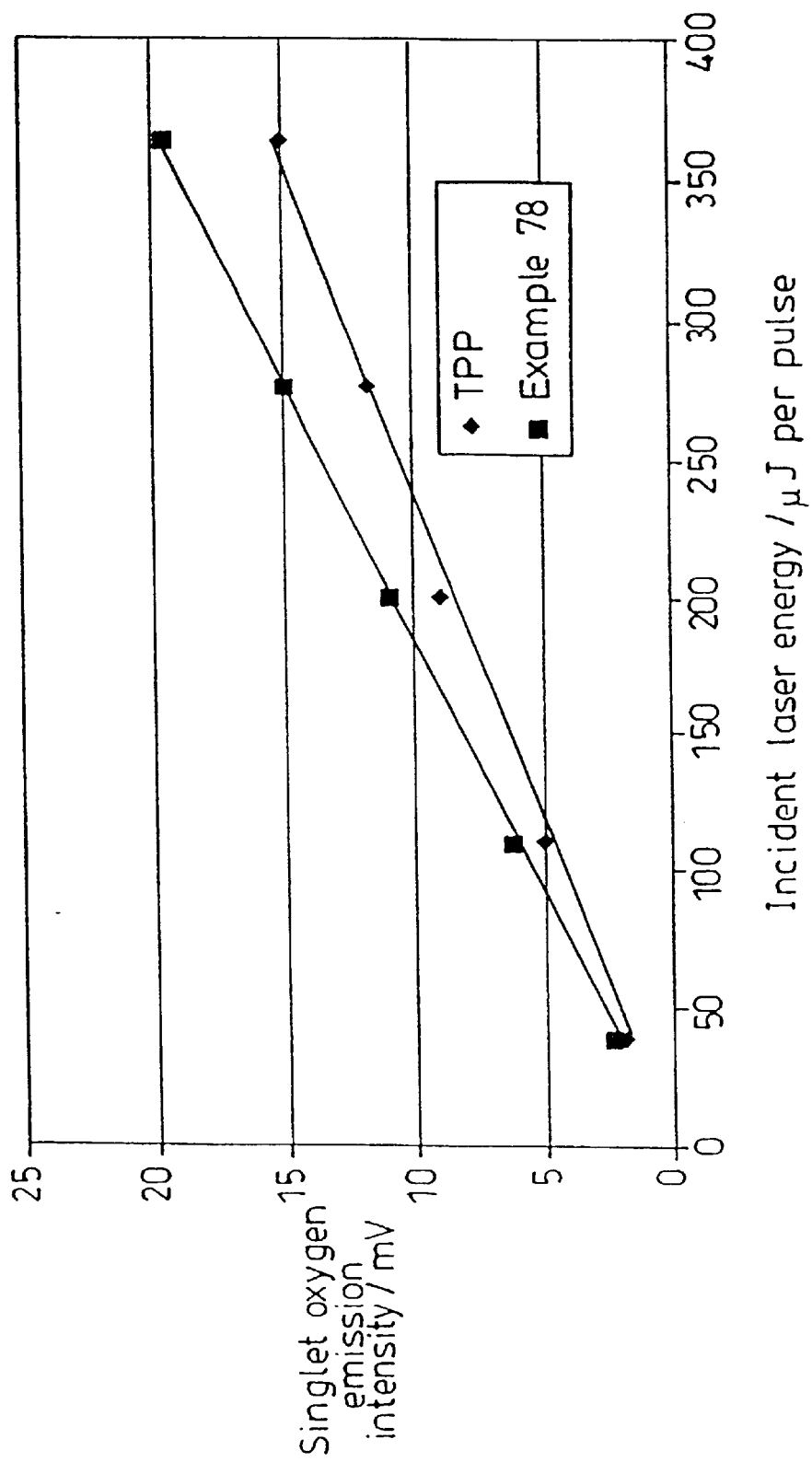
FIG. 3 is a plot showing the linear relationship between the singlet oxygen emission intensity and the laser energy for the title compound of Example 78 and meso-tetraphenyl porphyrin (TPP).

A plot of A versus the incident laser energy was drawn for each sample and the slope determined. The slope of such a graph is proportional to the singlet oxygen quantum yield. An example of a plot showing the linear relationship between the singlet oxygen emission intensity and the laser energy for the title compound of Example 78 and meso-tetraphenylporphyrin (TPP) is shown in FIG. 3.

The experiments were carried out using batches of 5 samples of the working solution of each of the title compounds of 67 to 81 plus one reference sample meso-tetraphenylporphyrin (TPP). Each run was repeated at least once. The data sets obtained for each sample were within ±5% of the mean value.

Experimental Errors

The dominant sources of error in the experiment include the shot-to-shot fluctuations in the laser and the difference in absorbances of the samples at the excitation wavelength. The values have an error of ±10%.

Standards/Reference Materials

The values for each working solution have been recorded relative to meso-tetraphenylporhyrin (TPP available from Aldrich) which has been reported to have a quantum yield of singlet oxygen production, $\Phi_A$, of 0.58 (G. Rossbroich, N. A. Garcia and S. E. Braslavsky, *J. Photochem.* 31 37 (1985)). In the present work, values for this material are cross-calibrated with those of zinc tetraphenylporphyrin (Zn TPP) and zinc phthalocyanine, obtaining values of 0.77±0.07 and 0.46±0.05 respectively. These compare with literature values of 0.73 and 0.50 (F. Wilkinson, W. P. Helman and A. B. Ross, *J. Phys. Chem. Ref. Data* (1993) 22, 113–262). This review reports a large number of values for singlet oxygen quantum yields. It is evident that, for any single material, a wide range of values may be obtained. For this reason, a reference material has been used that has been well studied and is closely related to the compounds of interest.

Results

A summary of the quantum yield data for the title compounds of Examples 67 to 81 is shown in Table 2. Values are reported relative to the standard meso-tetraphenylporhyrin having $\Phi_A$=0.58 as originally reported by G. Rossbroich, N. A. Garcia and S. E. Braslavsky; *J. Photochem.* 31 37 (1985). As discussed above, the recorded values are considered to have an error of ±10%.

TABLE 2

Quantum yield data for the title compounds of Examples 67 to 81

| Example | $\Phi_A$ |
|---|---|
| 67 | 0.65 ± 0.07 |
| 68 | 0.39 ± 0.04 |
| 69 | 0.71 ± 0.07 |
| 70 | 0.75 ± 0.07 |
| 71 | 0.72 ± 0.07 |
| 72 | 0.71 ± 0.07 |
| 73 | 0.71 ± 0.07 |
| 74 | 0.71 ± 0.07 |
| 75 | 0.71 ± 0.07 |
| 76 | 0.66 ± 0.07 |
| 77 | 0.51 ± 0.05 |
| 78 | 0.78 ± 0.08 |
| 79 | 0.76 ± 0.08 |
| 80 | 0.75 ± 0.07 |
| 81 | 0.70 ± 0.07 |

EXAMPLE 86

Balloon Catheter

Photosensitizable Mixture.

A solution of 1.0–3.0 mg of each of the title compounds of Examples 69 to 81 above in 1 ml of xylene was prepared.

Components for MED-6640 film preparation were obtained from Nusil Technology—Europe. Solution A and solution B (approximately 1:1 by volume) were mixed with stirring. The solution of the respective porphyrin of Examples 69 to 81 (see above) in xylene (50 µl per 2 ml of the mixture of solution A and B) was added to form the photosensitizable mixture.

Procedure 1.

The photosensitizable mixture described above was deposited on a balloon shaped glass former and placed in an oven and heated to 40° C. for 2 hours. The temperature was gradually raised to 150° C., maintained at 150° C. for 15 minutes and then allowed to cool. The balloon was removed from the former, and the neck and the inflation port of the balloon adapted for engagement with a catheter.

Procedure 2.

A standard silicon based polymeric catheter balloon was sprayed coated with the photosensitizable mixture described above. The coating was cured as described in Procedure 1 to form a balloon having a molecular monolayer coating of the photosensitizable compound.

EXAMPLE 87

Intraocular Lens

A polymeric intraocular lens was spray coated with the photosensitizable mixture of Example 86 above and the coating cured as described in Example 86 to form an intraocular lens having a molecular monolayer coating of the photosensitizable compound.

EXAMPLE 88

Vascular Stent

Procedure 1.

A polymeric vascular stent was spray coated with the photosensitizable mixture of Example 86 above and the coating cured as described in Example 86 to form a stent having a molecular monolayer coating of the photosensitizable compound.

Procedure 2.

A layer of gold (approximately 45 nm) was deposited on a metallic vascular stent using an Edwards 306 vacuum evaporator.

A solution of 5,5'-{4,4'-[12,12'-dithiobis-(dodecyloxy)-phenyl]}-10,10',15,15',20,20'-hexakis-(3,4,5-tridecyloxy-phenyl)-diporphyrinato zinc (24.99 mg, see Example 67) in spectroscopic grade cyclohexane (100 ml) was prepared. The gold coated stent was immersed in the diporphyrinato zinc cyclohexane solution for 24 hours. The stent was then rinsed with cyclohexane until the washings were colourless to form a stent having a molecular coating of the photosensitizable compound.

What is claimed is:

1. A compound of formula I, $$\text{(structural formula of porphyrin with substituents } R^4Y^1, Y^2R^5, Y^3R^6, R^3Y^3, Y^1R^7, R^2Y^2, Y^2R^8, R^1Y^1, Y^3R^9, XZ\text{-O-, rings A, B, C, D, metal M)}$$

wherein

R$^1$, R$^2$, R$^3$, R$^4$, R$^5$, R$^6$, R$^7$, R$^8$, and R$^9$ independently represent H, lower alkyl, lower alkenyl and lower alkynyl, tile latter three of which are optionally substituted or terminated by one or more substituents selected from halo, cyano, nitro, lower alkyl, OR$^{10}$, C(O)R$^{11}$, C(O)OR$^{12}$, C(O)NR$^{13}$R$^{14}$ and NR$^{15}$R$^{16}$;

M represents a metallic element or a metalloid element;

X represents SH, S—]$_2$, OH, NHR$^{15}$, CO$_2$H, Cl, Br, I, NCO, NCS, CN, C≡CH, CH=CH$_2$, MgCl, ZnCl, Li, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO C(O)]$_2$O, C(O)halo, C(O)OR$^{20}$, OC(O)halo, C(O)N$_3$, thiocyano, or halobenzyl;

Each Y$^1$, Y$^2$, Y$^3$ is independently absent or represents O;

Z is absent or represents lower alkylene;

R$^{10}$, R$^{11}$, R$^{12}$, R$^{13}$, R$^{14}$, and R$^{16}$ independently represent H or lower alkyl;

R$^{15}$ represents H, lower alkyl, aryl or lower alkylaryl;

R$^{17}$, R$^{18}$ and R$^{19}$ independently represent H, lower alkyl, aryl or lower alkylaryl;

R$^{20}$ represents H, lower alkyl, lower alkenyl or C(O)R$^{21}$ where R$^{21}$ represents an activating group for reaction to form an arnide bond such as N-hydroxysucciniride, N-hydroxybenzotriazole, or pentafluorophenyl ester; and A–B and C–D independently represent CH=CH or CH$_2$—CH$_2$, provided that when A–B and C–D both represent CH=CH then each Y$^1$, Y$^2$ and Y$^3$ represents oxygen, or each Y$^1$ and Y$^3$ represents oxygen and each Y$^2$ is absent.

2. A compound as claimed in claim 1 wherein M is a diamagnetic element.

3. A compound as claimed in claim 1 wherein M is selected from Zn (II), La (III), Lu (III), Y(III), In(III), Cd(II), Mg(II), Al(III), Ru, Si or Ge.

4. A compound as claimed in claim 1 wherein each Y$^1$, Y$^2$ and Y$^3$ represents oxygen.

5. A compound as claimed in claim 1 wherein one or more of R$^1$, R$^2$, R$^3$, R$^4$, R$^5$, R$^6$, R$^7$, and R$^8$ and R$^9$ represent lower alkyl.

6. A compound as claimed in claim 1 wherein each Y$^1$ and Y$^3$ represents oxygen, each Y$^2$ is absent, one or more of R$^1$, R$^3$, R$^4$, R$^6$, R$^7$ and R$^9$ represent lower alkyl and R$^2$, R$^5$ and R$^8$ represent H.

7. A compound as claimed in claim 1 wherein X represents SH, S—]2, C=CH, CH=CHx, OH, CO$_2$H, NHR$^{15}$, halo, C(O)halo, C(O)OR$^{20}$, silyl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, wherein R$^{17}$ represents methyl or ethyl.

8. A compound as claimed in claim 6 wherein halo represents Cl.

9. A compound as claimed in claim 1 wherein

R$^1$, R$^2$, R$^3$, R$^4$, R$^5$, R$^6$, R$^7$, R$^8$ and R$^9$ independently represent H or lower alkyl;

M represents a metallic element, a silicon atom, or a germanium atom;

Each Y$^1$, Y$^2$ and Y$^3$ represents oxygen, or each Y$^1$ and Y$^3$ represents oxygen and each Y$^2$ is absent; and Z is absent or represents lower alkylene.

10. A compound as claimed in claim 1 wherein

R$^1$, R$^2$, R$^3$, R$^4$, R$^5$, R$^6$, R$^7$, R$^8$ and R$^9$ independently represent linear or branched, cyclic or acyclic, C$_6$–C$_{16}$ alkyl and each Y$^1$, Y$^2$ and Y$^3$ represents oxygen; or R$^1$, R$^3$, R$^4$, R$^6$, R$^7$ and R$^9$ independently represent linear or branched, cyclic or acyclic, C$^6$–C$^{16}$ alkyl, R$^2$, R$^5$ and R$^8$ represent H, each Y$^1$ and Y$^3$ represents oxygen and each Y$^2$ is absent;

M represents Zn (II), La (III), Lu (III), Y (III), In (III), Cd (II), Mg (II), Al(II), Ru, a silicon atom or a germanium atom;

X represents SH, S—]$_2$, CH=CH$_2$, C≡CH, OH, CO$_2$H, NHR$^{15}$, halo, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$ or SihaloR$^{17}$R$^{18}$, wherein R$^{17}$ represents methyl or ethyl; and Z represents lower alkylene having an even number of carbon atoms.

11. A compound as claimed in claim 1 wherein

R$^1$, R$^2$, R$^3$, R$^4$, R$^5$, R$^6$, R$^7$, R$^8$ and R$^9$ independently represent, n-C$_6$H$_{13}$, n-C$_8$H$_{17}$, n-C$_{10}$H$_{21}$, n-C$_{12}$H$_{25}$, n-C$_{14}$H$_{29}$ or n-C$_{16}$H$_{33}$ and each Y$^1$, Y$^2$ and Y$^3$ represents oxygen; or R$^1$, R$^3$, R$^4$, R$^6$, R$^7$ and R$^9$ independently represents n-C$_6$H$_{13}$, n-C$_8$H$_{17}$, n-C$_{10}$H$_{21}$, n-C$_{12}$H$_{25}$, n-C$_{14}$H$_{29}$ or n-C$_{16}$H$_{33}$, R$^2$, R$^5$ and R$^8$ represent H, each Y$^1$ and Y$^3$ represents oxygen and each Y$^2$ is absent;

M represents Zn (H) or Mg (II);

X represents SH, S—]$_2$, CH=CH$_2$, C≡CH, OH, CO$_2$H, NHR$^5$, halo, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$ or SihaloR$^{17}$R$^{18}$, wherein R$^{17}$ represents methyl or ethyl; and Z represents n-C$_6$H$_{12}$, n-C$_8$H$_{16}$ n-C$_{10}$H$_{20}$, n-C$_{12}$H$_{24}$, n-C$_{14}$H$_{28}$, n-C$_{16}$H$_{32}$, n-C$_{18}$H$_{38}$, or n-C$_{20}$H$_{40}$, each of which groups are optionally interrupted by oxygen.

12. A compound as claimed in claim 1 wherein
$R^1$, $R^2$, $R^3$, $R^4$, $R^5$, $R^6$, $R^7$, $R^8$ and $R^9$ represent n-$C_6H_{13}$, n-$C_{10}H_{21}$ or n-$C_{16}H_{33}$ and each $Y^1$, $Y^2$ and $Y^3$ represents oxygen; or $R^1$, $R^3$, $R^4$, $R^6$, $R^7$ and $R^9$ independently represent n-$C_6H_{13}$, n-$C_{10}H_{21}$ or n-$C_{16}H_{33}$, $R^2$, $R^5$ and $R^8$ represent H, each $Y^1$ and $Y^3$ represents oxygen and each $Y^2$ is absent;

M represents Zn (II) or Mg(II);

X represents SH, S—]$_2$, CH=CH$_2$ or Si(halo)$_3$; and

Z represents n-$C_6H_{12}$, n-$C_{10}H_{20}$, n-$C_{12}H_{24}$, n-$C_{16}H_{32}$, (CH$_2$)$_{12}$—O—(CH$_2$)$_2$, (CH$_2$)$_6$—O—(CH$_2$)$_2$ or (CH$_2$)$_{16}$—O—(CH$_2$)$_2$.

13. A compound as claimed in claim 1 wherein A–B represents CH$_2$—CH$_2$ and C–D represents CH=CH.

14. A compound as claimed in claim 1 wherein A–B represents CH=CH and C–D represents CH$_2$—CH$_2$.

15. A compound as claimed in claim 1 wherein A–B and C–D represent CH=CH.

16. A process for the preparation of a compound of formula I as claimed in claim 1 which comprises:
  i. when A–B represents CH$_2$—CH$_2$ and C–D represents CH=CH, or A–B represents CH=CH and C–D represents CH$_2$—CH$_2$, reducing a compound of formula I wherein $R^1$, $R^2$, $R^3$, $R^4$, $R^5$, $R^6$, $R^7$, $R^8$, $R^9$, M, X and Z are as defined in claim 1, each $Y^1$, $Y^2$, $Y^3$ is independently absent or represents O, and A–B and C–D represent CH=CH;
  ii. when A–B and C–D represent CH=CH, reacting a compound of formula II

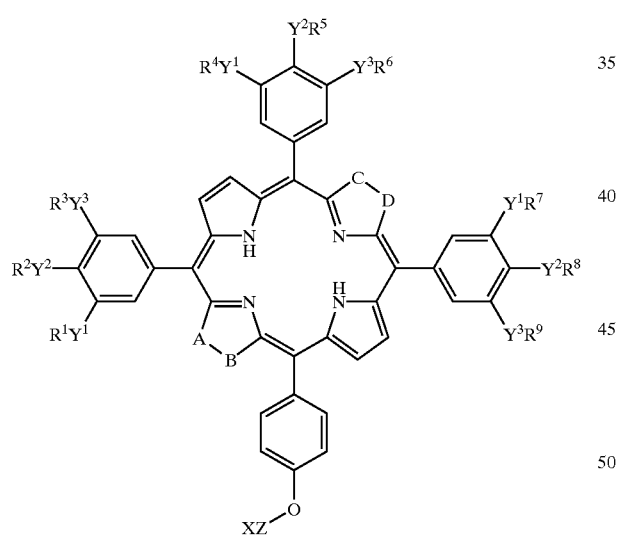

wherein $R^1$, $R^2$, $R^3$, $R^4$, $R^5$, $R^6$, $R^7$, $R^8$, $R^9$, X, $Y^1$, $Y^2$, $Y^3$ and Z are as defined in claim 1, A–B and C–D represent CH=CH, with a metallic element M or a metalloid element M as defined in claim 1;
  iii. when A–B represents CH$_2$—CH$_2$ and C–D represents CH=CH, or A–B represents CH=CH and C–D represents CH$_2$—CH$_2$, reducing a compound of formula II wherein $R^1$, $R^2$, $R^3$, $R^4$, $R^5$, $R^6$, $R^7$, $R^8$, $R^9$, X, and Z are as defined in claim 1, each $Y^1$, $Y^2$, $Y^3$ is independently absent or represents O, and A–B and C–D represent CH=CH, and reacting the resultant reduced form of compound II with a metallic element M or a metalloid element M as defined in claim 1;
  iv. when both A–B and C–D represent CH$_2$—CH$_2$, reducing a compound of formula II wherein $R^1$, $R^2$, $R^3$, $R^4$, $R^5$, $R^6$, $R^7$, $R^8$, $R^9$, X, and Z are as defined in claim 1, each $Y^1$, $Y^2$, $Y^3$ is independently absent or represents O, and A–B and C–D represent CH=CH, and reacting the resultant reduced form of compound II with a metallic element M or a metalloid element M as defined in claim 1.

17. A compound of formula II:

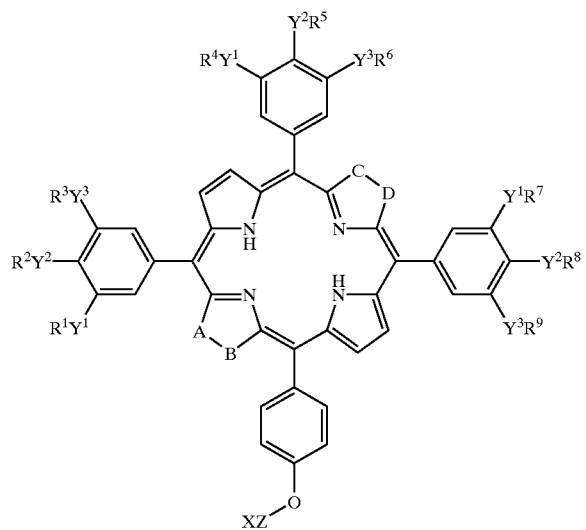

wherein $R^1$, $R^2$, $R^3$, $R^4$, $R^5$, $R^6$, $R^7$, $R^8$, $R^9$, X, $Y^1$, $Y^2$, $Y^3$ and Z are as defined in claim 1 and A–B and C–D represent CH=CH.

18. A process for the preparation of a compound of formula II as claimed in claim 17 which comprises the reaction of a compound of formula III:

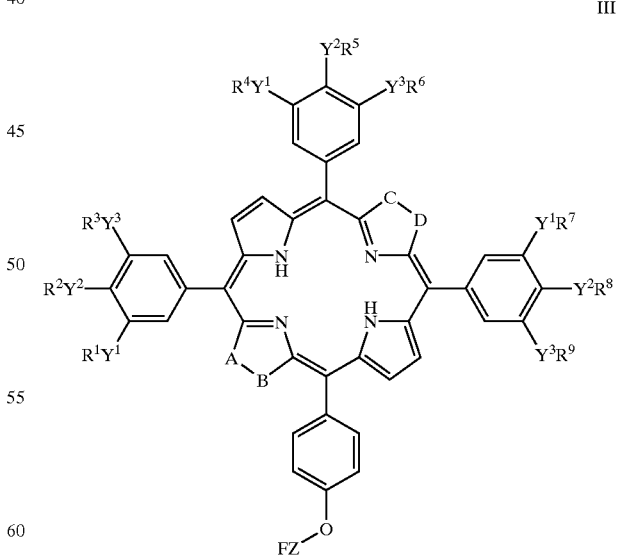

wherein $R^1$, $R^2$, $R^3$, $R^4$, $R^5$, $R^6$, $R^7$, $R^8$, $R^9$, $Y^1$, $Y^2$, $Y^3$, A–B, C–D and Z are as defined in claim 17 and F represents OH or lower alkylene-CH=CH$_2$, with a reagent that converts the ZF functional group into the desired ZX functional group, wherein X is as defined in claim 17.

19. A compound of formula III:

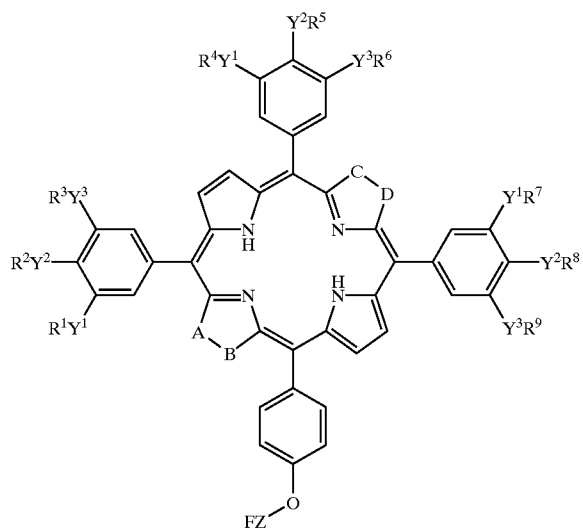

III wherein $R^1, R^2, R^3, R^4, R^5, R^6, R^7, R^8, R^9, Y^1, Y^2, Y^3$, A–B, C–D, F and Z are as defined in claim 17.

20. A process for the preparation of a compound of formula III as claimed in claim 19 which comprises reacting a compound of formula IV:

IV with a compound of formula V:

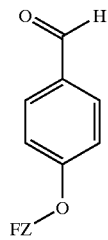

V wherein Z is as defined in claim 19, F represents OH which: is optionally protected by a removable protecting group or lower alkylene-CH=CH$_2$, and with a compound of formula VI, a compound of formula VII and a compound of formula VIII

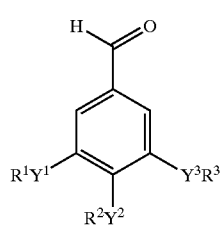

VI

VII

VIII wherein $R^1$, $R^2$, $R^3$, $R^4$, $R^5$, $R^6$, $R^7$, $R^8$, $R^9$ and $Y^1$, $Y^2$ and $Y^3$ are as defined in claim 19.

21. A composition comprising a insoluble support and a compound of formula I as defined in claim 1.

22. A composition as claimed in claim 21 wherein the compound of formula I is fixed to the surface of the insoluble support.

23. A composition as claimed in claim 21 wherein the compound of formula I is covalently bonded to the insoluble support.

24. A composition as claimed in claim 21 wherein the compound of formula I is joined to the insoluble support by a linkage (UX), wherein X represents NHR$^{15}$, OH, SH, S—]$_2$, CO$_2$H, Cl, Br, I, NCO, NCS, CN, C≡CH, CH=CH$_2$, MgCl, ZnCl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO C(O)]$_2$O, C(O)halo, C(O)OR$^{20}$, OC(O)halo, C(O)N$_3$, thiocyano or halobenzyl; and U represents OH, NHR$^{15}$, SH, CO$_2$H, Cl, Br, I, NCO, NCS, CN, C≡CH, CH=CH$_2$, MgCl, ZnCl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO, C(O)]$_2$O, C(O)halo, C(O)OR$^{20}$, OC(O)halo, C(O)N$_3$, thiocyano or halobenzyl wherein R$^{15}$, R$^{17}$, R$^{18}$, R$^{19}$ and R$^{20}$ are as previously defined for a compound of formula I.

25. A composition as claimed in claim 21 wherein the composition is represented by the formula XII:

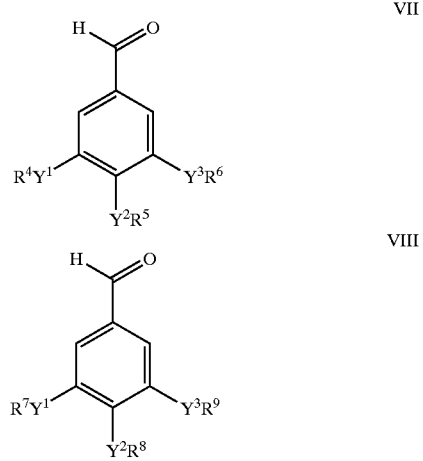

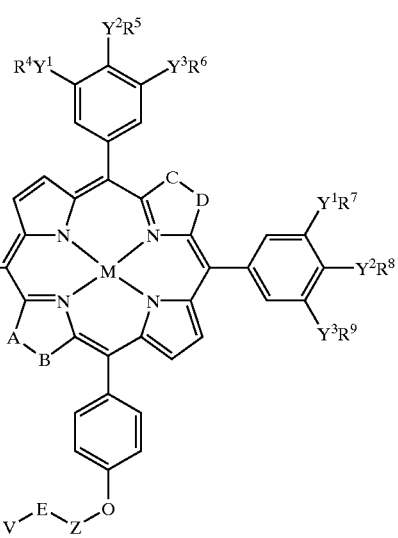

XII wherein $R^1$, $R^2$, $R^3$, $R^4$, $R^5$, $R^6$, $R^7$, $R^8$, $R^9$, $Y^1$, $Y^2$, $Y^3$, Z, A–B, C–D and M are as previously defined for a compound of formula I, IS represents the insoluble support, V is absent or represents lower alkylene or an alkylaryl group; and E represents a linkage selected from an ether, thioether, ester, keto, poly(alkyloxy), amide, amine, carbamate, urea, —CH=CH—, —C≡C—, —Si(OR$^{17}$)$_2$—, SiR$^{18}$R$^{19}$—, —SiR$^{17}$R$^{18}$, alkylene lower alkenyl, aryl or lower alkylaryl wherein $R^{17}$, $R^{18}$, and $R^{19}$ are as defined for a compound of claim 1.

26. A composition as claimed in claim 25 wherein E represents alkylene, ether, amide, silyloxy, alkynyl, alkenyl, thioether, NR$^{15}$, (CH$_2$CH$_2$O)$_m$, keto, ester or phenyl, wherein m represents 1 to 10 and R$^{15}$ is as defined for a compound of claim 1.

27. A composition for the in vivo delivery of a photosensitizable compound to a target tissue comprising a photosensitizable compound and a biocompatible insoluble support, wherein the photosensitizable compound comprises a macrocycle having at least four unsaturated five-membered nitrogen containing rings.

28. A composition as claimed in claim 27 wherein the photosensitizable compound is a benzoporphyrin, a porphycene, a purpurin, an etiopurpurin, a chlorophyll, an haematoporphyrin, a phorbine, a chlorphyrin, a verdin, a bacteriochlorin, a porphyrinogen, a phthalocyanine, or a mixture of any two or more of these.

29. A composition as claimed in claim 27 wherein the photosensitizable compound is fixed to the surface of the insoluble support.

30. A composition as claimed in claim 27 wherein the photosensitizable compound is covalently bonded to the biocompatible insoluble support.

31. A composition as claimed in claim 30 wherein the photosensitizable compound is joined to the insoluble support by a linkage (UX) derived from reaction between a group X of the photosensitizable compound and a group U of the insoluble support, wherein X represents NHR$^{15}$, OH, SH, S—]$_2$, CO$_2$H, Cl, Br, I, NCO, NCS, CN, C≡CH, CH=CH$_2$, MgCl, ZnCl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO, C(O)halo, C(O)]$_2$O, C(O)OR$^{20}$, OC(O)halo, C(O)N$_3$, thiocyano, or halobenzyl, and U represents NHR$^{15}$, OH, SH, CO$_2$H, Cl, Br, I, NCO, NCS, CN; C≡CH, CH=CH$_2$, MgCl, ZnCl, Si(OR$^{17}$)$_3$, SiR$^{18}$(OR$^{17}$)$_2$, SiR$^{18}$R$^{19}$(OR$^{17}$), Sihalo$_3$, Sihalo$_2$R$^{17}$, SihaloR$^{17}$R$^{18}$, silyl, NO$_2$, CHO, C(O)halo, C(O)]$_2$O, C(O)OR$^{20}$, OC(O)halo, C(O)N$_3$, thiocyano, or halobenzyl, wherein R$^{15}$ represents H, lower alkyl, aryl or lower alkylaryl, R$^{17}$, R$^{18}$ and R$^{19}$ independently represent H, lower alkyl, aryl or lower alkylaryl, and R$^{20}$ represents H, lower alkyl, lower alkenyl, or C(O)R$^{21}$ where R$^{21}$ represents an activating group for reaction to form an amide bond such as N-hydroxysuccinimide, N-hydroxybenzotriazole or a pentafluorophenyl ester.

32. A composition as claimed in claim 31 wherein the photosensitizable compound is a benzoporphyrin and the group X represents CO$_2$R$^{20}$ or CH=CH$_2$, a porphycene and the group X represents NHR$^{15}$ or CO$_2$R$^{20}$, a purpurin and the group X represents CO$_2$R$^{20}$ or CH=CH$_2$, a chlorophyll and the group X represents CO$_2$R$^{20}$ or CH=CH$_2$, an haematoporphyrin and the group X represents CO$_2$R$^{20}$, CH=CH$_2$ or OH, an etiopurpurin and the group X represents CO$_2$R$^{20}$, a phorbine and the group X represents CO$_2$R$^{20}$, CH=CH$_2$, OH or SH, a verdin and the group X represents CO$_2$R$^{20}$, a clilorphyrin and the group X represents C≡CH, a bacteriochlorin and the group X represents CO$_2$R$^{20}$, CH=CH$_2$ or SH, or a porphyrinogen and the group X represents CO$_2$R$^{20}$, CH=CH$_2$ or OH.

33. A composition as claimed in claim 31 wherein the X group is spaced from the photosensitizable compound by a lower alkylene or an alkylaryl group.

34. A composition as claimed in claim 31 wherein the U group is spaced from the insoluble support by a lower alkylene or an alkylaryl group.

35. A composition as claimed in claim 27 wherein the composition is represented by a compound of formula XV:

$$\text{IS—V—E—S—PC} \qquad \text{XV}$$

wherein IS represents the biocompatible insoluble support, V and S are both absent or independently represent lower alkylene or alkylaryl, PC represents the photosensitizable compound and E represents a linkage selected from an ether, thioether, keto, poly(alkyloxy), ester, amide, amine, carbamate, urea, —CH=CH—, —C=C—, —Si(OR$_{17}$)$^2$—, —SiR$^{18}$R$^{19}$—, —SiR$^{17}$R$^{18}$—, amino alcohol, amino acyl, lower alkylene, lower alkenyl, aryl or lower alkylaryl wherein R$^{17}$, R$^{18}$, and R$^{19}$ independently represent H, lower alkyl, aryl or lower alkylaryl.

36. A composition as claimed in claim 35 wherein E represents alkylene, ether, amide, silyloxy, alkynyl, alkenyl, thioether, NR$^{15}$, (CH$_2$CH$_2$O)$_m$, keto, ester, or phenyl, wherein m represents 1 to 10 and R$^{15}$ is a defined for a composition of claim 31.

37. A composition as claimed in claim 27 wherein the photosensitizable compound is a porphycene, a purpurin, a chlorophyll, a phthalocyanine or a benzoporphyrin.

38. A composition as claimed in claim 27 wherein the photosensitizable compound includes a metallic or metalloid element.

39. A composition as claimed in claim 38 wherein the metallic element is zinc.

40. A composition as claimed in claim 21 wherein the insoluble support is a polymer.

41. A composition as claimed in claim 40 wherein the insoluble support comprises polyethylene; polypropylene; polystyrene; polyacrylamide; polyamide; a resin for solid phase oligopeptide or oligonucleotide synthesis; a natural or synthetic polysaccharide; a silica composition; an alumina; or a porous solid.

42. A composition as claimed in claim 41 wherein the insoluble support is a silicone rubber.

43. A composition as claimed in claim 40 wherein the polymer forms a flexible membrane or a rigid support.

44. A composition as claimed in claim 21 wherein the insoluble support includes a noble metal.

45. A composition as claimed in claim 44 wherein the insoluble support is coated with the noble metal.

46. A composition as claimed in claim 44 wherein the noble metal is a metallic gold film.

47. A composition as claimed in claim 31 wherein the X group of the photosensitizable compound represents SH or S—]2 and wherein the insoluble support is coated with the noble metal.

48. A composition as claimed in claim 24 wherein the X group of the compound of formula I represents SH or S—]2.

49. A composition as claimed in claim 24 wherein the surface of the metallic gold is bonded to the sulphur atom of the photosensitizable compound or the sulphur atom of the compound of formula I.

50. A composition as claimed in claim 21 wherein the insoluble support is a glass surface.

51. A composition as claimed in claim 50 when dependent on claim 31 wherein the X group of the photosensitizable compound represents Si(halo)$_3$ and the photosensitizable compound is bonded through the silicon atom to the glass surface.

52. A composition as claimed in claim 50 when dependent on claim 24 wherein the X group of the compound of formula I represents Si(halo)$_3$ and the photosensitizable compound is bonded through the silicon atom to the glass surface.

53. A composition as claimed in claim 21 further including a bifunctional spacer molecule to space the photosensitizable compound from the insoluble support.

54. A composition as claimed in claim 21 for use in medicine.

55. A method of treating or preventing a disease susceptible to photodynamic treatment, such as atherosclerosis, cataracts, restenosis, secondary cataracts, endometrial ablation, bladder cancer, other cancers, proliferative diseases, inflammatory disorders or infection comprising administering the compound of claim 1 of a composition thereof.

56. A method of making a composition as claimed in claim 21 which comprises reacting a compound of formula I as defined in claim 1 with a compound of formula XIII:

XIII wherein IS represents the insoluble support, V is absent or represents lower alkylene, or an alkylaryl group and U is as previously defined for a composition of claim 24.

57. A method of making a composition as claimed in claim 27 which comprises reacting a compound of formula XVI:

PC—S—X

XVI wherein PC-S-X together represents a photosensitizable compound, PC is a benzoporphyrin, a porphycene, a purpurin, an etiopurpurin, a chlorophyll, an haematoporphyrin, a phorbine, a chlorphyrin, a verdin, a bacteriochlorin, a porphyrinogen, a phthalocyanine, or a mixture of any two or more of these; S is absent or represents lower alkylene or alkylaryl; and X is as previously defined for a composition of claim 31, with a compound of formula XVII:

V

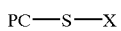

XVII wherein IS-V-U together represents the insoluble support, V is absent or represents lower alkylene or alkylaryl, and U is previously defined for a composition of claim 31.

58. A method of treating or preventing atherosclerosis and/or restenosis comprising delivering a composition as claimed in claim 21 to the target tissue; and irradiating the composition with light sufficient to generate singlet oxygen.

59. A method as claimed in claim 58 wherein the composition is delivered using a medical device.

60. A method of treating cataracts and/or secondary cataracts which comprises delivering a composition as claimed in claim 21 to the target tissue of the eye; and irradiating the composition with light sufficient to generate singlet oxygen.

61. A method as claimed in claim 60 wherein the composition is delivered using the intraocular lens as claimed in claim 60.

62. A method of treating or preventing cancer which comprises delivering a composition as claimed in claim 21 to a cancerous cell; and irradiating the composition with light sufficient to generate singlet oxygen.

63. A method as claimed in claim 62 wherein the cancer is bladder cancer and the composition is delivered using a medical device.

64. A method of producing light-induced reactive oxygen species, such as singlet oxygen which comprises irradiating a compound as claimed in claim 1 or composition thereof with light in the presence of oxygen.

65. A method for producing light-induced reactive oxygen species, such as singlet oxygen, comprising providing a compound of claim 1 or a composition thereof.

* * * * *